US009002427B2

(12) United States Patent
Tupin, Jr. et al.

(10) Patent No.: US 9,002,427 B2
(45) Date of Patent: Apr. 7, 2015

(54) APPARATUS AND METHOD FOR CONTINUOUS NONINVASIVE MEASUREMENT OF RESPIRATORY FUNCTION AND EVENTS

(75) Inventors: Joe Paul Tupin, Jr., Truckee, CA (US); Joe Paul Tupin, El Macero, CA (US); Kenneth Arlan Murray, Jr., Davis, CA (US); John David Tupin, Davis, CA (US)

(73) Assignee: LifeWave Biomedical, Inc., Los Altos, CA (US)

( * ) Notice: Subject to any disclaimer, the term of this patent is extended or adjusted under 35 U.S.C. 154(b) by 0 days.

(21) Appl. No.: 12/749,861

(22) Filed: Mar. 30, 2010
(Under 37 CFR 1.47)

(65) Prior Publication Data
US 2011/0060215 A1 Mar. 10, 2011

Related U.S. Application Data

(60) Provisional application No. 61/164,772, filed on Mar. 30, 2009.

(51) Int. Cl.
A61B 5/05 (2006.01)
A61B 5/08 (2006.01)
(Continued)

(52) U.S. Cl.
CPC ............ *A61B 5/0803* (2013.01); *A61B 5/0002* (2013.01); *A61B 5/0507* (2013.01);
(Continued)

(58) Field of Classification Search
CPC .. H04B 7/0404; H04B 7/0608; H04B 5/0081; H04B 5/6833; A61N 1/3601; A61N 1/37229; A61B 5/6833; A61B 12/006; A61B 5/0803; A61B 5/0002; A61B 5/0507; A61B 5/0861; A61B 5/087; A61B 5/091; A61B 5/1135; A61B 5/6804; A61B 5/6805; A61B 5/6831; A61B 2560/0412
USPC .................. 600/407, 463, 425, 430
See application file for complete search history.

(56) References Cited

U.S. PATENT DOCUMENTS 4,373,527 A 2/1983 Fischell
4,848,354 A 7/1989 Angelsen et al.
(Continued)

FOREIGN PATENT DOCUMENTS

DE 10345717 A1 4/2005
JP 2001-522707 A 11/2001
(Continued)

OTHER PUBLICATIONS

McKee et al.; The natural history of congestive heart failure: the Framingham study; N. Engl. J. Med.; vol. 285; No. 26; pp. 1441-1446; Dec. 23, 1971.
(Continued)

Primary Examiner — Vani Gupta
(74) Attorney, Agent, or Firm — Shay Glenn LLP

(57) ABSTRACT

An apparatus and method for non-invasive and continuous measurement of respiratory chamber volume and associated parameters including respiratory rate, respiratory rhythm, tidal volume, dielectric variability and respiratory congestion. In particular, a non-invasive apparatus and method for determining dynamic and structural physiologic data from a living subject including a change in the spatial configuration of a respiratory chamber, a lung or a lobe of a lung to determine overall respiratory health comprising an ultra wide-band radar system having at least one transmitting and receiving antenna for applying ultra wide-band radio signals to a target area of the subject's anatomy wherein the receiving antenna collects and transmits signal returns from the target area.

17 Claims, 33 Drawing Sheets

(51) Int. Cl.
    *A61B 5/087*          (2006.01)
    *A61B 5/091*          (2006.01)
    *A61B 5/113*          (2006.01)
    *A61B 5/00*            (2006.01)

(52) U.S. Cl.
    CPC ............. *A61B 5/0816* (2013.01); *A61B 5/087* (2013.01); *A61B 5/091* (2013.01); *A61B 5/1135* (2013.01); *A61B 5/6804* (2013.01); *A61B 5/6805* (2013.01); *A61B 5/6831* (2013.01); *A61B 5/6833* (2013.01); *A61B 2560/0412* (2013.01)

(56) References Cited

U.S. PATENT DOCUMENTS

| | | | |
|---|---|---|---|
| 4,901,725 A | 2/1990 | Nappholz et al. | |
| 4,984,576 A | 1/1991 | Schulenberg et al. | |
| 5,036,248 A | 7/1991 | McEwan et al. | |
| 5,088,498 A | 2/1992 | Beach et al. | |
| 5,097,837 A | 3/1992 | Reuschel | |
| 5,257,627 A | 11/1993 | Rapoport | |
| 5,271,055 A * | 12/1993 | Hsieh et al. | 378/95 |
| 5,274,271 A | 12/1993 | McEwan | |
| 5,292,348 A | 3/1994 | Saumarez et al. | |
| 5,345,471 A | 9/1994 | McEwan | |
| 5,361,070 A | 11/1994 | McEwan | |
| 5,457,394 A | 10/1995 | McEwan | |
| 5,465,094 A | 11/1995 | McEwan | |
| 5,510,800 A | 4/1996 | McEwan | |
| 5,511,553 A | 4/1996 | Segalowitz | |
| 5,512,834 A | 4/1996 | McEwan | |
| 5,517,198 A | 5/1996 | McEwan | |
| 5,519,400 A | 5/1996 | McEwan | |
| 5,521,600 A | 5/1996 | McEwan | |
| 5,523,760 A | 6/1996 | McEwan | |
| 5,540,733 A | 7/1996 | Testerman et al. | |
| 5,560,363 A | 10/1996 | Torp et al. | |
| 5,563,605 A | 10/1996 | McEwan | |
| 5,573,012 A | 11/1996 | McEwan | |
| 5,576,627 A | 11/1996 | McEwan | |
| 5,581,256 A | 12/1996 | McEwan | |
| 5,589,838 A | 12/1996 | McEwan | |
| 5,609,059 A | 3/1997 | McEwan | |
| 5,610,611 A | 3/1997 | McEwan | |
| 5,630,216 A | 5/1997 | McEwan | |
| 5,661,385 A | 8/1997 | McEwan | |
| 5,662,115 A | 9/1997 | Torp et al. | |
| 5,682,164 A | 10/1997 | McEwan | |
| 5,736,958 A | 4/1998 | Turpin | |
| 5,738,102 A | 4/1998 | Lemelson | |
| 5,754,144 A | 5/1998 | McEwan | |
| 5,757,320 A | 5/1998 | McEwan | |
| 5,758,652 A | 6/1998 | Nikolic | |
| 5,766,208 A | 6/1998 | McEwan | |
| 5,767,953 A | 6/1998 | McEwan | |
| 5,774,091 A | 6/1998 | McEwan | |
| 5,805,110 A | 9/1998 | McEwan | |
| 5,820,561 A | 10/1998 | Olstad et al. | |
| 5,832,772 A | 11/1998 | McEwan | |
| 5,853,005 A | 12/1998 | Scanlon | |
| 5,883,591 A | 3/1999 | McEwan | |
| 5,980,463 A | 11/1999 | Brockway et al. | |
| 6,031,421 A | 2/2000 | McEwan | |
| 6,126,611 A | 10/2000 | Bourgeois et al. | |
| 6,185,457 B1 | 2/2001 | Kroll et al. | |
| 6,213,947 B1 | 4/2001 | Phillips | |
| 6,233,479 B1 | 5/2001 | Haddad et al. | |
| 6,292,433 B1 | 9/2001 | Gilbert et al. | |
| 6,325,761 B1 | 12/2001 | Jay | |
| 6,348,898 B1 | 2/2002 | Rosenbury et al. | |
| 6,373,428 B1 | 4/2002 | McEwan | |
| 6,414,627 B1 | 7/2002 | McEwan | |
| 6,454,711 B1 | 9/2002 | Haddad et al. | |
| 6,454,719 B1 | 9/2002 | Greenhut | |
| 6,471,689 B1 | 10/2002 | Joseph et al. | |
| 6,491,639 B1 | 12/2002 | Turcott | |
| 6,535,161 B1 | 3/2003 | McEwan | |
| 6,676,608 B1 | 1/2004 | Keren | |
| 6,738,044 B2 | 5/2004 | Holzrichter et al. | |
| 6,753,783 B2 | 6/2004 | Friedman et al. | |
| 6,829,378 B2 | 12/2004 | DiFilippo et al. | |
| 6,899,684 B2 * | 5/2005 | Mault et al. | 600/531 |
| 6,914,552 B1 | 7/2005 | McEwan | |
| 6,944,107 B2 | 9/2005 | Fukushima et al. | |
| 6,984,207 B1 | 1/2006 | Sullivan et al. | |
| 7,003,348 B1 | 2/2006 | Brewer et al. | |
| 7,025,729 B2 | 4/2006 | de Chazal et al. | |
| 7,075,485 B2 | 7/2006 | Song et al. | |
| 7,224,944 B2 | 5/2007 | McEwan | |
| 7,226,427 B2 | 6/2007 | Steen | |
| 7,294,105 B1 | 11/2007 | Islam | |
| 7,304,580 B2 | 12/2007 | Sullivan et al. | |
| 7,305,052 B2 | 12/2007 | Spiridon et al. | |
| 7,432,847 B2 | 10/2008 | Fedotov et al. | |
| 7,652,581 B2 | 1/2010 | Gentry et al. | |
| 7,654,962 B2 | 2/2010 | Sullivan | |
| 7,725,150 B2 | 5/2010 | Tupin, Jr. et al. | |
| 7,970,475 B2 * | 6/2011 | Tehrani et al. | 607/42 |
| 2002/0032383 A1 | 3/2002 | Weil et al. | |
| 2002/0156379 A1 | 10/2002 | Angelsen et al. | |
| 2003/0088180 A1 | 5/2003 | Van Veen et al. | |
| 2003/0090407 A1 | 5/2003 | Santhoff | |
| 2004/0049118 A1 | 3/2004 | Ideker et al. | |
| 2004/0100376 A1 * | 5/2004 | Lye et al. | 340/539.12 |
| 2004/0111045 A1 | 6/2004 | Sullivan et al. | |
| 2004/0123667 A1 * | 7/2004 | McGrath | 73/704 |
| 2004/0249257 A1 | 12/2004 | Tupin, Jr. et al. | |
| 2005/0052322 A1 | 3/2005 | Park et al. | |
| 2005/0085687 A1 | 4/2005 | Mackin et al. | |
| 2005/0101841 A9 * | 5/2005 | Kaylor et al. | 600/300 |
| 2005/0267376 A1 | 12/2005 | Marossero et al. | |
| 2006/0058681 A1 | 3/2006 | Eberle et al. | |
| 2006/0094937 A1 | 5/2006 | Immoreev et al. | |
| 2006/0154642 A1 | 7/2006 | Scannell, Jr. | |
| 2006/0200033 A1 | 9/2006 | Keren et al. | |
| 2006/0241409 A1 * | 10/2006 | Winters et al. | 600/430 |
| 2006/0274031 A1 | 12/2006 | Yuen et al. | |
| 2007/0027367 A1 | 2/2007 | Oliver et al. | |
| 2007/0043585 A1 | 2/2007 | Matos | |
| 2007/0055164 A1 | 3/2007 | Huang et al. | |
| 2007/0135866 A1 | 6/2007 | Baker et al. | |
| 2007/0156031 A1 | 7/2007 | Sullivan et al. | |
| 2007/0161883 A1 | 7/2007 | Ayari et al. | |
| 2007/0276270 A1 | 11/2007 | Tran | |
| 2008/0001735 A1 | 1/2008 | Tran | |
| 2008/0004904 A1 | 1/2008 | Tran | |
| 2008/0009685 A1 | 1/2008 | Kim et al. | |
| 2008/0027337 A1 | 1/2008 | Dugan et al. | |
| 2008/0058740 A1 | 3/2008 | Sullivan et al. | |
| 2008/0119896 A1 | 5/2008 | Wong et al. | |
| 2008/0129511 A1 | 6/2008 | Yuen et al. | |
| 2008/0146938 A1 | 6/2008 | Hazard et al. | |
| 2008/0169931 A1 | 7/2008 | Gentry et al. | |
| 2008/0243431 A1 | 10/2008 | Wai | |
| 2008/0294019 A1 | 11/2008 | Tran | |
| 2009/0022379 A1 * | 1/2009 | Tashiro et al. | 382/131 |
| 2009/0048500 A1 | 2/2009 | Corn | |
| 2009/0054737 A1 | 2/2009 | Magar et al. | |
| 2009/0073991 A1 | 3/2009 | Landrum et al. | |
| 2009/0076336 A1 | 3/2009 | Mazar et al. | |
| 2009/0076340 A1 | 3/2009 | Libbus et al. | |
| 2009/0076341 A1 | 3/2009 | James et al. | |
| 2009/0076342 A1 | 3/2009 | Amurthur et al. | |
| 2009/0076343 A1 | 3/2009 | James et al. | |
| 2009/0076344 A1 | 3/2009 | Libbus et al. | |
| 2009/0076345 A1 | 3/2009 | Manicka et al. | |
| 2009/0076346 A1 | 3/2009 | James et al. | |

(56) References Cited

U.S. PATENT DOCUMENTS

| | | | |
|---|---|---|---|
| 2009/0076348 | A1 | 3/2009 | Manicka et al. |
| 2009/0076349 | A1 | 3/2009 | Libbus et al. |
| 2009/0076350 | A1 | 3/2009 | Bly et al. |
| 2009/0076363 | A1 | 3/2009 | Bly et al. |
| 2009/0076364 | A1 | 3/2009 | Libbus et al. |
| 2009/0076397 | A1 | 3/2009 | Libbus et al. |
| 2009/0076401 | A1 | 3/2009 | Mazar et al. |
| 2009/0076405 | A1 | 3/2009 | Amurthur et al. |
| 2009/0076410 | A1 | 3/2009 | Libbus et al. |
| 2009/0076559 | A1 | 3/2009 | Libbus et al. |
| 2009/0203972 | A1 | 8/2009 | Heneghan et al. |
| 2009/0227882 | A1 | 9/2009 | Foo |
| 2009/0238426 | A1 | 9/2009 | Fear et al. |
| 2011/0112403 | A1 | 5/2011 | Machtey et al. |
| 2011/0172540 | A1 | 7/2011 | Jackson |
| 2011/0282228 | A1* | 11/2011 | Shiner et al. ............... 600/534 |
| 2012/0041281 | A1 | 2/2012 | Tupin, Jr. et al. |
| 2012/0059268 | A1 | 3/2012 | Tupin, Jr. |
| 2013/0245436 | A1 | 9/2013 | Tupin, Jr. et al. |

FOREIGN PATENT DOCUMENTS

| | | |
|---|---|---|
| JP | 2002-538872 | 11/2002 |
| WO | WO01/70103 A2 | 9/2001 |
| WO | WO2007/027660 A2 | 3/2007 |
| WO | WO2007/101343 A1 | 9/2007 |
| WO | WO2007/120904 A2 | 10/2007 |
| WO | WO2007/124126 A2 | 11/2007 |
| WO | WO2007/143535 A2 | 12/2007 |
| WO | WO2008/057883 A2 | 5/2008 |
| WO | WO2009/029453 A2 | 3/2009 |
| WO | WO2009/036256 A1 | 3/2009 |
| WO | WO2009/036306 A1 | 3/2009 |
| WO | WO2009/036313 A1 | 3/2009 |

OTHER PUBLICATIONS

Neubauer, Stefan; The failing heart—an engine out of fuel; N. Engl. J. Med.; vol. 356; No. 11; pp. 1140-1151; Mar. 15, 2007.

Tupin, Jr. et al.; U.S. Appl. No. 12/765,680 entitled "Fetal Monitoring Device and Methods," filed Apr. 22, 2010.

Tupin, Jr. et al.; U.S. Appl. No. 12/759,909 entitled "System and Method for Extracting Physiological Data Using Ultra-Wideband Radar and Improved Signal Processing Techniques," filed Apr. 14, 2010.

Tupin, Joe Paul Jr.; U.S. Appl. No. 12/601,665 entitled "System and Method for Non-Invasive Instantaneous and Continuous Measurement of Cardiac Chamber Volume," filed Nov. 24, 2009.

Tupin, Jr. et al.; A novel ultra-wideband sensor used for cardiopulmonary monitoring; 5 pgs.; Mar. 9, 2009.

Luo et al.; A two-layer dielectric absorber covering a wide frequency range; Ceramics Int; 33(2):197-200; Mar. 2007.

Staderini, Enrico M.; UWB Radars in Medicine; IEEE Aerospace and Electronic Systems; 17(1):13-18; Jan. 2002.

Tupin, Jr.; U.S. Appl. No. 13/902,623 entitled "System and Method for Non-Invasive Instantaneous and Continuous Measurement of Cardiac Chamber Volume," filed May 24, 2013.

Li et al.; The parameters selection of matching layer of ultrasonic transducers; Journal of Shaanxi Normal University (Natural Science Edition); 37(5); pp. 38-41; Sep. 30, 2009 (Chinese w/ English Abs. and CN Office Action).

Wells; Biomedical Ultrasonics; Academic Press; pp. 54; Mar. 1977.

Zhao; The application of acoustic matching of air-media ultrasonic converter; Automated Instrumentation; 16(12); pp. 18-21; Dec. 31, 1995 (Chinese w/ English Abs. and CN Office Action).

Dissanayake et al.; UWB antenna impedance matching in biomedical implants, antennas and propagation; EuCAP; pp. 3523-3526; 2009 (year of pub. sufficiently earlier than effective US filed and any foreign priority date).

* cited by examiner

|  | Inflated | Deflated |
|---|---|---|
| Normal | 20 | 47 |
| Congested | 39 | 66 |

*Fig. 36*

|  | Cumulative Average | | | Cumulative | |
|---|---|---|---|---|---|
|  | Inflated | Deflated | | Inflated | Deflated |
| Normal | 23 | 49 | | 113 | 247 |
| Stage 1 Congestion | 25 | 55 | | 127 | 277 |
| Stage 2 Congestion | 34 | 60 | | 170 | 299 |
| Stage 3 Congestion | 39 | 66 | | 195 | 330 |

*Fig. 37*

| Lung Portion Sensor Location | Normal | | Stage 1 Congestion | | Stage 2 Congestion | | Stage 3 Congestion | |
|---|---|---|---|---|---|---|---|---|
|  | Inflated | Deflated | Inflated | Deflated | Inflated | Deflated | Inflated | Deflated |
| Left Superior Lobe | 20 | 47 | 20 | 47 | 20 | 47 | 25 | 55 |
| Left Inferior Lobe | 25 | 52 | 32 | 67 | 55 | 80 | 60 | 80 |
| Right Superior Lobe | 20 | 47 | 20 | 47 | 20 | 47 | 25 | 55 |
| Right Middle Lobe | 23 | 49 | 23 | 49 | 35 | 55 | 40 | 65 |
| Right Inferior Lobe | 25 | 52 | 32 | 67 | 40 | 70 | 45 | 75 |
| Cumulative | 113 | 247 | 127 | 277 | 170 | 299 | 195 | 330 |
| Cumulative Average | 23 | 49 | 25 | 55 | 34 | 60 | 39 | 66 |

*Fig. 38*

| Lung Portion Sensor Location | Normal | Stage 1 Congestion | Stage 2 Congestion | Stage 3 Congestion |
|---|---|---|---|---|
| Left Superior Lobe | 20 | 20 | 20 | 25 |
| Left Inferior Lobe | 25 | 32 | 55 | 60 |
| Right Superior Lobe | 21 | 22 | 25 | 28 |
| Right Middle Lobe | 23 | 23 | 35 | 40 |
| Right Inferior Lobe | 25 | 32 | 40 | 45 |
| Cumulative | 114 | 129 | 175 | 198 |
| Cumulative Average | 23 | 26 | 35 | 40 |

Fig. 39

APPARATUS AND METHOD FOR CONTINUOUS NONINVASIVE MEASUREMENT OF RESPIRATORY FUNCTION AND EVENTS

CROSS REFERENCE TO RELATED APPLICATION

This application claims the benefit under 35 U.S.C. 119 of U.S. Provisional Patent Application No. 61/164,772, filed Mar. 30, 2009, titled "APPARATUS AND METHOD FOR CONTINUOUS NONINVASIVE MEASUREMENT OF RESPIRATORY FUNCTION AND EVENTS".

This application may be related to co-pending U.S. patent application Ser. No. 10/456,290 titled "SYSTEM AND METHOD FOR EXTRACTING PHYSIOLOGICAL DATA USING ULTRA-WIDEBAND RADAR AND IMPROVED SIGNAL PROCESSING TECHNIQUES", filed on Jun. 2, 2003.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates in general to respiratory monitoring. More particularly, the present invention relates to an apparatus and method for non-invasive physiological monitoring to determine respiratory rate, rhythm, tidal volume and other functional metrics including detection of respiratory events and trends that may signal abnormal physiological functionality.

BACKGROUND OF THE INVENTION

Many diverse medical conditions directly affect the lungs and overall pulmonary function. Accordingly, respiratory data can provide valuable information concerning the existence, onset and progression of a disease or injury affecting a patient. Several different methods are currently used to monitor pulmonary or respiratory functionality. Unfortunately, existing respiratory monitoring methods are complex, inconvenient, limited in scope or simply too expensive. None lend themselves to effective use in an ambulatory setting and instead, generally require that a subject be monitored in a hospital or doctor's office.

Consequently, delivery of a simple, reliable and portable apparatus to collect desired respiratory information would be invaluable to society and satisfy a long-felt need in the healthcare profession. The ability to safely, easily, and accurately measure respiratory function along with specific intermittent events and overall trends will provide the healthcare professional with critical information needed to provide appropriate and timely care. An apparatus that provides a reliable, simple means to measure and monitor respiratory function in conjunction with other physiological metrics, including heart rate, has been highly sought after. Additionally, the provision of such a device for use in an ambulatory setting would enable a health care provider to gain unique insight into a person's pulmonary responses to various stresses in a normal, everyday setting. This has been a long-felt need for decades which others have yet been unable to satisfy.

Both qualitative and quantitative aspects of respiratory function need to be monitored to assess, diagnose and treat problematic respiratory symptoms which may be driven by one of many respiratory, cardiac and other diseases. In particular, respiratory rate, rhythm, and, tidal volume are important parameters commonly measured to aid a physician in determining a patient's state of respiratory health and uncover other conditions that might affect respiratory health. It would be highly desirable to provide a respiratory monitoring apparatus that can easily be used by an individual or caregiver, regardless of the individual's current health status, mobility or lack thereof. In addition, it would be highly desirable to provide such an apparatus that can remain continuously with a patient during transition within a hospital setting and subsequently during outpatient treatment. Still further, it would be highly desirable to provide such an apparatus for nonintrusive use by an individual during normal daily routines to aid in the capture of respiratory events and trends which may be indicative of an adverse condition which might otherwise go unnoticed.

To understand the operation of the present invention and its utility and importance in providing assessment of respiratory function and performance, it will help to have a reasonable understanding of the various mechanical aspects of respiratory function along with the current methods used to measure important respiratory metrics. Following is a directed overview of relevant elements of respiratory function.

1. Related Art

An assessment of the mechanics of breathing deals with the movement of the diaphragm and associated muscles, movement of the rib-cage and associated musculature, and, physical characteristics of the lungs themselves. The muscular action controls breathing and it causes the volume of the lungs to increase and decrease in order to regulate the content of carbon dioxide in the arterial blood. Currently, there are various methods used to assess the function of each breathing mechanism component, however no single device is known that can easily, conveniently and accurately evaluate the overall performance of breathing. Existing methods used for respiratory assessment include: (1) the displacement method, which consists of wearing a chest wrap with adhesive sensors attached to it, (2) the thermistor method, which requires a facial mask for measuring respiration heat, (3) the impedance pneumography test, which attaches electrodes on the surface of the skin and measures chest movement, (4) the $CO_2$ method, which consists of a continuous measurement of expired air and the utilization of infrared rays, and, (5) a piezoelectric external mechanical movement detection and correlation method. It is important to note that all of the above approaches fail to obtain direct information concerning the both the mechanical aspects of the respiratory process and the physiological changes within the lungs themselves during the respiratory process.

Certain elements of respiration may be measured directly using, for example, external breathing masks. Breathing masks, however, are generally not well tolerated by patients for extended periods of time. Additionally, such masks are not convenient for ambulatory patients. Additionally, a system having one or more sensors disposed at or near the surface of a patient's body for monitoring physiological variables of a patient in real time, including respiratory sounds for the detection of abnormal breathing patterns, is generally disclosed in U.S. Pat. No. 5,738,102 issued to Lemelson.

Further, qualitative assessments of respiratory function are made via impedance measurements using implanted electrodes for detecting changes in thoracic impedance associated with changing lung volume during inspiration and expiration.

Tidal volume and respiration rate may be approximated from the measured impedance. Normal changes in respiration rate and tidal volume in response to exercise are measured using impedance sensing in some cardiac pacemakers to provide a sensor-indicated pacing rate for rate-responsive cardiac pacing. See, for example, U.S. Pat. No. 4,901,725 issued to Nappholz.

Still further, respiratory signals may be extracted from other physiological signals that can be obtained from implantable sensors. For example, physiological signals, such as subcutaneous ECG, cardiac electrogram (EGM), blood pressure, and heart sound signals, typically contain cyclical amplitude changes caused by the respiratory cycle. Pulsus paradoxus refers to a decrease in arterial blood pressure that occurs during inspiration. A device for measuring pulsus paradoxus for assessing and monitoring patients with respiratory disease is generally disclosed in U.S. Pat. No. 6,325,761 issued to Jay, incorporated herein by reference in its entirety. A method for computing tidal volume as a function of extracted blood pressure information indicative of the change in blood pressure that occurs over a respiratory cycle is generally disclosed in U.S. Pat. No. 5,980,463, issued to Brockway, et al. Implantable cardiac rhythm management or cardiac monitoring devices may sense ECG, EGM, blood pressure and/or other physiological signals that vary due to the influence of respiration.

Each of the above existing methods is relatively complex, expensive and somewhat invasive. They do not lend themselves to use outside a hospital or doctor's office. It would be advantageous and beneficial to provide an apparatus capable of monitoring the desired parameters more simply and non-invasively, in a manner that allows continuous use in essentially any location.

2. Respiratory Metrics

Monitoring and assessment of lung function is an indispensable tool for diagnosing and monitoring respiratory disease states, along with the root causes of the current respiratory state or other diseases associated with the respiratory state. There are several key respiratory functional metrics that are considered when assessing an individual's respiratory health. FIG. 1 is a chart illustrating the relationship between the various standard metrics. A first metric is an individual's total lung capacity, which is a cumulative measure of the additional metrics of inspiratory reserve volume, including tidal volume, expiratory reserve volume, and residual volume. Inspiratory reserve volume is the additional air that can be inhaled after a normal tidal breath in. Tidal volume is the normal volume of air breathed in and out. Expiratory reserve volume is the amount of additional air that can be breathed out after the end expiratory level of normal breathing. Residual volume is the amount of air left in the lungs after a maximal exhalation, i.e., the amount of air that is always in the lungs and can never be expired.

Measuring an individual's total lung capacity can provide critical background information about a person, and, needs to be considered in making diagnoses. An individual's total lung capacity typically depends on such factors as the person's age, height, weight, and sex. Total lung capacity normally ranges between 4 to 6 liters. Females tend to have a 20-25% lower total lung capacity than males. Tall people tend to have a larger total lung capacity than shorter people. Smokers tend to have a lower total lung capacity than nonsmokers. Lung capacity can also be affected by altitude. People who are born and live at sea level will typically have a smaller lung capacity than people who spend their lives at a high altitude.

In addition to measuring total lung capacity, one also measures tidal volume, the volume of air breathed in with an average breath. Tidal volume is typically between 0.5 to 1 liters. Measurement of tidal volume and changes or trends in tidal volume provides critical diagnostic data concerning pulmonary function and performance. For example, typical resting adult respiratory rates are 10 to 20 breaths per minute with approximately a third of the breath time involved in inspiration. Human lungs, to a certain extent, are overbuilt and have a tremendous reserve volume as compared to the normal oxygen exchange requirements when an individual is at rest. For example, individuals can smoke for years without having a noticeable decrease in lung function while still or moving slowly. For example, although total lung capacity may be between 4 to 6 liters, with tidal volume between 0.5 to 1 liters, only a small portion of the total lung capacity is typically in use, approximately between 8% to a maximum of 25%. While in a resting state, only a small portion of the lungs are actually perfused with blood for gas exchange. As oxygen requirements increase due to exercise, a greater volume of the lungs is perfused, allowing the body to reach its $CO_2/O_2$ exchange requirements. Hence, the smoker engaged in exercise will most likely experience an oxygen deficit due to existing damage to the lungs which prevents perfusion of a greater volume of the lung area.

It would be advantageous to provide a convenient, small apparatus and sensor capable of both qualitatively and quantitatively measuring the various pulmonary functional parameters including respiratory rate, respiratory rhythm, tidal volume, and, total lung capacity, along with other calculable and derivative parameters such as vital capacity and residual volume, among others. It would also be advantageous to provide such an apparatus capable of measuring changes in perfusion in each lobe of one or both lungs.

3. Respiratory Metrics of Primary Respiratory Diseases

Respiratory diseases can generally be categorized as obstructive, restrictive, parenchymal, vascular or infectious. Following is a brief overview of these respiratory disease types relevant to the application of the present invention.

Obstructive lung diseases (OLD) are characterized by an increase in airway resistance, evidenced by a decrease in Peak Expiratory Flow Rate (PEFR) measured in spirometry by the Forced Expiratory Volume in 1 Second (FEV1). The Residual Volume, the volume of air left in the lungs following full expiration, is greatly increased in OLD, leading to the clinical sign of chest over-inflation in patients with severe disease. Many patients with chronic OLD present with "barrel chest"—a deformity of outward rib displacement due to chronic over-inflation of the lungs. Patients with OLD typically have 'large, floppy lungs'. In Obstructive Lung Disease, the lung volume (Total Lung Capacity, TLC), Vital Capacity (VC), Tidal Volume (VT) and Expiratory Reserve Volume (ERV) remain relatively unchanged. It would be advantageous to provide a simple, noninvasive apparatus and sensor that could monitor and track chest over-inflation and lung size in conjunction with the other functional pulmonary metrics to assess the onset and progression of OLD in patients in a continuous manner. Some notable obstructive lung diseases which could be more competently assessed through the provision and use of such an apparatus and sensor include emphysema, bronchitis, asthma, chronic obstructive pulmonary disease, bronchiectasis, byssinosis, bronchiolitis, and, asbestosis.

Restrictive lung diseases (RLD) are characterized by a loss of airway compliance, causing incomplete lung expansion (i.e. via increased lung 'stiffness'). This change manifests itself in reduced Total Lung Capacity, Inspiratory Capacity and Vital Capacity. In contrast to OLD, RLD values for Tidal Volume, Expiratory Reserve Volume, Functional Residual Capacity and Respiratory Volume are unchanged. It would be advantageous to provide a simple, noninvasive apparatus and sensor that could monitor and track changes in total lung capacity, inspiratory capacity and vital capacity along with other pulmonary metrics to assess the onset and progression of RLD in patients in a continuous manner. Notable restrictive lung diseases which could be more competently assessed through the provision and use of such an apparatus and sensor include fibrosis, sarcoidosis, pleural effusion, hypersensitivity pneumonitis, asbestosis, pleurisy, lung cancer, infant respiratory distress syndrome (IRDS), acute respiratory distress syndrome (ARDS), neurologic diseases affecting the ability of the body to alter respiration rate including spinal cord injury, mechanical diseases affecting pulmonary musculature including myasthenia gravis, and, severe acute respiratory syndrome (SARS).

Parenchymal lung disease is characterized by damage to the lungs which may be caused by environmental or other factors. The basic functional units of the lung, the alveoli, are referred to as the lung parenchyma. Chronic obstructive pulmonary disease (COPD), also known as chronic obstructive airway disease (COAD), is a group of diseases characterized by the pathological limitation of airflow in the airway that is not fully reversible. COPD is the umbrella term for chronic bronchitis, emphysema and a range of other lung disorders. It is most often due to tobacco smoking, but can be due to other airborne irritants such as coal dust, asbestos or solvents, as well as congenital conditions. Diseases such as COPD are characterized by destruction of the alveoli and are therefore referred to as parenchymal lung diseases. Signs of parenchymal lung disease include, but are not limited to, hypoxemia (low oxygen in the blood) and hypercapnoea (high carbon dioxide in the blood). In addition, parenchymal lung diseases can present with symptoms of elevated respiratory rate with corresponding reduced tidal volume. Chronic complications of parenchymal lung disease include reduced respiratory drive, right ventricular hypertrophy, and right heart failure (cor pulmonale). Notable parenchymal diseases include COPD, sarcoidosis, pulmonary fibrosis, and, emphysema. It would be advantageous to provide a simple, noninvasive apparatus and sensor that could continuously and directly monitor respiratory rate in correspondence with changes in tidal volume in conjunction with the other functional pulmonary metrics to assess the onset and progression of parenchymal lung diseases in patients.

Vascular lung disease refers to conditions which affect the pulmonary capillary vasculature. Alterations in the vasculature manifest in a general inability to exchange blood gases such as oxygen and carbon dioxide, in the vicinity of the vascular damage (other areas of the lung may be unaffected). Signs of vascular lung disease include, but are not limited to, hypoxemia (low oxygen in the blood) and hypercapnoea (high carbon dioxide in the blood). Chronic complications of vascular lung disease include reduced respiratory drive, right ventricular hypertrophy, and right heart failure (cor pulmonale). In addition, parenchymal lung diseases can present with symptoms of elevated respiratory rate with corresponding reduced tidal volume. For example, pulmonary hypertension, a vascular lung disease, is an increase in blood pressure in the pulmonary artery, pulmonary vein, or pulmonary capillaries, together known as the lung vasculature, leading to shortness of breath, dizziness, fainting, and other symptoms, all of which are exacerbated by exertion. Notable vascular lung diseases include pulmonary edema, pulmonary embolism, and, pulmonary hypertension. It would be advantageous to provide a simple, noninvasive apparatus and sensor that could continuously and directly monitor respiratory rate indicating breathlessness and tidal volume in conjunction with the other functional pulmonary metrics to assess the onset and progression of vascular lung diseases in patients.

Infectious lung diseases are typically caused by one of many infectious agents able to infect the mammalian respiratory system, for example, the bacterium *Streptococcus pneumoniae*. The clinical features and treatment options vary greatly between infectious lung disease sub-types as each type may be caused by a different infectious agent, with different pathogenesis and virulence. Features also vary between upper respiratory tract infection, including strep throat and the common cold; and lower respiratory tract infection, including pneumonia and pulmonary tuberculosis. Lower respiratory tract infections place a considerable strain on the health budget and are generally more serious than upper respiratory infections. Since 1993 there has been a slight reduction in the total number of deaths from lower respiratory tract infection. However in 2002 they were still the leading cause of deaths among all infectious diseases accounting for 3.9 million deaths worldwide and 6.9% of all deaths that year.

These infectious lung diseases typically present with symptoms of shortened breath resulting in a corresponding increase in respiratory rate. It would be advantageous to provide a simple, noninvasive apparatus and sensor that could continuously and directly monitor respiratory rate and tidal volume in conjunction with the other functional pulmonary metrics to assess the onset and progression of infectious lung disease in patients.

Respiratory tumor can refer to either neoplastic (cancerous) or non-neoplastic masses within the lungs or lung parenchyma. Respiratory neoplasms are abnormal masses of tissue within the lungs or parenchyma whose cell of origin may or may not be lung tissue (many other neoplasms commonly metastasize to lung tissue). Respiratory neoplasms are most often malignant, although there are non-malignant neoplasms which can affect lung tissue. Respiratory neoplasms include mesothelioma, small cell lung cancer, and, non-small cell lung cancer. Each of these typically present with symptoms of shortness of breath. Consequently, it would be advantageous to provide a simple, noninvasive apparatus and sensor that could continuously and directly monitor respiratory rate and tidal volume thereby assessing shortness of breath, in conjunction with the other functional pulmonary metrics, to allow assessment of the onset and progression of infectious lung diseases in patients.

4. Respiratory Metrics and Indicators of Cardiac Failure

Measurement of pulmonary functionality and performance can be a tremendous aid in identifying symptoms associated with cardiac problems. For example, congestive heart failure (CHF) is a condition that can result from any structural or functional cardiac disorder that impairs the ability of the heart to fill with or pump a sufficient amount of blood through the body. Congestive heart failure is often undiagnosed due to a lack of a universally agreed definition and difficulties in diagnosis, particularly when the condition is considered "mild". Even with the best therapy, heart failure is associated with an annual mortality of 10% (Stefan Neubauer (2007). "The failing heart—an engine out of fuel". *N Engl J Med* 356 (11): 1140-51). It is the leading cause of hospitalization in people older than 65. (McKee P A, Castelli W P, McNamara P M, Kannel W B (1971). "The natural history of congestive heart failure: the Framingham study". *N. Engl. J. Med.* 285 (26): 1441-6.)

The symptoms of congestive heart failure depend largely on the side of the heart exhibiting predominant failure. If both sides are functioning inadequately, symptoms and signs from both categories may be present. Given that the left side of the heart pumps blood from the lungs to the organs, failure to do so leads to congestion of the lung veins and symptoms that reflect this, as well as reduced supply of blood to the tissues. The predominant respiratory symptom is shortness of breath on exertion, dyspnea (or, in severe cases at rest) along with becoming easily fatigued. Orthopnea is increasing breathlessness on reclining, measured in the number of pillows required to lie comfortably. Paroxysmal nocturnal dyspnea (PND) is a nighttime attack of severe breathlessness, usually several hours after going to sleep. Poor circulation to the body leads to dizziness, confusion and diaphoresis (excessive sweating) and cool extremities at rest. It is most closely associated with congestive heart failure. PND is often relieved by sitting upright, but not as quickly as simple orthopnea. Also unlike orthopnea, it does not develop immediately upon laying down. Consequently, it would be highly advantageous to provide a non-invasive, convenient sensor that could be comfortably worn by an individual to assist in the identification of changes in respiratory rate and rhythm that may suggest the onset of congestive heart failure, when an individual is active, recumbent or asleep.

Paroxysmal nocturnal dyspnea (PND) is caused by increasing amounts of fluid entering the lung during sleep and filling the small, air-filled sacs in the lung, the alveoli, which are responsible for absorbing oxygen from the atmosphere for exchange with blood. This fluid typically rests in the legs (peripheral edema), causing swelling in the leg tissues during the day when the individual is upright. At night, when recumbent for an extended period, this fluid is reabsorbed, increasing total blood volume and blood pressure, leading to pulmonary hypertension (high blood pressure) in people with underlying left ventricular dysfunction. The pulmonary hypertension leads to the accumulation of fluid in the lungs, or pulmonary edema. Pulmonary edema is swelling and/or fluid accumulation in the lungs. It leads to impaired gas exchange and may cause respiratory failure. It is due to either failure of the heart to remove fluid from the lung circulation ("cardiogenic pulmonary edema"), or due to a direct injury to the lung parenchyma ("noncardiogenic pulmonary edema"). Treatment depends on the cause, but focuses on maximizing respiratory function and removing the cause. It would be highly advantageous to provide a non-invasive, convenient apparatus and sensor that could be comfortably worn by an individual to assist in the identification of changes in fluid in the lungs and alveoli that may suggest the onset of congestive heart failure, when an individual is active, recumbent or asleep.

The right side of the heart pumps blood returned from the tissues to the lungs to exchange $CO_2$ for $O_2$. Hence, failure of the right side leads to congestion of peripheral tissues. This may lead to peripheral edema or anasarca and nocturia (frequent nighttime urination when the fluid from the legs is returned to the bloodstream). Anasarca ("extreme generalized edema") is a medical symptom characterized by widespread swelling of the skin due to effusion of fluid into the extracellular space. In more severe cases, ascites (fluid accumulation in the abdominal cavity) and hepatomegaly (painful enlargement of the liver) may develop.

Heart failure may decompensate easily; this may occur as the result of any intercurrent illness (such as pneumonia), but specifically myocardial infarction (a heart attack), anemia, hyperthyroidism or arrhythmias. These place additional strain on the heart muscle, which may cause symptoms to rapidly worsen. Excessive fluid or salt intake (including intravenous fluids for unrelated indications) and medication that causes fluid retention (such as NSAIDs and thiazolidinediones) may also precipitate decompensation.

5. Respiratory Metrics and Indicators of Other Pathological Conditions

Respiratory events or disturbances may be associated with a number of pathological conditions. Various respiratory metrics will provide indicators of these pathological conditions. For example, Cheyne-Stokes respiration is the waxing and waning of respiration associated with congestive heart failure. Kussmaul breathing is rapid deep breathing associated with diabetic ketoacidosis. Central or obstructive forms of sleep apnea are prevalent in both normal and heart failure populations. Detection of those respiratory events may be useful in monitoring a patient's disease status, selecting treatment and monitoring its effectiveness. It would be highly advantageous to provide a non-invasive, convenient apparatus and sensor that could be comfortably worn by an individual to assist in the identification of these respiratory events or disturbances when an individual is active, ambulatory, recumbent or asleep.

Sleep apnea is a typically chronic condition that can serve as the catalyst for several different pathological conditions. Respiratory disturbances in the form of sleep-related disordered breathing may often go undetected in patients suffering from heart failure or sleep apnea. Nocturnal Cheyne-Stokes respiration, a form of central sleep apnea, occurs frequently in patients with chronic heart failure. The presence of sleep apnea significantly worsens the prognosis for a heart failure patient. A method for determining the cardiac condition of a patient by a cardiac monitor using the variability of a respiration parameter is generally disclosed in U.S. Pat. No. 6,454,719 issued to Greenhut, incorporated herein by reference in its entirety. Characteristics of periodic breathing patterns, such as hyperpnea length, apnea length, and periodic breathing cycle length, are correlated to circulatory delay time, which is inversely correlated with cardiac output. Therefore, recognizing and monitoring the presence of disordered breathing in heart failure patients could provide useful diagnostic and prognostic information. Moreover, detecting respiratory disturbances and extracting specific parameters related to cardiac function could provide valuable information for assessing a patient's cardiac condition and optimizing therapeutic interventions. Consequently, it would be highly beneficial to provide a simple apparatus and sensor capable of noninvasively monitoring respiratory rate, rhythm and periodic events to identify and diagnose conditions during a person's sleep which might be indicative of cardiac complications or disturbances, particularly sleep apnea.

A standard approach for diagnosis of sleep apnea includes polysomnography, which requires the patient to stay overnight in a hospital for observation, in addition to medical history and screening questionnaires. Polysomnography involves monitoring of multiple parameters including electroencephalography, electromyography, electrocardiography, oximetry, airflow, respiratory effort, snoring, body position and blood pressure.

Polysomnography or a controlled sleep study, which can be used to identify sleep apnea, measures a patient's respiratory patterns during a single sleeping period. However, this procedure is expensive and inconvenient for the patient. Furthermore, a physician must actively prescribe the sleep study and therefore must already suspect a sleep-related breathing disorder. Chronic monitoring of respiratory disturbances as an alternative to polysomnography, particularly in heart failure patients who have increased risk of morbidity in the presence of sleep apnea, is desirable for detecting unrecognized and unsuspected sleep-related disordered breathing. Providing a single, simple apparatus and sensor capable of monitoring the majority of these parameters without having to resort to a complex configuration of sensors and without requiring an overnight stay at a hospital would be highly beneficial to patients and would increase the ability of healthcare providers to more readily identify those persons actually suffering from sleep apnea by collecting the necessary data in their own home setting while sleeping in their own bed, while also substantially reducing the costs associated with this diagnosis.

Diabetes is another disease which may be assessed via effective monitoring of respiratory metrics. Diabetic patients can also benefit from continuous monitoring of their pulmonary functionality and performance. For example, diabetic ketoacidosis may be the first symptom to appear in a person with Type I diabetes. Diabetic ketoacidosis develops when blood is more acidic than body tissues due to the accumulation of ketones in the blood when body fat is metabolized for energy in place of glucose reserves when insulin is not available. Persons having Type II diabetes usually develop ketoacidosis only under conditions of severe stress. Recurrent episodes of ketoacidosis in diabetic persons are generally the result of poor compliance with dietary restrictions or self-administered treatments. Kussmaul breathing, characterized by relatively deep breathing, is a common symptom of ketoacidosis. Therefore early detection and monitoring of Kussmaul breathing in diabetic patients may be valuable in the effective control of diabetes. Consequently, providing diabetic patients with a simple, easy-to-use, non-invasive respiratory apparatus and sensor in addition to devices to measure blood glucose may prove highly beneficial in allowing diabetic patients to more adequately control their diabetic conditions to minimize negative symptoms and effects.

Heart failure and lung failure frequently go hand-in-hand, and hence, this condition can be assessed via effective respiratory monitoring. As previously indicated, heart failure typically presents with symptoms of shortness of breath or elevated respiration rate, among other things. Consequently, it would be extremely beneficial to provide persons with a simple, noninvasive apparatus and sensor that could continuously and directly monitor respiratory rate and rhythm in conjunction with the other functional pulmonary metrics to assess the onset and progression of potential congestive heart failure in patients. In particular, it would be extremely advantageous to provide such a device for elderly patients most susceptible to congestive heart failure. Further, it would be highly advantageous to provide such a device for use by persons who have undergone cardiac surgery to continuously monitor respiratory rate and rhythm to provide tangible evidence to the patient that the surgery was successful, thereby reducing anxiety concerning future potential heart failure. It would be still further advantageous to provide such a device that can simultaneously monitor both cardiac and pulmonary rate and rhythm to provide a more meaningful assessment and correlation between changes in either cardiac or pulmonary functionality.

In light of the plethora of pulmonary diseases which may be more competently assessed via the use of an effective respiratory measurement device, and, given the correlation between respiratory function and cardiac health, it would be highly desirable to provide a wearable device that can detect advanced respiratory functions, is non-invasive, does not require surgery for implantation, does not require skin contact, conductive gels or electrode patches, does not require wearing an uncomfortable band wrapped around the chest, is low power without any ionizing radiation, allows long-term continuous patient monitoring in both hospital and ambulatory settings, is safe, allows real-time 24/7 monitoring, and is more affordable than current techniques and devices. It would be further highly desirable to provide such a device capable of simultaneously monitoring both cardiac and respiratory functionality. The present invention is directed to providing the above desired features which have been long sought after by healthcare providers.

SUMMARY OF THE INVENTION

The present invention provides an apparatus and method for non-invasive, instantaneous and continuous measurement of a subject's respiratory rate, rhythm, volume and other functional and physiological pulmonary metrics for the purposes of detecting respiratory trends, events or disturbances related to a pathological condition. The apparatus may be used as a medical diagnostic device or used for non-medical purposes, such as athletic performance monitoring.

In particular, the present invention provides an apparatus and method that is uniquely capable of monitoring each individual lobe of each lung simultaneously. The apparatus is preferably self-contained and used externally. A sensing portion of the apparatus, the "sensor", generates an output signal that varies with the respiration cycle such that a respiration rate, rhythm and optionally other respiration features may be derived or extracted from the sensed signal. The apparatus includes one or more of these sensors placed about the thorax or abdomen of a subject to collect data relevant to respiratory performance and functionality. Each sensor comprises an ultra wide-band radar system having a transmitting and receiving antenna for applying ultra wide-band radio signals to a target area of the subject's anatomy wherein the receiving antenna collects returns from the target area. The received signals are then delivered to a data processing unit such as an integrated processor, a PDA or Personal Computer, having software and hardware used to process the signal returns to generate results indicating respiratory performance or status.

The signal data is provided as an input to one or more physiological assessment algorithms, including a respiratory assessment algorithm. The method of the respiratory assessment algorithm generates relevant measures of respiratory rate, rhythm, tidal volume, and other pulmonary parameters and respiratory events and disturbances. In addition, in one embodiment, the algorithm generates an ongoing and continuous trend of potential congestion or fluid buildup in the lungs themselves by correlating the measured bulk dielectric strength of targeted areas of the lungs to assess and quantify both instantaneous fluid content and changes in fluid content. The apparatus and methods of the invention determine if the data indicates the presence of symptoms associated with various diseases: respiratory, cardiac and others. The algorithms are implemented in the apparatus or in associated external systems and can provide various alerts to caregivers to allow rapid response to serious immediate events, and, can provide trending data for use by a physician to assess changes in a patient's pulmonary performance which may indicate a need for various treatments. The apparatus may be applied in both ambulatory and non-ambulatory settings.

In one aspect of the present invention, an apparatus is provided that includes a control unit, an antenna, and a sensing unit capable of resolving a change in a spatial configuration of a lung during a respiration cycle, and, is capable of measuring respiration rate, rhythm and tidal volume, along with other derivative respiratory metrics.

In another aspect of the present invention, a method is provided that includes receiving a reflected signal originally transmitted from outside a subject's body and directed at the subject's thoracic area and determining a change in a dimension of portions of the lungs during a respiration cycle, based upon the transmitted and reflected signal.

In yet another aspect of the present invention, an apparatus and method is provided that includes an external sensor that transmits signals into a subject's thoracic area to determine changes in dielectric strength of monitored portions of each lung so as to determine if a subject may be progressing toward a congestive state suggesting imminent congestive heart failure.

In a further aspect of the present invention, an apparatus and method is provided that includes multiple sensors which monitor and compare excursion of each individual lobe of each lung so as to determine whether any obstructions exist within associated bracchii. These and other aspects of the present invention are described in additional detail in the remainder of this document. It should be understood, however, that the description herein of specific aspects, versions or embodiments is not intended to limit the invention to the particular forms disclosed, but on the contrary, the intention is to cover all modifications, equivalents, and alternatives falling within the spirit and scope of the invention as defined by the appended claims.

For example, described herein are devices and apparatus for determining a change in the spatial configuration of a lung by interrogating the lung with electromagnetic energy. These devices or apparatus may include: at least one antenna adapted to be located adjacent a portion of the lung; and a sensing unit capable of resolving a change in reflected signals, wherein said sensing unit of the apparatus is capable of resolving a change in reflected signals that are functionally related to a change in respiratory volume.

The apparatus may be configured for location external to the body. In some variations, the sensing unit further comprises: a substrate and at least two antennae mounted to said substrate in a pattern and being capable of both transmitting and receiving radiofrequency signals. The reflected signals may be derivative of an earlier transmitted ultra wide-band signal. The reflected signals may be derivative of an earlier transmitted ultra wide-band signal having a frequency band extending from 3.1 GHz to 10.6 GHz, ensuring compliance with applicable FCC regulations.

The device may be adapted to collect data from at least one lung, or form more than one lung. For example, the apparatus may be adapted to collect said data from a targeted portion of at least one lung. The targeted portion may be any of the upper, middle or lower lobes of at least one lung and said targeted portion is encompassed by an interrogation volume and said interrogation volume encompasses a respiratory chamber.

Also described herein are medical devices for assessing pulmonary functionality comprising: a sensing unit including a control unit, a radar transceiver, and at least one antenna, said at least one antenna being adapted to be located adjacent a portion of a lung to measure dynamic motion of a targeted portion of the lung. The control unit may drive the radar transceiver and the radar transceiver may transmits radiofrequency energy at said targeted portion and said radar transceiver receives reflections from said targeted portion and said at least one antenna couples the radiofrequency energy between said transceiver and said targeted portion.

The sensing unit further comprises software configured to cause said sensing unit to be capable of resolving a change in a spatial configuration of the lung. The change in spatial configuration may be functionally related to a change in lung volume.

In some variations, the sensing unit further comprises: a substrate; said at least one antenna mounted to said substrate and being capable of sensing a reflected signal; and a plurality of conductors extending from said at least one antenna and electrically coupled with said control unit. The sensing unit may further comprise: a substrate; at least two antennae mounted to said substrate in a pattern and being capable of sensing reflected signals received by said at least two antennae; and a plurality of conductors extending from said at least two antennae and electrically coupled with said sensing unit.

The at least one antenna may be adapted to be located on a subject's chest adjacent a portion of at least one lung. The at least one antenna may be adapted to be located in close proximity to the sternum within a three centimeter radius of a center of the sternum so as to simultaneously collect reflected signals caused by the beating of the heart and internal movement derivative of respiration.

Also described herein are non-invasive systems for determining dynamic physiologic and structural anatomic data from a subject comprising an ultra wide-band radar system having at least one transmitting antenna and at least one receiving antenna for applying ultra wide-band signals to a target area of the subject's anatomy adjacent the lungs wherein said receiving antenna collects and transmits signal returns from said target area which are then delivered to a data processing and control unit having software and hardware used to process said signal returns to produce a value for said dynamic physiologic and structural anatomic data concerning behavior of the lungs.

The ultra wide-band signals may be transmitted in a manner compliant with FCC regulations in a frequency spectrum from 3.1 GHz to 10.6 GHz. The dynamic physiologic and structural anatomic data is related to respiratory function. The dynamic physiologic and structural anatomic data may be related to a change in the spatial configuration of at least one lung. The dynamic physiologic and structural anatomic data may be related to a change in the spatial configuration of at least one lobe of at least one lung. The dynamic physiologic and structural anatomic data may be related to respiratory function and provides an assessment of changes in any of respiratory rate, respiratory rhythm, and tidal volume. The dynamic physiologic and structural anatomic data may be related to respiratory function and provides a quantitative assessment of lung volume and respiratory output.

Also described herein are methods for determining changes in respiratory volume in a body wherein an ultra wide-band medical radar transceiver, including a transmitter and a receiver and a signal processor integrated with software elements in conjunction with a central processing unit are used according to the following steps: said transceiver transmits a series of extremely short duration electromagnetic pulses into a body, said electromagnetic impulses encounter a boundary between different biological substances in the body, small amounts of incident energy encountering the boundary are reflected back towards said receiver as raw reflections where said raw reflections are captured and pre-processed by said receiver, said receiver captures a plurality of said raw reflections using a high speed sample and hold circuit where capture time for a sample of said raw reflections is set equal to a round trip time of flight from said transmitter to a depth range of interest and back to said receiver, said plurality of sampled reflections from said depth ranges of interest are integrated to form an integrated signal to minimize high frequency noise so as to avoid corruption of desired data related to tracking instantaneous respiratory chamber volume, said integrated signal is amplified and passed through a low-pass filter to prevent signal aliasing prior to digitization, a predetermined number of reflections for a first range of interest are collected and integrated, said receiver sample timing is changed and reflections from a next range of interest are captured, said above steps are repeated until reflections from an entire range of interest across the respiratory chamber are collected, said above step is then continually repeated to deliver an updated instantaneous measure of respiratory volumetric changes.

The boundaries within a target range of interest may move with respect to placement of said transceiver's antenna, producing a complex series of time-varying reflections, and wherein said complex series of time-varying reflections are continually processed by said signal processor to extract information on the mechanical activity of at least one lung.

The signal processor and central processing unit may provide calculation of respiratory chamber volume via the additional steps of: said digitized radar reflections are first range aligned on sweep boundaries and passed through a series of high pass filters to minimize low frequency noise and static clutter, resultant data associated with all anatomical motion in said range of interest is amplified and coarse quantized using a binary quantizer where the quantizer threshold for a given sweep or row is based on the median value of the data set, resulting in an intermediate black and white image, said intermediate image is further refined through the application of a series of one or more 1-dimensional or 2-dimensional filters to reduce noise to remove random speckle noise and increase the sharpness of the image boundary edges, supporting accurate determinate of spatial change, and, thereby presenting an image space full of various spatial structures changing in time that represent both lung wall motion and various noise sources including organs, bones, and stray radiofrequency emissions.

The data may be further refined via the application of at least one additional metric to delineate and confirm that the structures found in the image are lung wall excursions and not caused by unrelated signal sources.

The at least one additional metric is respiratory rate wherein the respiratory rate is integrated within said signal processor and is detected via application and processing of the UWBMR signals, said signal processor calculating the respiratory rate via conversion of an entire swept image space to a predetermined frequency domain using an algorithm, wherein said algorithm identifies and isolates an image region of the swept range containing the strongest respiratory signal, while simultaneously determining a range of depth containing the targeted respiratory motion for use in determining one or more additional metrics.

The method may also include the steps of: wherein said at least one additional metric is identification and verification of completeness of a target respiratory structure as the respiratory structure changes over time, by evaluating the sustained and rhythmic behavior of the respiration-influenced anatomical elements, wherein the IRV identifies qualifying signals for further analysis by capturing and prioritizing those said qualifying signals with respect to minimum discontinuities, and wherein a conversion process includes a chain coding technique in conjunction with at least one structural morphological technique to minimize signal discontinuities caused by noise loss.

The method may further include: wherein said at least one additional metric is the continual and repeated identification and tracking of a respiratory-like motion characteristic in the candidate image space, wherein said respiratory-like motion characteristic best characterizes the approximate motion of the anterior and posterior respiratory chamber walls through time, and, wherein a corollary component of said identification and tracking of said respiratory-like motion characteristic is the isolation and avoidance of signals having a non-respiratory-like motion characteristic, wherein said non-respiratory-like motion signals indicate the likely presence of a non-respiratory signal source.

The method may further include: wherein said at least one additional metric is the development of a correlation between the time-domain characteristics of the isolated respiratory range bin identified by a first respiratory rate metric with points identified in the image space that represent minimum, maximum, and zero-crossing points of respiratory wall excursions in the image space as identified by a second and a third metric.

The method may also include: wherein said data is further refined via the application of at least one additional metric to delineate and confirm that the structures found in the image are respiratory wall excursions and not caused by other signal sources, and wherein image regions that meet the requirements of the at least one additional metric are isolated and identified as qualifying candidates for further analysis, wherein the likely image region providing a most probable representation of the instantaneous respiratory volume is the image region having the strongest characteristic in said at least one additional metric.

The method may also include: wherein the likely image region is chosen, minimum and maximum respiratory wall excursions are identified and quantified using prior data acquired and already available from the assessment of at least one additional metric, wherein the actual chamber wall displacement is calculated using minimum and maximum respiratory wall excursions by counting spatial pixels traversed from a minimum point to a maximum point of a respiratory waveform to determine a count of spatial pixels traversed and multiplying said count of pixels by a resolution of the data capture device.

The instantaneous respiratory volume may be determined by the additional step of applying presumed dimensions of the respiratory chamber in conjunction with said minimum and maximum respiratory wall excursions to determine volumetric changes in the respiratory chamber.

The presumed dimensions of the respiratory chamber may be represented by one or more different shapes, wherein said shapes determine the accuracy of the calculated respiratory chamber volume and the derivative tidal volume.

The one or more different shapes is a simple elongated rectangular box having dimensions approximating dimensions of a lung. The one or more different shapes is an asymmetric changing ellipsoid.

The one or more different shapes may be the actual shape of said respiratory chamber as determined by other precursor imaging and sizing methods, including any of x-ray, magnetic resonance imaging, ultrasound, surgery or other similar methods capable of determining the dimensions of said respiratory chamber.

The one or more respiratory performance parameters may be determined. The one or more respiratory performance parameters may include tidal volume, said tidal volume calculated by taking the difference between said maximum and said minimum respiratory chamber volume over a single respiration cycle. The one or more respiratory performance parameters may be respiratory output, said respiratory output calculated by multiplying said tidal volume by the respiratory rate. The one or more respiratory performance parameters may be respiratory efficiency, said respiratory efficiency calculated by dividing said tidal volume by a maximum respiratory chamber volume.

Also described herein are non-invasive systems for determining dynamic physiologic and structural anatomic data from a subject comprising an ultra wide-band radar system having a transmitting and receiving antenna for applying ultra wide-band signals to a target area of a subject's anatomy wherein said receiving antenna collects signal returns from the target area which are then delivered to a data processing and control unit having software and hardware used to process said signal returns to produce a value for respiratory tidal volume and changes in respiratory tidal volume supporting multiple diagnostic requirements.

The ultra wide-band radar system may comprises a transceiver having an impulse transmitter and a swept-range receiver wherein said transmitter generates a series of ultra wide-band pulses and said receiver captures resulting reflections across a target range of interest and a signal processor operates on said range-dependent reflections to extract desired data. The target range of interest may be located in a chest cavity, including at least one respiratory chamber. The desired data may be instantaneous respiratory chamber volume. The desired data may be tidal volume.

Also described herein are methods for detecting a respiratory disturbance, comprising: sensing a physiological signal containing a frequency or an amplitude component related to at least two respiratory cycles; deriving at least one respiratory parameter from the physiologic signal; and detecting a respiratory disturbance event when the at least one respiratory parameter meets or exceeds a predetermined criteria threshold for detecting the respiratory disturbance.

The method may also include measuring the magnitude of a characteristic of the respiratory disturbance. A measure of the respiratory disturbance may be at least a one of: apnea duration; hypopnea duration; hyperpnea duration; a periodic breathing cycle length; a dielectric value. The physiological signal may be a UWB signal indicating at least a one of: respiratory rate, respiratory rhythm, tidal volume, blood pressure, patient motion, patient inactivity, cardiac rate, cardiac rhythm, and, respiratory dielectric.

The respiratory disturbance may comprise Kussmaul breathing. The respiratory disturbance may be Cheyne-Stokes respiration. The respiratory disturbance is sleep apnea. The respiratory disturbance is indicative of the onset of congestive heart failure.

The method may also include a step of determining an estimate of cardiac function based on a metric of the respiratory disturbance. The method may also include a step of triggering the storage of physiological data upon the detection of the respiratory disturbance. The method may also include a step of triggering a therapy based at least in part upon detection of the respiratory disturbance. The method may also include a step of generating a warning to alert a clinician or a patient upon detection of the respiratory disturbance.

Also described herein is a device for detecting a respiratory disturbance, comprising: means for sensing a physiological signal containing a frequency component or an amplitude component related to a common characteristic of at least two respiratory cycles; means for deriving at least one respiratory parameter from the physiologic signal; and means for detecting a respiratory disturbance event when the at least one respiratory parameter meets or exceeds a predetermined criteria threshold for detecting the respiratory disturbance.

Also described herein is a computer readable medium for storing a set of computer instructions for performing the following method: instructions for sensing a physiological signal containing a frequency component or an amplitude component related to a common characteristic of at least two respiratory cycles; instructions for deriving at least one respiratory parameter from the physiologic signal; and instructions for detecting a respiratory disturbance event when the at least one respiratory parameter meets or exceeds a predetermined criteria threshold for detecting the respiratory disturbance.

The computer-readable medium may also include instructions for measuring the magnitude of a characteristic of the respiratory disturbance. A measure of the respiratory disturbance may be at least a one of: apnea duration; hypopnea duration; hyperpnea duration; a periodic breathing cycle length; respiratory dielectric congestion duration.

The physiological signal may be at least a one of: respiratory rate; respiratory rhythm; tidal volume; blood pressure; patient motion; patient inactivity; cardiac rate; cardiac rhythm; respiratory dielectric; an oxygen saturation measurement.

The respiratory disturbance may comprise Kussmaul breathing, a Cheyne-Stokes respiration event, a sleep apnea event, a heart failure event, a congestive heart failure event, or the like.

The method (or computer readable medium) may also include a step of instructions determining an estimate of cardiac function based on a metric of the respiratory disturbance; and/or instructions for triggering the storage of a physiological data item upon the detection of the respiratory disturbance; and/or instructions for triggering a therapy based at least in part upon detection of the respiratory disturbance; and/or instructions for generating a warning to alert a clinician or a patient of the detection of the respiratory disturbance; and/or instructions for determining a heart failure status of a patient in the event that the estimate of cardiac function is lower than a predetermined lower threshold.

BRIEF DESCRIPTION OF THE DRAWINGS

For fuller understanding of the present invention, reference is made to the accompanying drawings numbered below. Where reference numbers are provided, commonly used reference numbers identify the same or equivalent parts of the claimed invention throughout the several figures.

FIG. 36 is a table comparing basic correlated dielectric strength in normal and congested lungs, according to an embodiment of the invention;

FIG. 37 is a table illustrating progressive dielectric strength across four congestive states, according to an embodiment of the invention;

FIG. 38 is a table illustrating progressive dielectric strength across four states using multi-lobe sensors, according to an embodiment of the invention;

FIG. 39 is a table derived from the table of FIG. 38, measured at full inspiration only, according to an embodiment of the invention;

Figure 1:
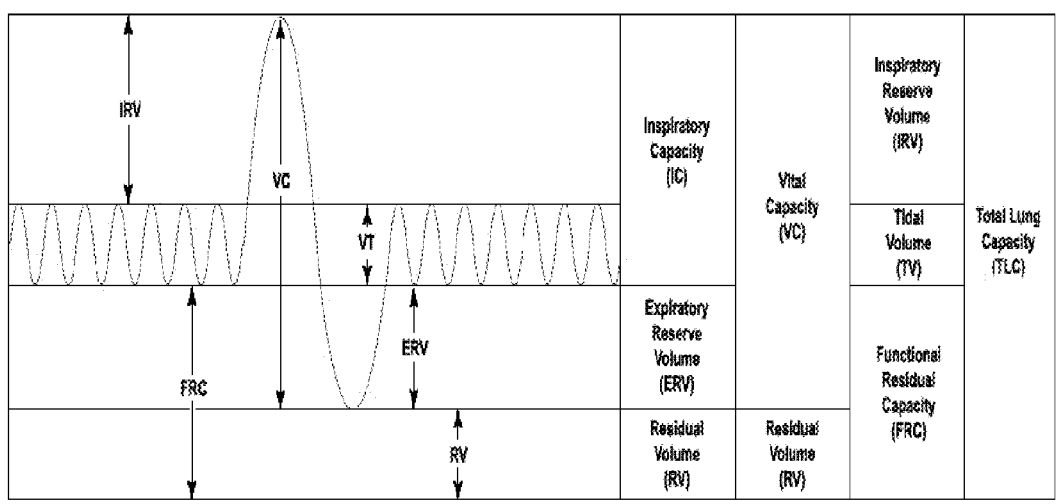
FIG. 1 is a chart illustrating the relationship between various respiratory metrics as measured by various embodiments according to the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DESCRIPTION OF ILLUSTRATIVE EMBODIMENTS

The reader is notified that the techniques described in this paper are examples only. The description is drawn to particular embodiments, versions or aspects of the present invention. Those embodiments, versions or aspects, however, should not be read as limiting the scope of the invention. The invention is defined legally by the claims that issue. For example, claims may not include all the features described in conjunction with an embodiment; in that case, the claim is broader than the embodiment. Likewise, claims may include different combinations from different embodiments. Those having ordinary skill in the art will recognize that changes can be made to the embodiments listed here without departing from the spirit and scope of the disclosure and the spirit, scope, and legal coverage of the claims.

Illustrative embodiments of the invention are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming and capital-intensive but would nevertheless be a routine undertaking for those of ordinary skill in the art having the benefit of this disclosure. Now, in greater detail, embodiments of the apparatuses and methods comprising the present invention are described.

Different embodiments of this disclosure involve the following concepts: (1) anatomical element movement measurement using single or multiple sensors or sensor arrays; (2) anatomical element movement detection using a single sensor; (3) respiratory chamber interrogation using a single sensor; (4) respiratory chamber interrogation using multiple sensors or sensor arrays; (5) respiration rate and rhythm determination via measurement of diaphragmatic movement using a single sensor; (6) respiration rate and rhythm determination using a chest-centric single sensor; (7) wireless sensor array deployed in an article of clothing; (8) wired sensor array; (9) hybrid wireless/wired sensor array; (10) linear sensor arrays; (11) obstruction location determination using a multi-lobe sensor array; (12) variable adaptive lung models and algorithms; (12) sensors to support concurrent cardiac and pulmonary assessment; (13) sensor targeting functionality; (14) adaptive modeling and simulations methods; (15) instantaneous respiratory volume modeling and methods; (16) adaptive software user interfaces; (17) congestive heart failure progression using a multi-lobe sensor array to track relative dielectric values; (18) methods for assessing respiratory chamber excursion distance; (19) methods for identifying and responding to respiratory disturbances or events; and, (20) methods for performing parameter measurement cross-checks to confirm sensor operation and calibration.

1. Anatomical Element Movement Measurement Using Multiple Sensors or Sensor Arrays The present invention uses electromagnetic energy in the form of unique radiofrequency waveforms to acquire signals indicating certain respiratory metrics or parameters. In particular, the present invention measures internal mechanical movement and dielectric strength to measure and assess various respiratory parameters.

Embodiments of the present invention provide for determining pulmonary functionality and, thus, for assisting in identifying symptoms and delivering solutions for problems associated with pulmonary functionality. The present invention supports the provision of various responses by caregivers to modify a subject's respiratory behavior or performance. The present invention provides information which may comprise part of a treatment protocol to support a decision to initiate or make a change in medications to a subject to alter respiratory function or to treat another disease which is suspected as the proximate cause of the abnormal respiratory behavior. Moreover, the present invention provides information supporting a decision to perform surgery on a subject to rectify a critical respiratory condition, or, other conditions which may be the proximate cause of respiratory deficiencies, such as congestive heart failure.

FIG. 1 is a chart illustrating the relationship of various parameters and metrics associated with a respiratory cycle. The present invention analyzes and processes measured reflected ultra-wideband (UWB) signals to generate data used to determine the value of these various parameters and metrics for a monitored subject. These metrics include, at a minimum, respiratory rate and rhythm. Tidal volume and other metrics can be derived from the signals received by the apparatus of the present invention.

Figure 2:
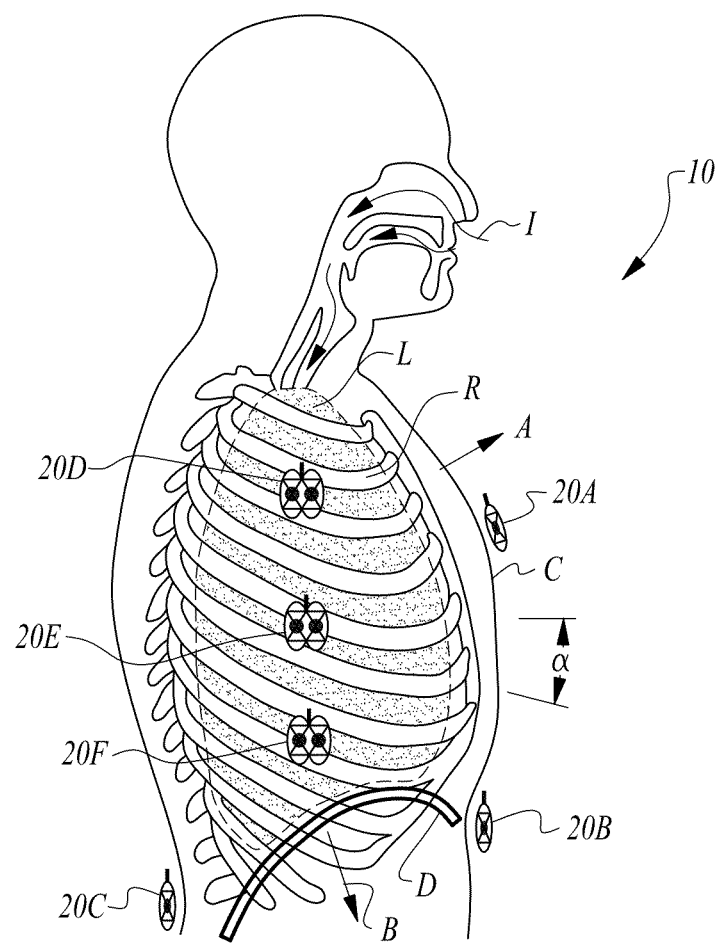
FIGS. 2 and 3 are illustrations of a multi-sensor version of the apparatus directed toward measuring respiratory-influenced anatomical movement according to the present invention.
Figure 3:
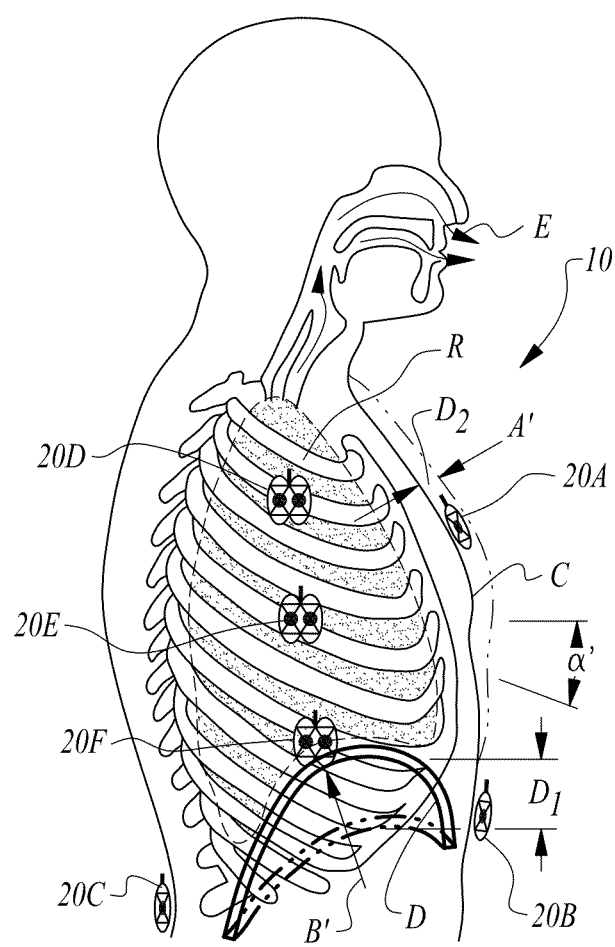

In a first embodiment, as illustrated in FIGS. 2 and 3, the apparatus 10 of the present invention captures and measures the motion of multiple anatomical elements during a respiratory cycle, where the motion is induced by various types of breathing. One or more sensors 20 transmit signals toward target areas and capture reflected signals which are then processed by the sensor to develop a qualitative and quantitative assessment of respiratory performance and health. To understand the operation of the apparatus 10 of the present invention, it is helpful for the reader to understand fundamental aspects of the physiological mechanics of breathing and how the apparatus 10 uniquely evaluates and tracks movement of the anatomical structure to generate various relevant respiratory parameters or metrics. The subsequent discussion of breathing mechanics, taken in conjunction with the respiratory disease information provided in the Background section of this document, will provide an understanding of both the operation of the apparatus 10 of the present invention and how the apparatus 10 figures prominently and uniquely in the assessment of the various disease states and respiratory performance.

FIGS. 2 and 3 provide an illustration of the key anatomical elements involved in a respiratory cycle, including inspiration and expiration respectively. In addition, FIGS. 2 and 3 illustrate a first embodiment of the apparatus 10 of the present invention comprising the placement of a plurality of sensors 20 about an individual's chest, abdomen and back to measure the actual anatomical mechanical movement and displacement of anatomical elements that come into play during respiration. The presence and integration of multiple sensors 20 will allow the apparatus to track and monitor movement of a plurality of anatomical elements, and, to integrate the measurement of the movement of those elements into an overall assessment of respiratory performance.

In a first embodiment, the apparatus 10 is suited to tracking at least three primary types of breathing: (1) chest (or costal—meaning "of the ribs"); (2) abdominal (diaphragmatic); and, (3) clavicular. In this first embodiment, the apparatus 10 of the present invention primarily measures physiological parameters and anatomical motion associated with the first two primary types of breathing: chest and abdominal breathing. The third primary type, clavicular breathing, characterized by shoulder movement, generally only comes into play when a person is taking a maximum breath. Although the apparatus 10 is not, in the present configuration, intended to track or measure shoulder movement, any assistance provided by clavicular breathing is reflected in the motion of anatomical elements associated with chest and abdominal breathing. Consequently, the apparatus 10 is able to also identify presence of clavicular breathing by detection of changes in the motion of anatomical elements associated with chest and abdominal breathing. In a derivative embodiment to measure clavicular motion, additional sensors may be positioned slightly higher to directly measure motion of the clavicle.

Now, in greater detail, referencing FIGS. 2 and 3, the apparatus 10 comprises one or more sensors 20A through 20F deployed about a subject's upper body, including the thorax and abdomen, to measure mechanical motion of anatomic elements or physiological function associated with respiration. Chest or costal breathing during inspiration I, as illustrated in FIG. 2, is primarily characterized by an outward, upward movement A of the chest wall C. Sensor 20A, preferably located adjacent the midpoint of a subject's sternum, is positioned to continuously measure this type of movement. Simultaneously, the diaphragm D moves in a downward direction B, expanding the volume within the chest cavity and allowing the lungs L to expand, creating a lower pressure within the lungs L and causing air to be inhaled I. Movement of the diaphragm D is monitored by sensors 20B and 20C. Additionally, ribs R elevate and swing upward an angular distance α. This angular rotation of the ribs is monitored by sensors 20D, 20E and 20F.

During expiration, as illustrated in FIG. 3, chest breathing is characterized by an inward and downward movement A' of the chest wall C for a distance D2, along with a corresponding upward expansion of the diaphragm D for a distance D1, causing a greater pressure in the lungs then the external ambient pressure and causing exchanged carbon dioxide in the lungs L to be expired E. Additionally, during expiration E, the ribs R swing downward an angular distance α'.

In chest breathing, expansion of the upper torso is generally centered at the midpoint of the chest C; it therefore tends to aerate the middle part or lobe of each lung L most. Sensor 20A is preferably positioned adjacent the midpoint of the sternum to track the motion of the chest wall C and to sense the aeration of the middle part of each lung L. The lower lobe of each lung L is most abundantly perfused with blood; consequently, the effort associated with chest breathing creates a ventilation/perfusion mismatch. Thus, during resting periods, chest breathing is less efficient than abdominal breathing since abdominal breathing will tend to aerate the lower lobe having the greatest concentration of blood perfused throughout the lung tissue. Subsequent described embodiments of the present invention include sensors 20 which detect and measure this ventilation/perfusion mismatch by directly tracking the dielectric value of each lobe of each lung L.

The apparatus 10 of the present invention is uniquely suited to continually monitoring respiratory function of a subject to provide qualitative measures of that subject's mental or emotional state. For example, chest breathing, as compared to abdominal breathing, requires more work to be done in lifting the rib cage, thus the body must work harder to accomplish the same blood/gas mixing than with abdominal breathing. The greater the work expended to breathe, the greater the amount of oxygen needed, which necessarily results in more frequent breaths. Chest breathing is useful during vigorous exercise but generally does not come into play for ordinary, everyday activity. Since it is part and parcel of the fight or flight response, it occurs when the individual is aroused by external or internal challenges or danger. Additionally chest breathing or the absence thereof may be precipitated by the ingestion of various stimulants or depressants, indicating that an individual has taken some form of drug or consumed alcohol. As a result, chest breathing is likely to be associated with other symptoms of arousal like tension and anxiety. Since there is a reciprocal relationship between breathing and the mind, chest breathing, if continued during rest periods, will lead to tension and anxiety, thus creating a vicious circle. With chest breathing, the breath is likely to be shallow, jerky and unsteady, resulting in unsteadiness of the mind and emotions. Until chest breathing is replaced by deep, even and steady abdominal breathing, efforts to relax the body, nerves and mind will be less effective. The apparatus 10 of the present invention provides an individual with a simple, noninvasive apparatus 10 and one or more sensors 20 to distinguish chest breathing from abdominal breathing for diagnostic, biofeedback, drug/alcohol monitoring and other purposes.

With further reference to FIG. 2, abdominal or diaphragmatic breathing is characterized by downward contraction B of the diaphragm muscles D during inspiration I and by upward expansion B' of the diaphragm muscles D during expiration E. The diaphragm D, the principal muscle involved in abdominal breathing, is a strong dome-shaped sheet of muscle that separates the chest cavity from the abdomen. When we breathe in, the diaphragm D contracts and pushes downwards in a general direction B, causing the frontal abdominal muscles to relax and rise. In this position, the lungs L expand, creating a partial vacuum, which allows air to be drawn in. When we breathe out, the diaphragm D relaxes and moves upward in a general direction B', the abdominal muscles contract and air containing exchanged carbon dioxide is then expelled from the lungs L. Studies indicate that the diaphragm D travels a small distance D1 of only 1 to 2 cm during a typical respiration cycle. Sensors 20B and 20C are positioned so as to track the movement of the diaphragm D during a respiratory cycle. Sensor 20B is generally located at the front of the stomach at the waist level, supporting tracking of the movement of the forward or anterior portion of the diaphragm D; sensor 20C is located adjacent the small of the back, supporting tracking of the movement of the rear or posterior portion of the diaphragm D.

Of the two major types of breathing, abdominal breathing is considered the most efficient because greater expansion and ventilation occurs in the lower part of the lung L where the blood perfusion is greatest. In children and infants, the diaphragm D is effectively the sole muscle for respiration, so watching an infant breathing provides a good illustration of what abdominal breathing is like. As the diaphragm D contracts, it also pushes the abdominal organs downwards and forwards, and this rhythmical massage gently compresses the organs and improves circulation. Abdominal breathing in conjunction with physical and mental relaxation has been found to reduce high blood pressure and anxiety. Consequently, the apparatus 10 of the present invention may be used to provide a biofeedback solution to train an at-risk individual to focus on abdominal breathing whenever high blood pressure or general anxiety is present.

Assessing the type of breathing can qualitatively determine a person's mental and physical state. When an individual is calm and composed, the breathing is typically abdominal. Since there is a reciprocal relationship between breathing and the mind, practicing abdominal breathing leads to mental relaxation. Consequently, abdominal breathing is an important tool available for stress management. It promotes a natural, even movement of breath which calms the nervous system and relaxes the body. Abdominal breathing is the most efficient method of breathing, using minimum effort for maximum oxygen. Abdominal breathing provides the body with sufficient oxygen, expels carbon dioxide adequately, relaxes the body and the mind, and, improves circulation to the abdominal organs. The apparatus 10 of the present invention comprising sensors 20 provides a noninvasive and nonintrusive, wearable respiration monitoring apparatus 10 to distinguish chest breathing from abdominal breathing. This information may be used for diagnostic, biofeedback and other purposes.

As previously indicated, calavicular breathing is only significant when maximum air is needed, such as during exercise. The name is derived from the motion of the two clavicles or collar bones which are pulled up slightly at the end of maximum inhalation, expanding the very top of the lungs L. It comes into play when the body's need for oxygen is very great. This type of breathing can be seen in patients with asthma or chronic bronchitis. The present invention provides a noninvasive, nonintrusive, wearable respiration monitoring apparatus 10 to distinguish clavicular breathing from chest breathing and abdominal breathing. Upper sensors 20D may be targeted toward monitoring and measurement of movement of the clavicles to identify when a person is experiencing clavicular breathing. This information may be used for diagnostic and other purposes.

Now, in greater detail, as illustrated in FIGS. 2 and 3, sensors 20D, 20E and 20F are preferably positioned at locations along the side of one's chest C to track muscular and skeletal movement during a respiratory cycle. In particular, the sensors 20D, 20E and 20F track the cyclical movement of the rib structures R to assess breathing activity, particularly, respiratory rate and rhythm. In quiet respiration, the first and second pairs of ribs are fixed by the resistance of the cervical structures; the last pair, and through it the eleventh, by the quadratus lumborum. The other ribs are elevated, so that the first two intercostal spaces are diminished while the others are increased in width. Elevation of the third, fourth, fifth, and sixth ribs leads to an increase in the antero-posterior and transverse diameters of the thorax; the vertical diameter is increased by the descent in a general direction B of the diaphragmatic dome D so that the lungs L are expanded in all directions except backward and upward. Elevation of the eighth, ninth, and tenth ribs is accompanied by a lateral and backward movement, leading to an increase in the transverse diameter of the upper part of the abdomen; the elasticity of the anterior abdominal wall allows a slight increase in the antero-posterior diameter of this part, and in this way the decrease in the vertical diameter of the abdomen is compensated and space provided for its displaced viscera. Expiration is effected by the elastic recoil of its walls and by the action of the abdominal muscles, which push back the viscera displaced downward by the diaphragm D. The sensors 20 of the apparatus 10 deployed about an individuals upper torso capture reflections associated with the above movements. These reflections are then processed to create a measure of respiratory rate and rhythm, along with measurement of the change in respiratory volume during a respiration cycle.

With continued reference to FIGS. 2 and 3, during deep respiration, all the movements of quiet respiration also occur during deep respiration, but to a greater extent. Hence, the apparatus 10 of the present invention distinguishes quiet respiration from deep respiration by measuring the increased movement of the anatomical elements. In deep inspiration I, the shoulders and the vertebral borders of the scapulae are fixed and the limb muscles, trapezius, serratus anterior, pectorales, and latissimus dorsi, are called into play. The scaleni are in strong action, and the sternocleidomastoidei also assist when the head is fixed by drawing up the sternum and by fixing the clavicles. The first rib is therefore no longer stationary, but, with the sternum, is raised; with it all the other ribs except the last are raised to a higher level. In conjunction with the increased descent in a general direction B of the diaphragm D, this provides for a considerable augmentation of all the thoracic diameters which is measured by all sensors 20 from different perspectives. The anterior abdominal muscles come into action so that the umbilicus is drawn upward and backward, but this allows the diaphragm D to exert a more powerful influence on the lower ribs; the transverse diameter of the upper part of the abdomen is greatly increased and the subcostal angle α opened out. The deeper muscles of the back, including the serrati posteriores superiores and the sacrospinales and their continuations, are also brought into action; the thoracic curve of the vertebral column is partially straightened, and the whole column, above the lower lumbar vertebrae, drawn backward. This increases the antero-posterior diameters of the thorax and upper part of the abdomen and widens the intercostal spaces. Deep expiration E is effected by the recoil of the walls and by the contraction of the antero-lateral muscles of the abdominal wall, and the serrati posteriores inferiores and transversus thoracis. The apparatus 10 captures this increased movement to identify that an individual is in deep respiration. Derivative embodiments of the present invention include additional sensors 20 placed at strategic locations along an individual's back to monitor the movement of anatomical elements in the person's back which contribute additional data which is processed and analyzed by the apparatus 10.

2. Single Sensor Interrogation and Assessment of Target Area

Figure 4:
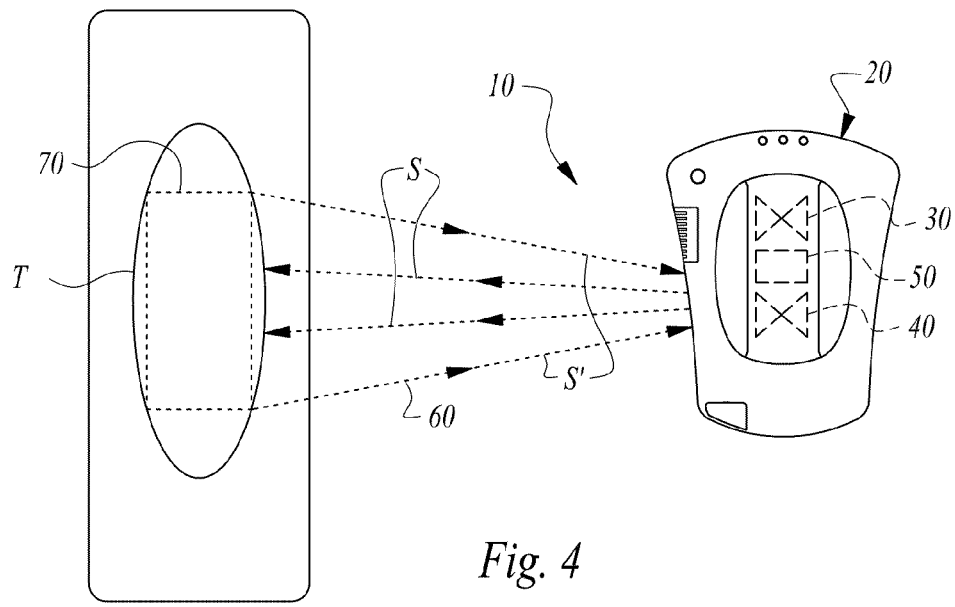
FIG. 4 is an illustration of basic operation of the apparatus according to the present invention.

FIG. 4 is an illustration of the basic operation of the apparatus 10 of the present invention. The apparatus 10 comprises at least one sensor 20 having a transmit antenna 30 and a receive antenna 40. A respiratory sensor module 50 controls the signals S transmitted by the transmit antenna 30. The respiratory sensor module 50 causes the transmit antenna 30 to transmit electromagnetic energy in the form of an ultra-wideband radiofrequency signal S toward a target area T. The transmitted signals S form an interrogation volume 60 which encompass a respiratory chamber of interest 70. A portion of the transmitted electromagnetic energy is reflected by the target area T and the reflections S' are then received by the receiving antenna 40. The received reflected electromagnetic signals S' are then processed by the respiratory sensor module 50.

Figure 5:
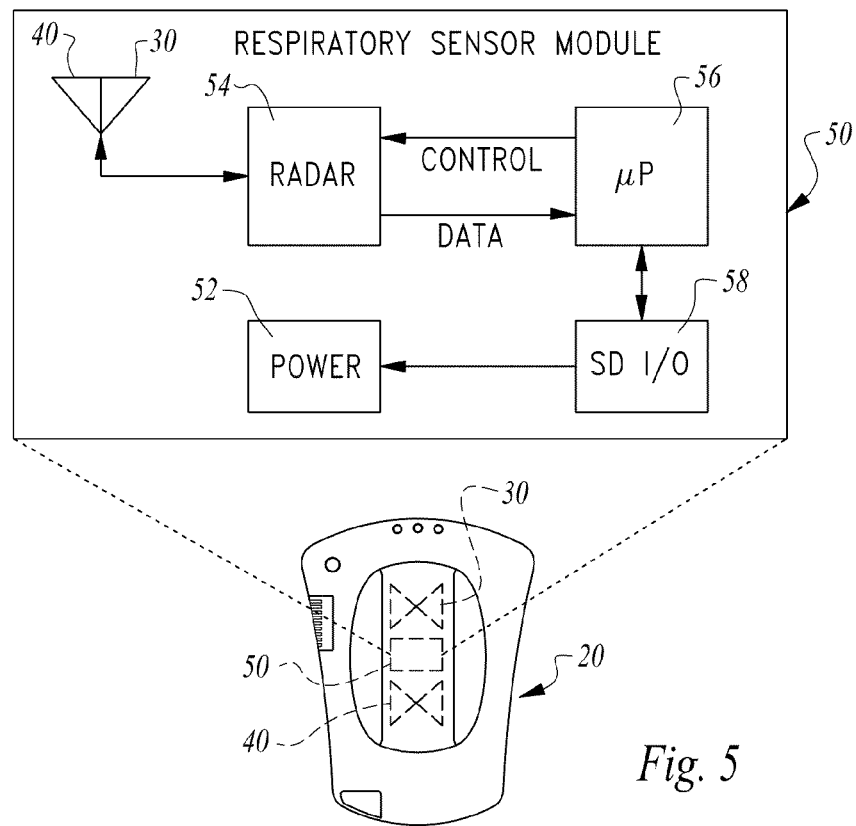
FIG. 5 is a block diagram of primary components of the apparatus, according to the present invention.
Figure 6:
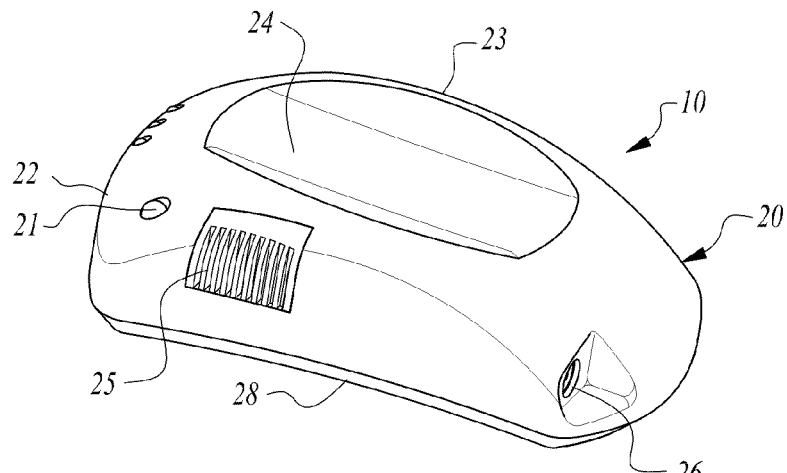
FIG. 6 is a perspective view of a single sensor version of the apparatus, according to the present invention.

FIG. 5 is a simplified block diagram of the respiratory sensor module 50 of the sensor 20. The respiratory sensor module 50 comprises a power module 52 supporting an ultra-wideband medical radar module (UWBMR) 54 for transmitting and receiving ultra-wideband radio signals to interrogate a target area T of interest. The UWBMR 54 coordinates signal delivery and reception via the transmit antenna 30 and receive antenna 40. A microprocessor control module 56 manages the signals S transmitted by the UWBMR 54 and receives and processes the signals S' delivered by the UWBMR 54 which have been collected via the receive antenna 40. A digital input/output module 58 delivers the processed signals from the microprocessor control module 56 to external devices (not shown) for storage, reporting or further processing. The input/output module 58 also delivers instructions to trigger various alarms intrinsic to the sensor 20 for local announcement of certain conditions to a user or caregiver.

Now, in greater detail, in a preferred embodiment, the apparatus 10 of the present invention comprises an active imaging technology composed of three primary elements, an respiratory sensor 20, a transmitter 30, a receiver 40, and, a respiratory sensor module 50. The respiratory sensor module 50 comprises hardware and software elements integrated to provide a stand-alone configuration. An ultra-wideband medical radar component (UWBMR) 54 drives the delivery and reception of radiofrequency signals S, S'. The microprocessor 56, and, one or more proprietary algorithms, cooperate to drive the UWBMR 54 and measure, track and display instantaneous and trended respiratory function and events. The sensor 20 in one configuration comprises a low-PRF (pulse repetition frequency) transmitter 30 and a swept-range receiver 40 where the transmitter 30 generates a series of UWB pulses S and the receiver 40 captures the resulting reflections S' from across a target range of interest T, such as across a patient's chest cavity, including one or more respiratory chambers 70. In another configuration, the transmitter 30 comprises an impulse transmitter. The signal processor 56 operates on the range-dependent reflections S' to extract desired data, including instantaneous respiratory chamber volume and its derivative metrics including tidal volume, respiratory output, and derivative respiratory rate and rhythm.

As shown in FIG. 4, in one version, the apparatus 10 comprises an integrated device consisting of a sensor 20 having a transmitting antenna 30 and a receiving antenna 40. The sensor 20 further includes a respiratory sensor module 50 which can be programmed to address specific ailments or respiratory conditions. This architecture allows a medic to use a single base device 20 with a variety of dedicated modules for specific medical applications. The apparatus 10 of the present invention supports the deployment of a low-cost sensor 20 based upon UWB signals integrated with a respiratory sensor module 50 with advanced software capable of displaying respiratory function results to a user. The respiratory sensor module 50 is preferably integrated within the sensor 20, but may also be connected to the sensor 20 through an expansion bus port on the sensor 20. The expansion bus port is an industry standard input/output interface that allows compliant devices to work with the sensor 20. To minimize processor loading on the sensor 20, the external respiratory sensor module 50 will contain a dedicated embedded processor 56 responsible for controlling the UWB radar 54 and processing received data. In another version, a self-contained respiratory sensor module 50 includes a wireless telecommunications module capable of transmitting continuous data to other sites, or, sending alerts or alarms to entities whenever a suspicious condition is detected by the apparatus 10.

3. Single Sensor Housing and Component Configuration

FIGS. 6-9 are illustrations of a preferred embodiment of the sensor 20. The sensor 20 is comprised of a plastic casing 22 to house the hardware components of the apparatus 10. The housing 22 of the sensor will rest comfortably on a subject's chest and fit comfortably in the hand of a caregiver, while the caregiver is using the sensor 20 to monitor a patient's condition. As illustrated in FIG. 4 and FIG. 5, the casing 22 houses antennas 30, 40 and respiratory sensor module 50. The casing 22 includes a top portion 23 having a concave recess 24 for receiving a strap for securing the sensor 20 to an individual's torso. The casing 22 includes slots 25 for emitting an audible acoustic signal to alert a user of the apparatus 10 of certain events or trends. A data and power port 26 is provided in the casing 22 of the sensor 20. An off/on light 21 is provided to notify a user when the sensor 20 is operational and power is being supplied to the components. The sensor 20 includes a bottom 28 of the casing 22.

Figure 7:
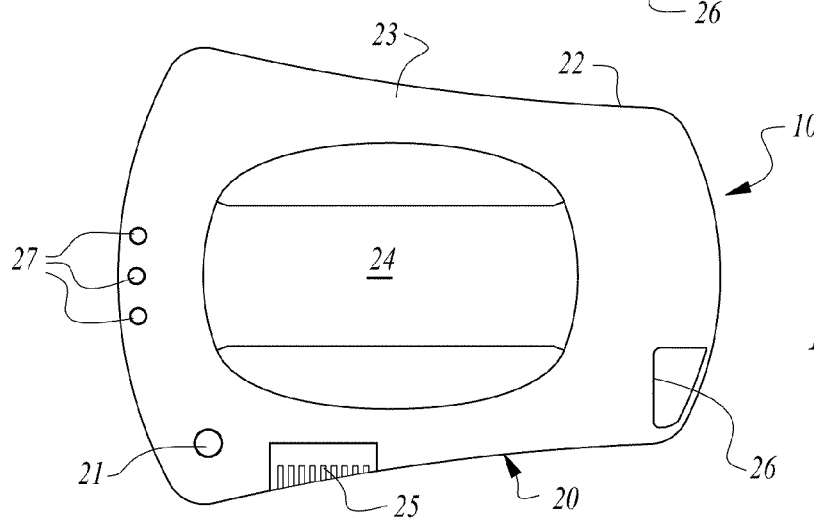
FIG. 7 is a top view of the single sensor version of the apparatus of FIG. 6, according to the present invention.

FIG. 7 provides a top view of the sensor 20 and casing 22. The sensor 20 includes three LED lights 27 for providing visual signals to a user during operation of the apparatus 10, signaling certain conditions or events. The LED lights 27 are deployed in the top 23 of the casing 22. In addition, the sensor 20 includes an LED light 21 in the top 23 of the casing 22 to signal whether the sensor 20 is operating.

Figure 8:
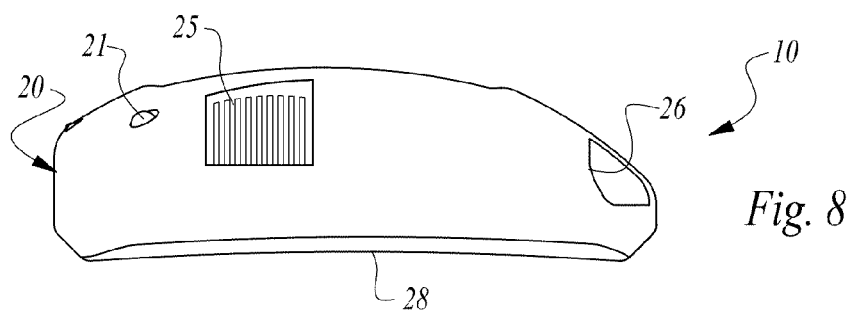
FIG. 8 is a side view of the apparatus of FIG. 6, according to the present invention.

FIG. 8 provides a side profile view of the casing 22 of the sensor 20. The casing 22 is shaped such that the top 23 comfortably conforms to the shape of a user's hand when the sensor 20 is gripped and held against the subject's chest rather than secured to the subject's chest with a strap. During operation, a bottom 28 of the sensor casing 22 is placed adjacent the subject's chest so as to orient and place the transmit antenna 30 and receive antenna 40 in close proximity to the surface of the subject's chest. This profile also provides a configuration that will allow a first responder to provide compressions to a subject in cardiac distress while simultaneously tracking the quality of those compressions along with associated cardiac and respiratory performance. The surface area of the bottom 28 of the casing 22 is sufficient to minimize point loading on a person's sternum while a caregiver or first responder is administering compressions to resuscitate a subject in cardiac or pulmonary distress.

Figure 9:
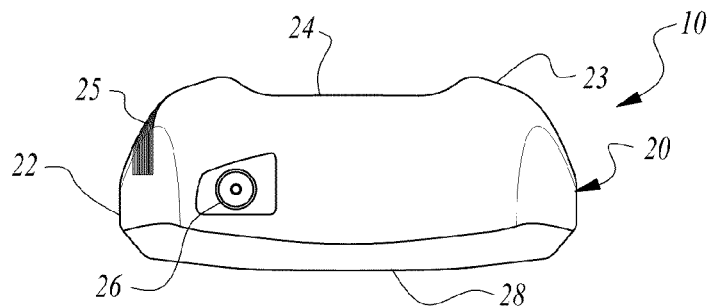
FIG. 9 is a bottom view of the apparatus of FIG. 6, according to the present invention.

FIG. 9 provides an end view of the casing 22 of the sensor 20. The casing 22 includes a data/power port 26 for both receiving electrical power from an external source to operate the components of the sensor 20, and, for communicating data to an external source or for receiving data from an external source, which might include control signals. The end view shown in FIG. 9 also illustrates the profile of the recess 24 in the top 23 of the casing 22. In use, the sensor 20 of the apparatus 10 may be either held adjacent a subject's chest by a caregiver, attached with a strap, attached with some form of adhesive or held in a pocket of a shirt, vest or other article of clothing, simply laid on the subject's chest when they are in a recumbent position, or, incorporated with other devices, such as a defibrillator or EKG.

4. Chest-Centric Single Sensor for Cardiopulmonary Measurement and Tracking

Figure 10:
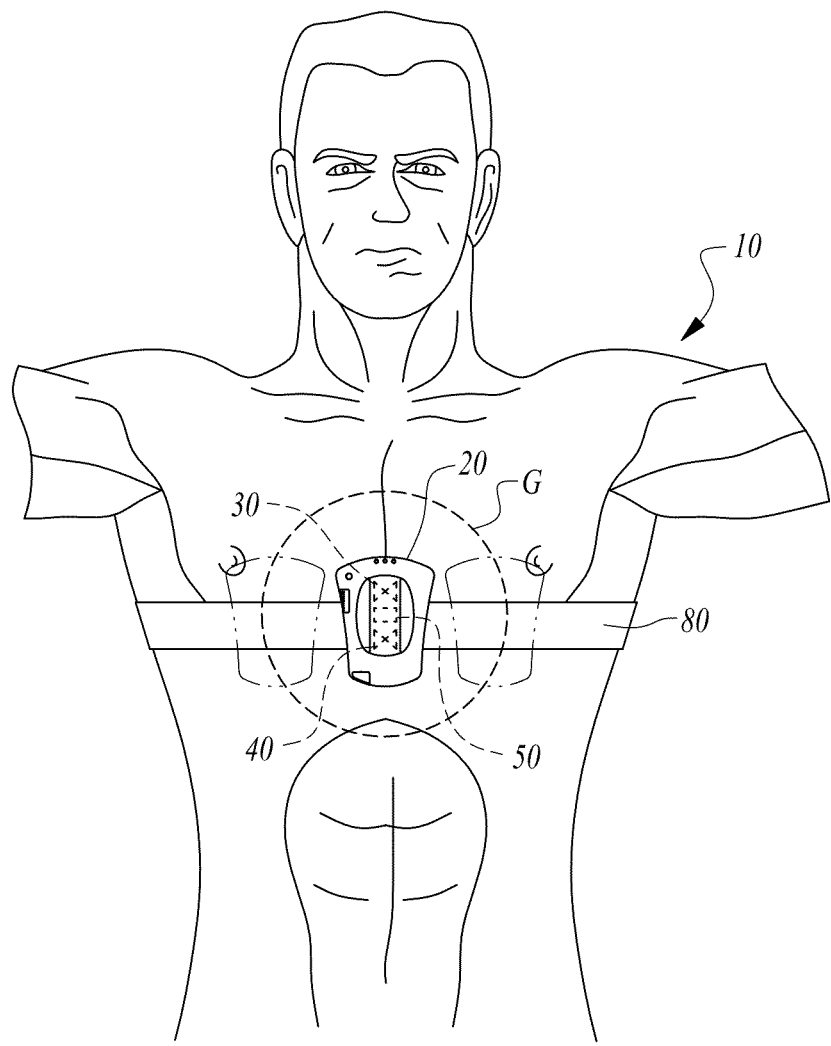
FIG. 10 is an illustration of a single sensor version of the apparatus having sternum-centric placement, according to an embodiment of the present invention.

FIG. 10 is an illustration of a preferred application and embodiment of the apparatus 10 comprising a single sensor 20 secured to a subject's chest which enables simultaneous tracking of both cardiac and pulmonary functionality. The sensor 20 includes a transmitter, 30, receiver 40 and respiratory sensor module 50. The apparatus 10 comprises a single sensor 20, placed on a subject's chest and preferably located within a 3-centimeter radius G measured from the center of a subject's sternum just below the nipple level. Within this radius G, the sensor 20 collects both respiratory and cardiac data for simultaneously determining both respiratory and cardiac rate and rhythm, along with cardiac stroke volume and respiratory tidal volume. The sensor 20 may be attached to the subject using a belt, band or strap 80 that wraps around the subject's chest and holds the sensor 20 in place. The strap 80 rests over the recess 24 in the top 23 of the casing 22. The strap 80 includes a rubber protrusion 81 which conforms to the shape of the recess 24 in the top 24 of the sensor casing 22 and serves to hold the sensor 20 in place at the desired position. As shown, the sensor 20 may be moved linearly along the strap 80 in either direction to redirect the UWB signal to a particular target area, to improve signal response from a particular target area or to collect data from other desired portions of the chest cavity. Alternatively, a caregiver may hold the sensor 20 adjacent the subject's chest in the desired location to collect respiratory and cardiac information, or lay the sensor 20 in different locations on the subject's chest when the subject is in a recumbent position, without the use of the strap 80.

5. Waist-Centric Single Sensor for Monitoring Respiration Rate and Rhythm

Figure 11:
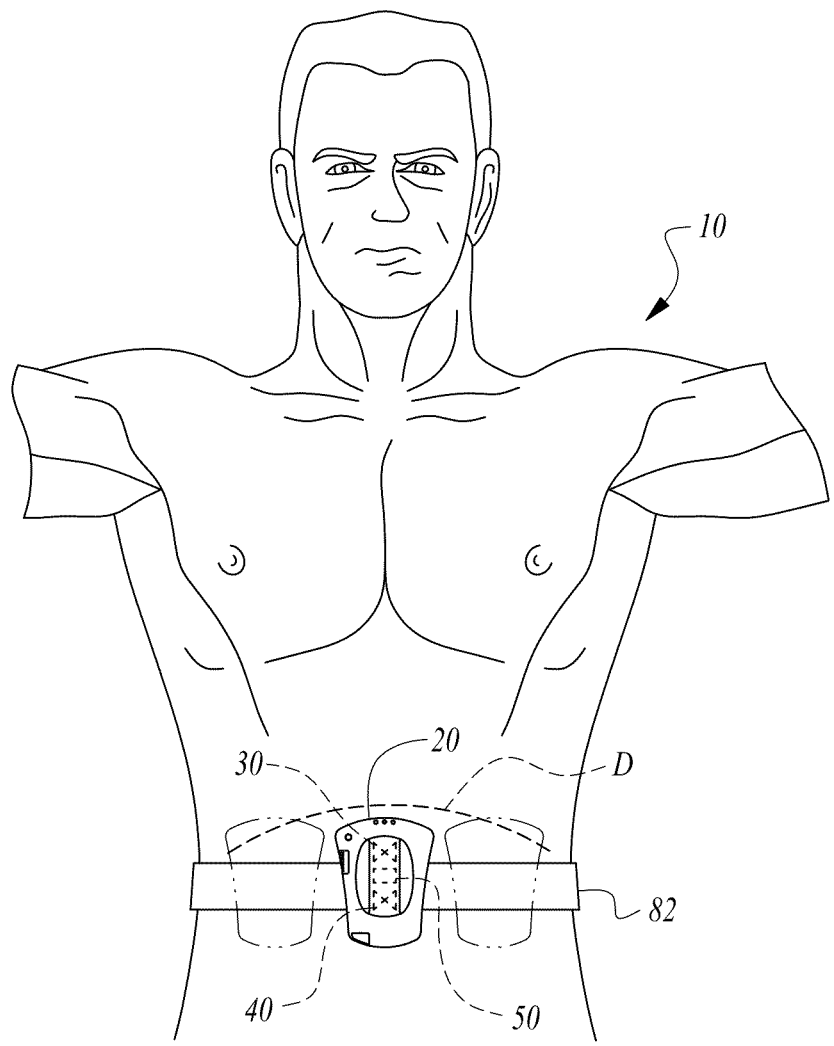
FIG. 11 is an illustration of a single sensor version of the apparatus having waistband-centric placement, according to an embodiment of the present invention.

FIG. 11 is an illustration of an alternative application and version of the apparatus 10 comprising a single sensor 20 wherein the sensor 20 is positioned at the subject's waist to monitor diaphragmatic motion. The apparatus 10 consists of a single sensor 20 having a transmitter 30, receiver 40 and respiratory sensor module 50. The sensor 20 is engaged with a waistband 82 and worn about the subject's waist. The waistband 82 includes a rubber protrusion 81 which mates with the recess 24 in the top 23 of the sensor casing 22 to hold the sensor 20 in place. In this configuration, the apparatus 10 primarily measures and monitors the cyclical motion of the subject's diaphragm muscle D to determine respiratory rate and rhythm, along with other derivative respiratory metrics. The sensor 20 may be placed in the middle of a subject's abdomen, or, located anywhere about the subject's waist including the subject's side, to measure movement of the diaphragm D during a respiratory cycle.

This version and configuration of the apparatus 10 is well-suited to use in athletic activities where placement on the chest could be constraining. Although the focus would be directed to tracking respiratory performance, this version will also collect cardiac information from elements of the anatomy in the diaphragm area which reflect cardiac performance, for example, via blood vessel pulsing.

6. Wireless Sensor Array in Article of Clothing

Figure 12:
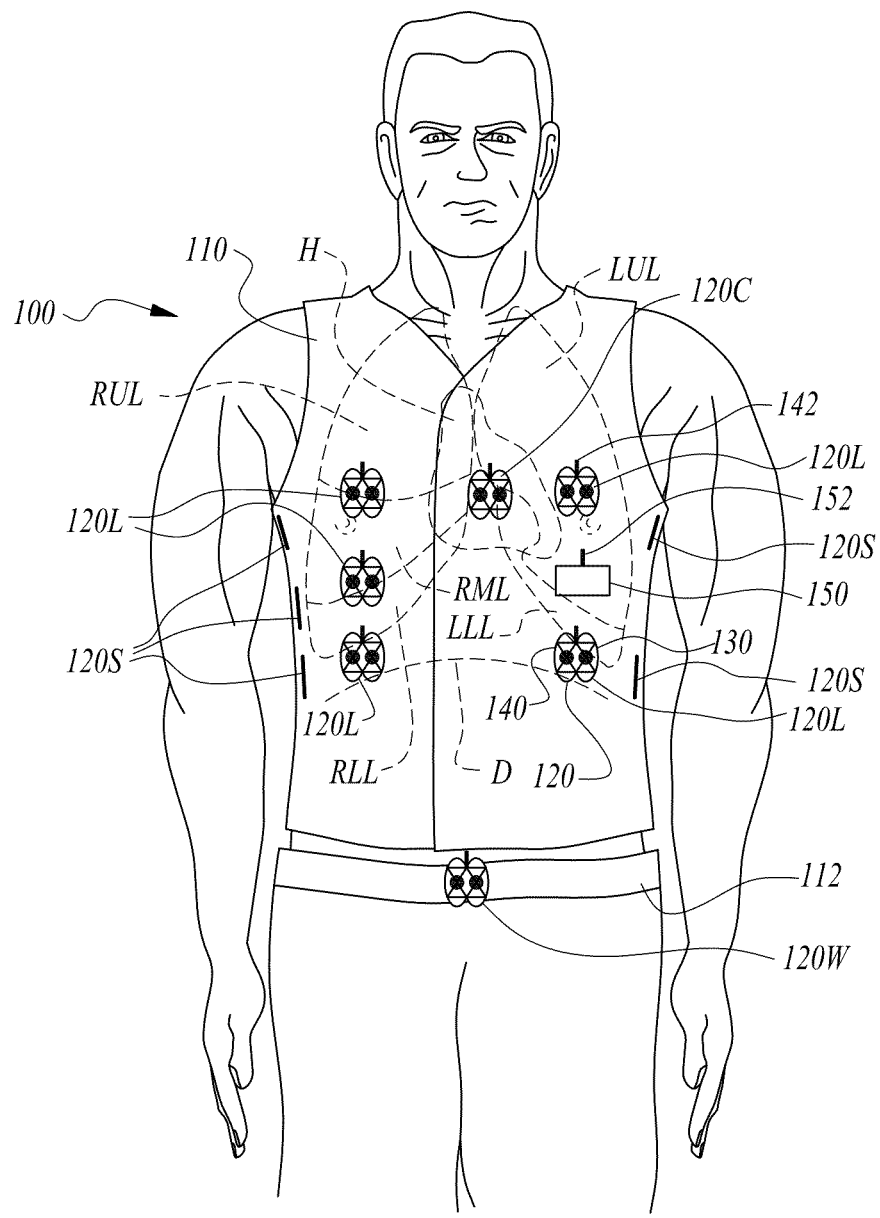
FIG. 12 is a front view of a multiple sensor version of the apparatus worn in a vest and belt configuration, wherein each sensor communicates wirelessly to a central device, according to an embodiment of the present invention.

FIG. 12 is an illustration of an alternative wireless embodiment 100 of the present invention, comprising of one or more wireless sensors 120. The embodiment 100 comprises a vest 110 worn by a subject. The vest 110 is designed to receive and hold one or more wireless sensors 120 deployed at strategic locations about a subject's upper body and waist to monitor particular portions of the subject's upper body and abdomen. Each sensor 120 includes a transmitter 130 and receiver 140. A central command and control hub 150 is deployed within the vest 110 to receive data from each of the sensors 120 and to transmit information to other entities. Each sensor 120 includes an external communications antenna 142 which serves to communicate data collected to the central hub 150 and to receive control signals from the central hub 150. The central hub 150 includes an antenna 152 for receiving data from each sensor 120, for communicating data to external sources and for receiving control signals from external sources, which control signals may then be communicated to each sensor 120.

Thus deployed, the multiple wireless sensors 120 are able to simultaneously measure mechanical movement of various anatomical elements that are indicative of respiratory functionality. By tracking one or more respiratory-induced movements simultaneously, the embodiment 100 will qualitatively and quantitatively characterize breathing patterns and exertion by detecting movement of anatomical elements associated with quiet, deep and other forms of respiration. Additionally, as shown, the sensors 120 may be deployed in proximity to each individual lobe of each lung to provide direct and independent monitoring of each lobe.

As shown in FIG. 12, the lung complex includes left and right lungs LL, RL which are further subdivided into upper, middle and lower lobes. Each lobe has a different shape having independent volumetric expansion and contraction behavior along with different perfusion and dielectric properties. The left lung LL comprises an upper lobe LUL and lower lobe LLL; the right lung comprises an upper lobe RUL, middle lobe RML and lower lobe RLL. Strategic positioning of sensors 120 above each individual lobe provides a novel approach for monitoring respiratory performance by directly tracking the performance of each lobe of each lung, rather arbitrarily monitoring thoracic expansion and contraction which delivers only a measure of overall respiratory rate and rhythm without disclosing any information concerning the functionality of each individual lobe of each lung. The present invention is unique in its ability to individually, simultaneously and noninvasively monitor the performance of each lobe of each lung to allow noninvasive monitoring of physiologic behavior which may more quickly point out certain respiratory concerns. For example, since certain types of breathing create a ventilation/perfusion mismatch, simply monitoring overall respiratory rate and rhythm via thoracic expansion and contraction would fail to provide information concerning performance of individual lobes during a respiratory cycle. The present invention supports a highly granular and faithful assessment of the performance of each individual lobe of each lung during a respiratory cycle, allowing a diagnostician to scrutinize differing behaviors between each lobe.

Now, in greater detail and referring to FIG. 12, an embodiment 100 of the present invention is shown comprising a wearable garment 110 such as a vest where a plurality of sensors 120 are deployed throughout the garment 110 to support specific targeted monitoring of different portions of the thoracic/abdominal volume. In a first version, to obtain increased volumetric accuracy, five sensors 120L are incorporated within the garment on the individual's front at positions above each lobe of both lungs. In a second version, an additional sixth sensor 120C is positioned approximately directly above the middle of the sternum to support simultaneous acquisition of cardiac signals including rate, rhythm and stroke volume, along with respiratory rate and rhythm. In an alternative version, five additional sensors 120S are deployed in side locations of the vest 110 to replace or complement measurements at each lobe for sensors 120L. In addition, although not shown here, one or more of the six sensors 120L, 120C may be repositioned in the vest to be placed adjacent an individual's back. Further, in an additional version not shown here, sensors 120 may be placed in the garment 110 on both the front and back to maximize the data gathered to enhance accuracy of measurements by relying to a greater degree on increased granularity of data acquisition in support of a more accurate shape model. Finally, as desired by the diagnostician, the embodiment 100 can incorporate additional sensors 120 to further increase the granularity of measurements and provide greater resolution to the respiratory model.

The sensors 120 distributed about the garment 110 communicate back to a respiratory hub module 150 via a wireless connection. The hub module 150 is preferably incorporated within the garment 110 and also includes a communications module to allow wireless communication of the collected data from the sensors 120 to other locations, such as a remote doctor's office, a local nurse's/caregiver's station/computer, or, the computer of some other concerned individual, such as a family member. For example, in facilities caring for the elderly, an elderly person would wear the monitoring garment 110 and the hub 150 could communicate locally to an Internet connection to deliver the signal information across the Internet to a doctor monitoring the elderly person's health signs. In another version, not illustrated here, the sensors 120 including the antennae 130, 140 and associated miniature signal processing and storage units are implanted under an individual's skin. The data is communicated from the implanted sensor to an external CPU in a wireless manner. The external CPU may then use the associated communications module to communicate the data to other entities.

The wireless sensors 120 are deployed to target or interrogate various portions or regions of the upper thorax associated with respiratory functionality. For example, wireless sensor 120C is located in the center of the chest adjacent a midpoint of the sternum to capture both cardiac and respiratory motion. Five additional sensors 120L are located adjacent specific portions of a subject's lungs L to monitor the performance and functionality of each lobe of each lung L independently of the other lobes. Additional wireless sensors 120S are deployed along the subject's side in proximity to each lobe of each lung to provide an alternative measure of motion and functionality for each lobe. In addition to the wireless sensors 120 deployed about the chest of the subject, the present multi-sensor embodiment 100 also includes a wireless sensor 120W preferably located at the middle of a subject's waist, held by a belt or waistband 112 to target movement of the diaphragm D. Sensor 120W monitors and tracks the motion of the diaphragmatic muscles D to provide an additional measure of respiratory functionality. Each wireless sensor 120 includes a separate data communication antenna 142 which delivers collected data to a wireless sensor hub module 150 located within a pocket or other holder of the vest 110. The data communication antenna 142 can support data transmission to the hub module 150 using one of several known telecommunication protocols, including Bluetooth and UWB. Although shown here as having wireless connectivity, the sensors 120 could also alternatively be connected via wired links which run through the article of clothing to the sensor hub module 150.

Although shown as associated with a vest 110, the wireless sensors 120 may be deployed in other types of clothing articles, may be deployed in pockets of a clothing article, may be attached to a Velcro patch, may be sewn and integrated in a piece of clothing, and, may be deployed in conjunction with other devices such as a defibrillator. The wireless sensors 120, for example, could be integrated in a bullet-proof vest, personal armor, a jacket, a protective piece of clothing used by a worker in an industrial setting, a wetsuit, a fully enclosed suit used in hazardous response or incident response, and further, within a space suit used by astronauts in space exploration. The apparatus 100 is tuned and calibrated to accommodate any attenuation or change in signal transmissivity associated with different types of materials used in the article worn by the subject housing the wireless sensors 120. Thus deployed, the wireless sensors 120 can be positioned to independently and individually monitor functionality of each lobe of each lung L and the heart H. For example, wireless sensor 120C is positioned to monitor the heart H and lungs L simultaneously. Multiple sensors 120L and 120S are positioned to independently measure the functionality of each of the various lobes of the lungs including the upper lobe of the right lung RUL, the middle lobe of the right lung RML, and the lower lobe of the right lung RLL. Further, additional wireless sensors 120S and 120L are positioned to measure functionality of the upper lobe of the left lung LUL and the lower lobe of the left lung LLL. Although not shown in FIG. 12, the wireless sensors 120 deployed in the front of the vest 110 could likewise be deployed in similar positions on a backside of the vest 110. Additionally, the wireless sensors 120 could be deployed in all positions simultaneously including front, side and back, providing higher density data collection and the opportunity to aggregate and compare data from multiple wireless sensors 120 simultaneously.

7. Wired Sensor Array

Figure 13:
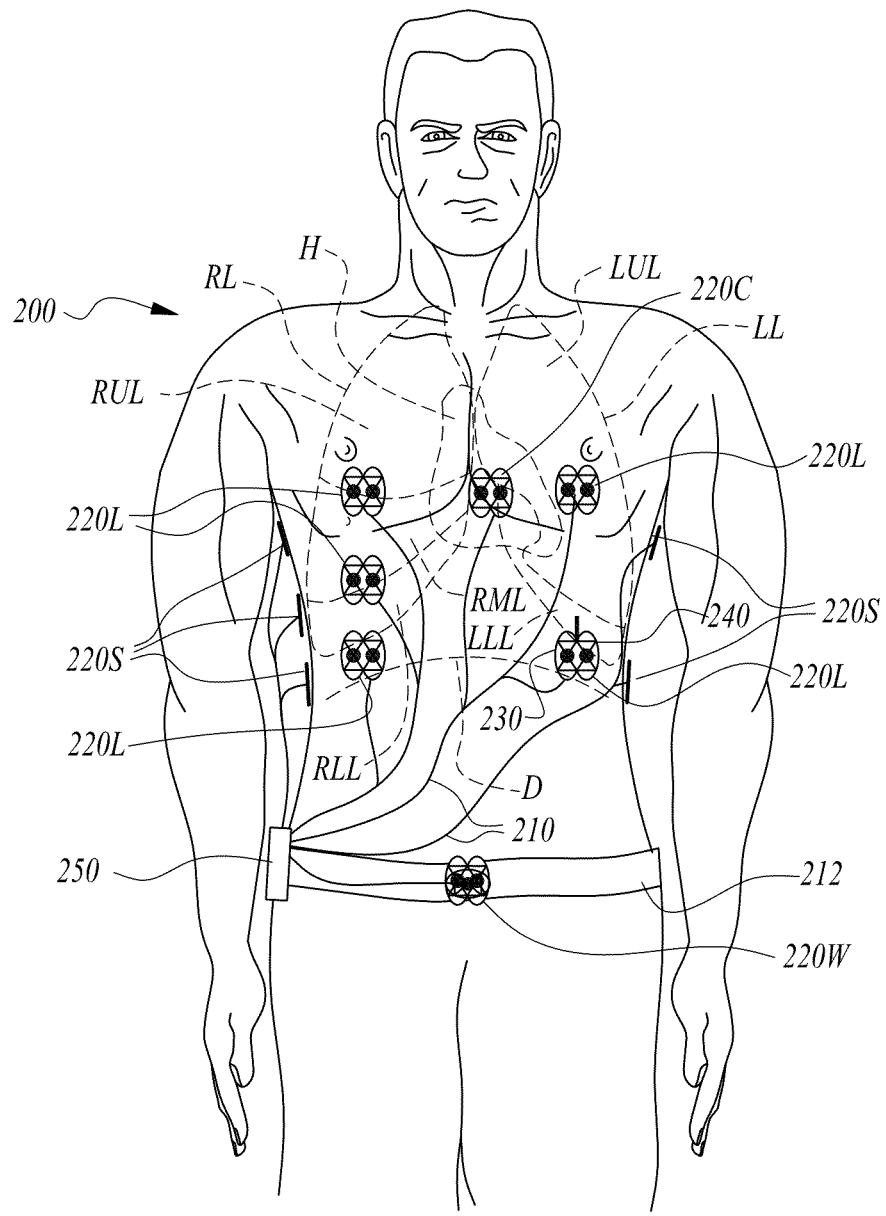
FIG. 13 is a front view of a multiple sensor version of the apparatus wherein each sensor communicates via wired links to a central device, according to an embodiment of the present invention.
Figure 14:
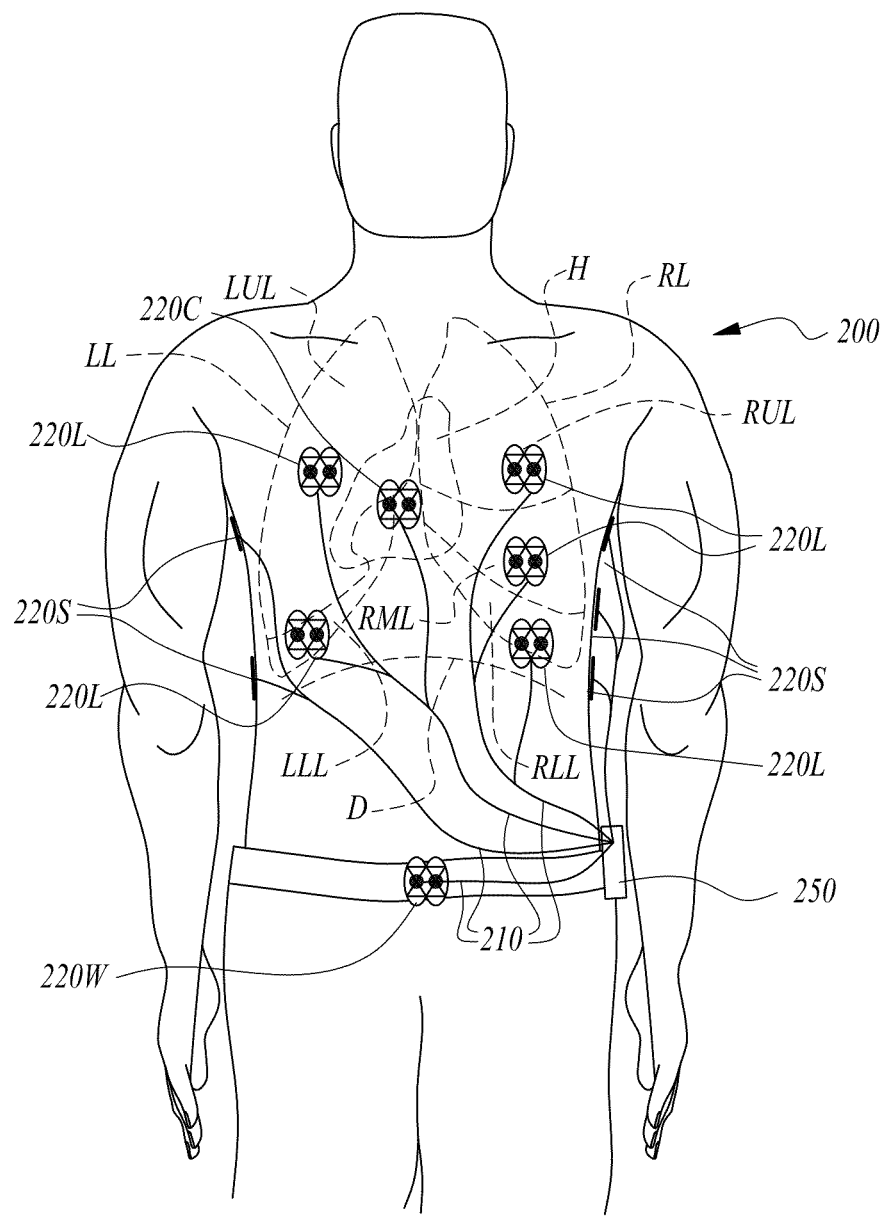
FIG. 14 is a back view of the multiple sensor version of the apparatus of FIG. 13, according to an embodiment of the present invention.
Figure 15:
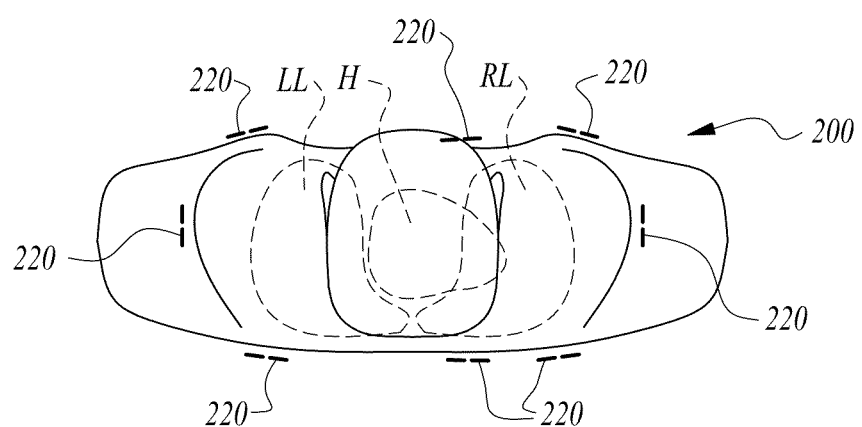
FIG. 15 is a top view of a multiple sensor version of the apparatus of FIG. 13, according to an embodiment of the present invention.

FIGS. 13-15 are illustrations of an alternative version of a multi-sensor embodiment 200 comprising multiple sensors 220 adhered to the surface of a subject's skin. Each sensor 220 communicates via wired links 210 to a central hub 250. FIG. 13 is a front view of a subject illustrating the deployment of a plurality of wired sensors 220 on a subject's front. FIG. 14 is a back view of the subject illustrating the deployment of a plurality of wired sensors 220 on a subject's back. FIG. 15 is a top view of the subject illustrating the deployment of multiple sensors 220 about the front, back and side of the subject's upper torso. The deployment of a plurality of sensors 220 about the upper torso of a subject allows data to be collected from a plurality of strategic locations. This data can then be aggregated to create a highly resolute assessment of respiratory performance, and, to determine the location of any problematic areas or anatomical elements, such as in determining the onset of congestive heart failure as determined by measurement of changes in dielectric values in the various lobes of the lungs.

Referring to FIG. 13, multiple sensors 220 are placed strategically about a subject's thorax and abdomen and positioned to capture movement of key anatomical elements involved in respiration, including both quiet and deep breathing. The sensors 220 communicate collected reflected signals S' and associated data via wired links 210 to a central data collection, processing and distribution hub 250. Multiple sensors 220L and 220S are positioned to collect data from each lobe of each lung, including the right lung upper lobe RUL, the right lung middle lobe RML, the right lung lower lobe RLL, the left lung upper lobe LUL and the left lung lower lobe LLL. Sensor 220C is positioned in the middle of the sternum to simultaneously collect cardiac and respiratory information from a location where the transmitted signals S capture both respiratory and cardiac-related motion. Sensor 220W is positioned to measure motion of the diaphragm D to primarily collect respiratory information, but may also be used to pickup cardiac rate and rhythm via motion associated with each pulse. By measuring the motion of these elements, or lack thereof, the level of effort being expended by an individual may be determined.

Following are illustrative examples of specific anatomical motion to be monitored and tracked by the sensors 220. This motion is correlated and aggregated to develop the various measures and metrics of respiratory performance relative to various disease states. The data collected may be aggregated and disaggregated as necessary to support a plethora of different analyses relative to the condition being evaluated. For example, during deep breathing, one would expect the manubrium sterni to move 30 mm in an upward direction and 14 mm in a forward direction during inspiration. Additionally, the width of the subcostal angle, at a level of 30 mm below the articulation between the body of the sternum and the xiphoid process, is increased by 26 mm. Further, the umbilicus is retracted and drawn upward for a distance of 13 mm. By measuring these and other movements induced by respiration, the multiple wired sensor embodiment 200 of the present invention obtains mechanical motion data that is processed via one or more algorithms in software or hardware to produce qualitative and quantitative respiratory metrics.

The data from each sensor 220 is delivered via hard-wired data links 210 to a hub 250, which is shown in this version as being worn on the subject's hip. As shown in FIG. 13, the wired sensors 220 are adhered to the subject's chest, back and waist in strategic locations comparable to the placement of wireless sensors 120 in the vest 110 illustrated in FIG. 12. Thus configured, the wired sensors 220 are able to interrogate portions of the subject's lungs or measure different portions of the subject's muscular and other anatomical elements that exhibit respiration-induced motion. As shown in FIG. 15, where wired sensors 220 are positioned at opposing locations of opposing sides of the subject's body, the embodiment 200 is able to collect and compare data from different portions of the lungs and use comparative analytical techniques to confirm that all sensors 220 are tracking properly and collecting functional and other data reflective of counterpart sensors 220 on the subject's torso which should be measuring and obtaining similar empirical data.

Although the embodiment 100 having wireless sensors 120 and the embodiment 200 having wired sensors 220 are shown as being separate embodiments, a third derivative embodiment would comprise a hybrid configuration including both wireless sensors 120 and wired sensors 220. The integration of both the wireless embodiment 100 and wired embodiment 200 would provide an additional deployment configuration to support special requirements in certain instances. For example, wired sensors 220 could receive power from a larger battery pack worn by a user to support a greater duty cycle to collect more frequent data while wireless sensors 120 could be deployed at locations where wired links 210 might encumber movement. This combination would provide greater flexibility in determining where to collect data, how long to collect data, and, how much data to collect.

8. Linear Multiple Sensor Interrogation

Figure 16A:
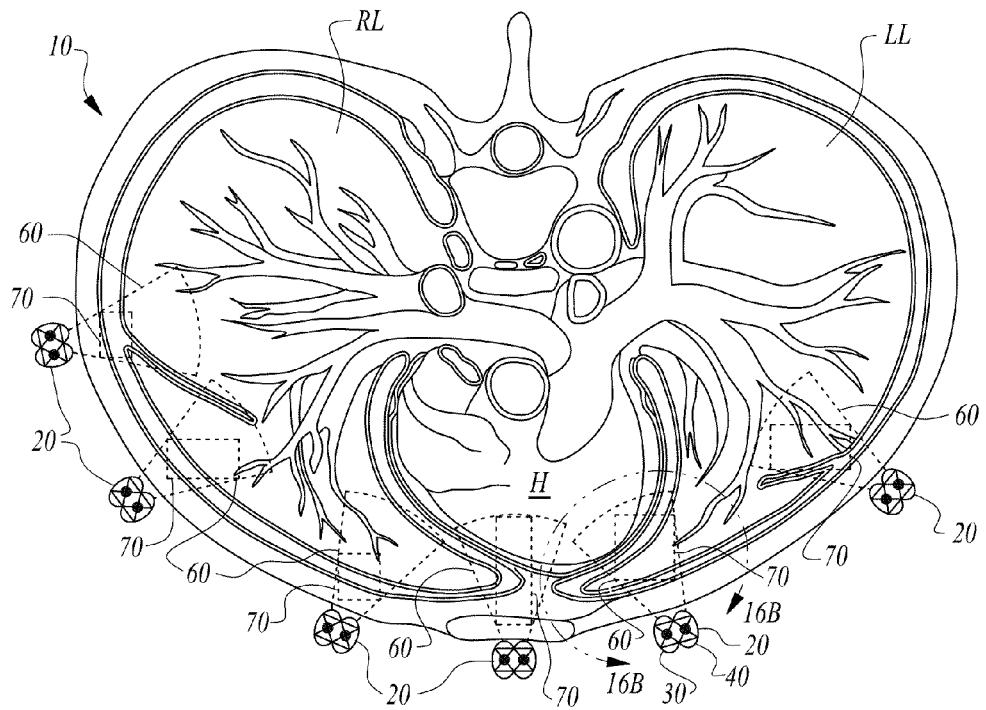
FIG. 16A is a cross-sectional view of an individual's chest cavity with multiple sensors, according to an embodiment of the present invention.
Figure 16B:
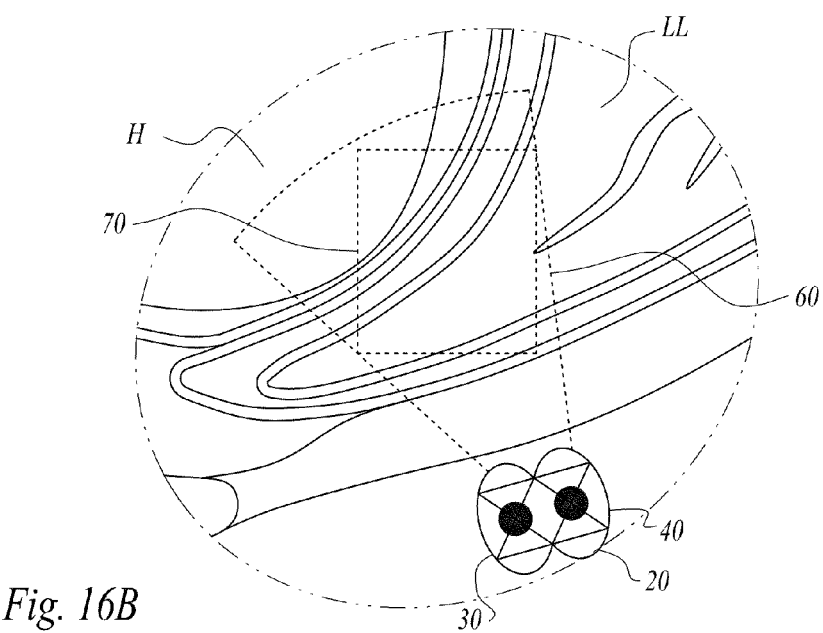
FIG. 16B is a magnified view of that portion of FIG. 16A, defined by the circumferential line 16B-16B, illustrating the interrogation of multiple tissue interfaces by a single sensor, according to an embodiment of the present invention.

In an alternative embodiment of the apparatus 10, as illustrated in the cross-sectional views of FIG. 16A and FIG. 16B, several sensors 20 are targeted toward specific portions of a subject's chest cavity to create multiple interrogation volumes 60 to capture and encompass multiple defined respiratory chambers 70, along with the static and dynamic properties of each respiratory chamber 70. Each respiratory chamber 70 serves as an independent and autonomous model having independent properties and behavior for each specific portion of the respiratory chamber 70 encompassed by the interrogation volume 60. Additionally, each of the individual respiratory chambers 70 may be aggregated and coupled to reflect the excursion for a more complex respiratory chamber configuration, providing a highly granular yet more accurate assessment of instantaneous respiratory chamber volume and respiratory parameters. As shown in FIG. 16A, the sensors 20 are preferably deployed in a linear arrangement to create a common plane of interrogation within the chest cavity and to support synchronization and comparison of data collected from the proscribed portions of the subject's chest.

FIG. 16A and FIG. 16B are illustrations of a version 10 of the present invention with sensors 20 deployed in a circumferential fashion across a subject's chest. FIG. 16A is a cross-section view of an individual's chest cavity with multiple sensors 20 of the apparatus 10 deployed about the subject's chest. FIG. 16B is a magnification of that sensor 20 and interrogation volume 60 circumscribed by the line 16B. This magnified view illustrates the operation of a sensor 20 interrogating a target area or volume 60 of the chest cavity encompassing aspects of the skeletal structure, the lungs and the heart, along with the pleural spaces and the myriad tissue interfaces comprising the particular target area.

Each sensor 20 includes a transmitter 30 and receiver 40 to transmit, receive and collect reflected data associated with mechanical aspects of respiration. The reflected signals S' are received and processed by a respiratory sensor module 50 capable of resolving a change in a spatial configuration of the subject's lungs or movement of an internal tissue, such as ribs, diaphragm, chest wall, lung tissue surfaces, and other tissue interfaces which correlate with respiratory-induced motion, thereby determining respiratory rate and rhythm. Each sensor 20 interrogates a portion of the chest cavity to track motion and dielectric state within a target interrogation volume 60. Each target interrogation volume 60 encompasses a defined respiratory chamber 70 comprising a portion of the overall respiratory model according to the invention. One or more target regions or volumes of the right lung RL, left lung LL, or associated tissues whose movement is influenced by motion during the respiratory cycle may be continually interrogated. Each target interrogation volume 60 may be independently analyzed as a single respiratory chamber 70 or aggregated with measurements from other interrogation volumes 60 to comprise an overall respiratory chamber 70 comprised of one or more respiratory chambers 70. The respiratory chamber 70 comprises a volumetric portion of the lungs, which is monitored by one or more sensors 20. Each respiratory chamber 70 has a prescribed geometry and associated volume driven by sensor 20 placement. Each sensor 20 tracks an interrogation volume 60 which encompasses and captures all or a portion of a complete respiratory chamber 70 and each sensor 20 contributes its information to an overall assessment of respiratory chamber dynamics. The aggregated measurements from each of the interrogation volumes 60 which form the desired respiratory chamber 70 are extracted for use in calculating the various respiratory parameters and metrics associated with the selected respiratory chamber configuration.

Now, in greater detail, with continued reference to FIGS. 16A and 16B, in practice, each sensor 20 transmits a series of extremely short duration electromagnetic pulses S into the human body toward areas of interest in an interrogation volume 60. As the energy enters the body and encounters a boundary between different biological substances such as skin-fat, muscle-blood, tissue-air, or bone-fluid, small amounts of the incident energy are reflected back towards the sensor 20 where the reflected signals S' are captured and pre-processed. Each combination of tissues exhibits its own factor of reflectivity.

Each sensor 20 captures raw reflections using a high speed sample and hold circuit where the desired capture time for the sampler is set to equal the round trip time of flight of a transmitted signal S from the sensor 20 to a target or range of interest T and back to the sensor 20. Sampled reflections S' from a given depth or range of depths are integrated to minimize high frequency noise that may corrupt the desired data related to tracking instantaneous respiratory volume, rate and rhythm. The integrated signal is amplified and passed through a low-pass filter to prevent signal aliasing prior to digitization. After a predetermined number of reflections S' for a first range of interest are collected and integrated, the sensor sample timing is changed, allowing capture of reflections from the next range of interest. This process is repeated until reflections S' from the entire range of interest, such as across a portion of the chest cavity, i.e., the interrogation volume 60, are collected. The process is then continually repeated to deliver an updated instantaneous measure of respiratory volumetric changes, and, associated respiratory rate, rhythm and other derivative parameters, associated with one or more interrogation volumes 60 and a prescribed respiratory chamber configuration.

For dynamic monitoring of physiological structures such as the lungs L, the physical location of the boundaries within the target range of interest will move with respect to the generally fixed position of the sensor 20 and its antennae 30, 40, producing a complex series of time-varying reflections S'. The time-varying reflections S' are continually processed by the sensor 20 to extract both mechanical information and electrical information associated with the activity of the lungs.

In FIG. 16B the sensor 20 generates an interrogation volume 60 encompassing a respiratory chamber 70. The respiratory chamber 70 includes portions of the subject's heart and left lung LL. By measuring the excursion and motion of the various tissue interfaces within the respiratory chamber 70, the apparatus 10 is able to assess both cardiac and pulmonary performance.

9. Multiple Sensor Lobe-Centric Configuration for Obstruction Detection

Figure 17:
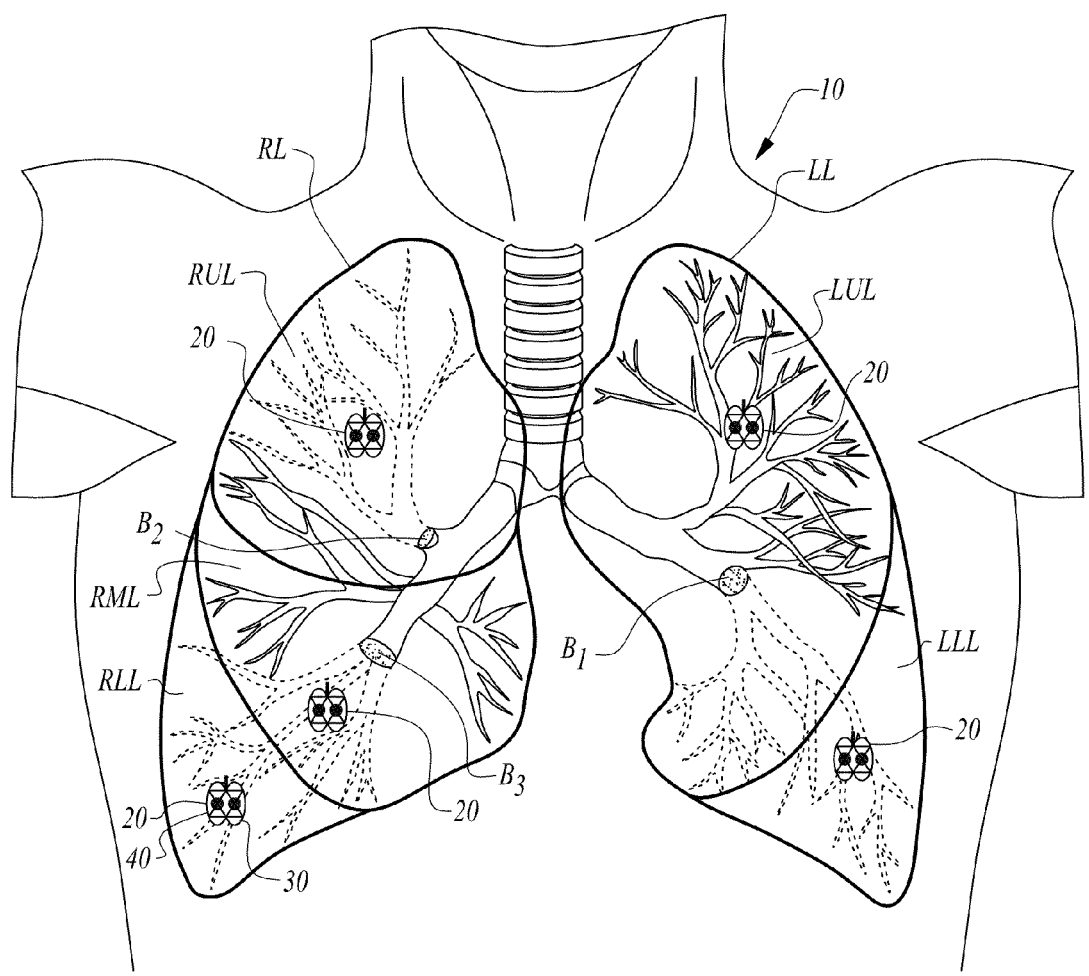
FIG. 17 is a front view of a multiple sensor lobe centric version of the apparatus illustrating parenchymal lung obstruction detection, according to an embodiment of the present invention.

FIG. 17 provides an illustration of a further application and embodiment of the apparatus 10 of the present invention building on the features and functionality of earlier described embodiments, particularly the embodiment illustrated in FIGS. 2 and 3. In this version, the invention is able to determine the location of obstructions within a subject's bronchii based on the measured behavior of individual lobes of each lung. The apparatus 10 comprises five or more sensors 20 positioned at strategic locations on a subject's chest to monitor and track the individual lobes of each lung. The sensors 20 can be deployed in either a wired or wireless configuration. FIG. 17 is a cut-away view of a subject's chest, revealing both the left lung LL and right lung RL. Each lung LL, RL is further delineated into its individual lobes. The right lung RL comprises a right upper lobe RUL, a right middle lobe RML, and a right lower lobe RLL; the left lung LL comprises a left upper lobe LUL and a left lower lobe LLL. In practice, individual sensors 20 are positioned on a subject's chest so as to monitor motion and state of each of the five lobes independently. With sensors 20 strategically positioned to interrogate a volume 60 and respiratory chamber 70 in each individual lobe, the apparatus 10 is able to deliver information concerning the respiratory functionality of each individual lobe. Consequently, the apparatus 10 may be used to identify whether a subject has any obstructions in any of the bronchi.

For example, in operation, where there exists a blockage B1 in the left lung LL, a sensor 20 positioned adjacent the left lower lobe LLL would detect a decrease or delay in inflation of the left lower lobe LLL as compared to inflation in the left upper lobe LUL as measured by a separate sensor 20. Consequently, based on the comparison, a physician would be able to determine that some form of obstruction or other restriction existed in the area of blockage B1. Thus, a condition may be isolated to a more specific location. Still further, in the situation where a blockage B2 in the brachia of the bronchia supplying air to the right upper lobe RUL is present, the sensor 20 positioned to monitor the right upper lobe RUL would measure less or delayed inflation as compared to a normal, unobstructed circumstance or as compared to the measured behavior of another lobe, such as the right middle lobe RML. Likewise, in the circumstance where an obstruction B3 occurs, sensors 20 positioned to monitor the right middle lobe RML and the right lower lobe RLL would detect less or delayed inflation as compared to a normal state without an obstruction, or, as compared to relative inflation of the right upper lobe RUL. Thus, the apparatus 10 of the present invention would be able to provide indications of obstruction or restriction in the bronchii or branches thereof, without having to initially resort to the use or more invasive procedures and instruments. Once the general location of an obstruction or restriction has been identified using the apparatus 10, a physician would then be able to minimize the exploratory requirements using more invasive instruments and techniques. Instead, for example, having determined that a blockage exists at any of the sites B1, B2, or B3, the physician could focus his investigation on indicated locations. In addition to obstruction detection, the present embodiment would also support the detection of a tension pneumothorax or hemopneumothorax by identifying reduced inflation in portions each lobe or each lung.

10. Multiple Sensor Lobe-Centric Configuration for Congestion Detection

Figure 18:
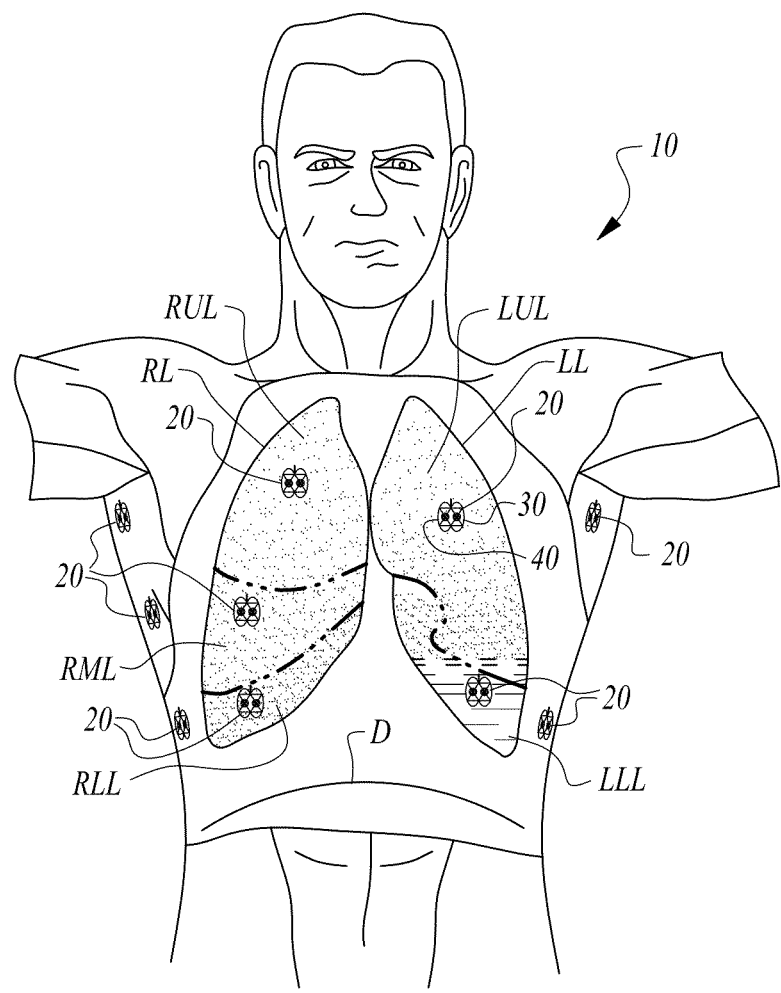
FIG. 18 is front view of a multiple sensor lobe-centric version of the apparatus illustrating pulmonary congestion detection, according to an embodiment of the present invention.

FIG. 18 is an illustration of a further embodiment of the apparatus 10 invention directed toward monitoring pulmonary congestion indicative of cardiac performance deterioration or other disease states. Congestive heart failure is a serious physiological condition that is associated with changes in respiratory performance. FIG. 18 provides an exemplary illustration of an individual where the right lung RL is clear and without congestion, while the left lung LL is shown as having a buildup of fluid in its lower regions, suggesting the onset of congestive heart failure, the presence of other disease states, or, the presence of a pneumothorax, hemopneumothorax or other actual damage to the lungs which has resulted in a buildup of fluids either within the lung tissue or outside the lung in the pleural space. Congestion can occur even in a healthy person during bouts of pneumonia or other ailments which compromise the respiratory system.

In one embodiment, as illustrated in FIG. 18, congestion in lungs may be monitored by one or more sensors 20. Referring as well to FIGS. 16A and 16B, in a congestive heart failure monitoring mode, the apparatus 10 transmits a series of pulses at a target respiratory chamber 70 comprised of one or more interrogation volumes 60. The apparatus 10 comprises one or more sensors 20 having a transmitting antennae 30 and receiving antennae 40. The transmitting antenna 30 of each sensor 20 directs electromagnetic energy in the form of an ultra-wideband radiofrequency signal S toward a target area T circumscribing a target respiratory chamber 70. A portion of the transmitted energy is reflected back to the receiving antenna 40, in part, due to the large difference in dielectric value between the air and liquid in the lungs RL, LL, along with dielectric differences in other tissues in the target area T of interest.

The apparatus 10 incorporates an advanced algorithm used in conjunction with one or more algorithms of the respiratory sensor module 50 for capturing dielectric information to support capture and processing of additional data to assist in determination of changes in dielectric measurements during a respiratory cycle. As additional fluid builds up in the lungs RL, LL, the various sensors 20 will monitor the dielectric value in the various portions of the lungs RL, LL. For example, the sensors 20 will continually measure the dielectric value in the right upper lobe RUL, the right middle lobe RML, the right lower lobe RLL, the left upper lobe LUL, and, the left lower lobe LLL.

In FIG. 18, portions of both the left lower lobe LLL and the left upper lobe LUL are shown as having a buildup in fluid content as compared to the lobes of the right lung RL and as compared to the normal state of the left lung LL. As the sensors 20 measure the change in the dielectric values of portions of the lungs RL, LL, the apparatus determines whether there is a change associated with a trend toward congestive heart failure. The methods of the present invention associated with measuring and comparing the changes and trends in dielectric values to assess the potential or actual onset of congestive heart failure are described later in this document.

11. Variable Adaptive and Customizable Lung Models

The present invention supports the use of various two-dimensional and three-dimensional lung models. In particular, the present invention supports a novel method for use of lung models wherein each lobe of each lung can be modeled separately and independently from each of the other lobes, and then, aggregated or compared with information from monitoring of the other lobes to provide unique analytical, diagnostic and treatment opportunities. The present invention also supports a novel method for modeling multiple portions of each lobe of each lung along with other portions of the anatomy which might be relevant to an assessment or diagnosis. With an increase in the number of sensors used, the model for the present invention can provide a highly granular and resolute assessment of respiratory performance. The lungs can be modeled using a number of different shapes which may affect the accuracy and precision of the measurements depending on the coarseness of the model. In certain versions, use of a single sensor 20 may be sufficient for the accuracy desired. Other applications may benefit from having data from multiple sensors 20 aggregated in a more complex model.

For example, in a first version, and with reference to FIG. 2, each lung is presumed to be in the shape of simplified rectangular box having dimensions roughly approximating the size of the lungs. In this instance the excursion from just one sensor 20 may be used to drive the entire respiratory model. Accuracy of the model will vary depending on the type of breathing and closeness of this model to actual empirical behavior of the lungs of the specific individual.

In a second version, and with reference to FIG. 16A, a more complex lung geometry and shape may be used in the algorithm of the present invention, where data from individual sensors drive individual portions of a complex model and those individual portions are aggregated as appropriate to determine desired pulmonary metrics. For example, the model may be comprised of shapes for each lobe of each lung where individual sensors 20 measure the excursion of each individual lobe and then the data is aggregated to produce overall pulmonary metrics. In one application, as described earlier, the apparatus 10 determines the presence of an obstruction within the lung, such as a penny or a peanut, by observing data from each sensor 20 and isolating the sensor 20 and lobe indicating reduced or abnormal excursion during a respiration cycle. For example, excursion which is reduced during inspiration can indicate that an obstruction is present which is impeding flow into a particular lobe; reduction of excursion which is delayed during expiration can likewise indicate an obstruction or other form of restriction, such as the presence of asthma or other disease state which has caused an inflammatory condition in the lungs. Likewise, this information could be used to indicate the ingestion or inspiration of some type of hazardous material or biologic material known to cause inflammatory or other detrimental conditions in a person's lung complex.

In a third version, a simple rectangular box may be used as the desired geometric model to both simplify calculations and to leverage excursion data from preferably just one sensor. The box is sized so as to more closely approximate the actual volumetric behavior of the lungs in correlation with actual excursion distances measured by the desired sensors. This version is developed by preferably acquiring empirical respiratory performance data from an individual by measuring actual respiratory performance during respiratory cycles using other measurement devices, such as a plethysmograph. Using this empirical data, a custom algorithm accurately representing the individual's respiratory performance is produced and incorporated in the algorithm and method of the invention. This custom algorithm and associated geometric model is optimized to support measurements from a minimum number of sensors, preferably, just one sensor.

In a fourth version, a very detailed shape may be used for the lung model based upon data from other imaging technologies, combined with empirical data, to generate a highly resolved algorithm correlated with high granularity to the individual's physiology and number and placement of sensors and, multiple measures of excursion may be applied to the more complex model to develop a more accurate and precise measure of pulmonary functionality. For example, highly resolute data from X-ray, MRI or other imaging technologies may be used to create a more accurate lung model. Since respiratory performance measurements need not necessarily rely on a highly resolved model capable of determining exact absolute values, the present invention is highly functional and useful using a coarse model.

So, in a first approach and application, the apparatus and method of the present invention calculates instantaneous respiratory volume by applying the measured excursion distance from a prescribed respiratory chamber 70 of a target interrogation volume 60 to a simplified rectangular model and calculating the volume of a simple rectangular box using a measured excursion distance between the front and back walls of the box at a particular point in time. Subsequently, the apparatus and method calculates the change in instantaneous volume as a function of time, thereby supporting the calculation and assessment of pulmonary tidal volume. As indicated above, the IRV module of the present invention is adaptive to include more complex volumetric calculation models based upon a more complete physical model of the targeted respiratory chamber, including a model based on more complex static imaging, such as from an MRI, X-ray or other imaging device. Empirical data may be used and correlated to the signals processed by the IRV module to arrive at a highly accurate measure of instantaneous lung volume and derivate parameters, including tidal volume. Additionally, in a further embodiment, where a more complex model of the lung is used, additional sensors 20 may be deployed at multiple locations along the chest or back in correlation to the model to collect multiple and more resolute excursion distances for each key section of the complex lung model. For example, sensors 20 could be placed over the upper, middle and lower lobes of both lungs and excursion distances collected for all lobes, each having their own specific geometric shape and behavior. By calculating the excursion distance for each lobe of the lung, the invention is also able to determine if there is a potential physical obstruction in one of the branches of the lung, such as a peanut or penny, by comparing the changes in each lobe to each of the other lobes during a respiratory cycle.

During monitoring, once the apparatus 10 has calculated instantaneous lung volume, the change in instantaneous lung volume over time is also calculated. Then, the apparatus 10 is able to calculate all other derivative pulmonary functional parameters.

For example, tidal volume is calculated by taking the difference between the maximum and minimum respiratory chamber volume during each respiratory cycle. Respiratory output is calculated by multiplying the tidal volume by the respiratory rate. Respiratory rate and rhythm are acquired by measuring the maximum and minimum excursion over time as well. The present invention is able to measure and determine these various pulmonary and respiratory metrics to support monitoring of an individual's respiratory health and performance. Once all desired respiratory/pulmonary parameters have been developed by the apparatus 10, the results may be presented to various users in a manner most appropriate for the individual's or user's needs.

12. Concurrent Cardiac and Pulmonary Assessment

In an alternative embodiment, the present invention demonstrates a novel apparatus and method using ultra-wideband radar to detect conditions within the thoracic and abdominal areas that will lead to a determination of changes in lung volume. In particular, the apparatus 10 of the present invention supports the instantaneous and continuous noninvasive measurement of changes in lung volume, while also measuring parameters including respiratory rate and rhythm. In addition to respiratory rate and rhythm, the apparatus and method of the present invention provides an instantaneous assessment of tidal volume and other advanced respiratory parameters. Consequently, the apparatus provides a unique capability to continuously and instantaneously monitor and track pulmonary functionality to provide critical information on the health of both the pulmonary and cardiovascular system.

Additionally, the apparatus and method of the present invention simultaneously extracts medical and physiological data from subjects concerning both cardiac and pulmonary performance and functionality to produce respiratory knowledge. The apparatus measures cardiopulmonary function without direct skin contact. The apparatus preferably comprises a miniature UWB radar transceiver connected to a data processing device hosting unique software and associated signal processing components. The apparatus, in combination with proprietary algorithms included in the software and hardware components, produces a novel output that allows one to non-invasively detect and track heart and lung motion, along with instantaneous volumetric information and dielectric information. The apparatus collects cardiopulmonary rate and rhythm information for use in patient monitoring prior to an abnormal event, during an event, and, to evaluate treatment such as resuscitation efforts.

The apparatus utilizes electromagnetic energy to interrogate the body and extract physiological data. The methods associated with the apparatus use Finite Difference Time Domain (FDTD) analysis techniques to model the electromagnetic interaction between complex 3-dimensional physical systems such as the human body and the radar antennas of the apparatus used to transmit and receive electromagnetic energy.

The present invention incorporates novel geometrical models and functional algorithms which account for various nonlinearities and provide a correlation between lung surface area and volume. In a further embodiment of the present invention, the apparatus and method provides an initial three-dimensional empirical measure of the size and shape of each lung, which is then used by the microprocessor 56 of the respiratory sensor module 50 and associated software to generate a significantly more precise and accurate measure of the actual volumetric changes of a specific individual's lungs during a respiratory cycle.

As illustrated in FIG. 12, to provide more specific information concerning changes in lung volume, sensors 120 may be placed strategically to capture changes in portions of the lungs, including the upper, middle and lower lobes. Integration and comparison of the changes in volume in individual lobes will provide a more accurate assessment of overall pulmonary functionality, and, allow additional diagnostic assessments to be performed by measuring and comparing changes between the lobes where differential lobe behavior is know to predict certain pulmonary functionality that is relevant to diagnosing particular conditions. For example, as illustrated in FIG. 17, measurement of minimal excursion in one lobe below an expected value, juxtaposed against measurement of normal excursion in other lobes, can be indicative of a physical obstruction in a portion of a lung or some other indicated condition, such as early diagnosis of lung congestion indicative of potential heart failure.

The present invention provides an assessment of changes in respiratory chamber volume to provide useful diagnostic information and respiratory knowledge, irrespective of the specific size and shape of a subject's lungs. However, in a further embodiment of the present invention, the software allows the specific lung shape and size to be changed to account for expected differences as a result of age, muscularity, or other factors to produce more accurate absolute assessments of pulmonary functionality.

In a still further embodiment of the present invention, the software of the apparatus 10 is able to ingest data from other existing static imaging systems such as MRI, CT, or ultrasound for use in determining the shape and size of a particular individual's lungs and associated respiratory chamber dimensions to increase the accuracy of respiratory measurements. Two-dimensional and three-dimensional information obtained from other imaging systems may be ingested and adapted to the specialized model and correlated to the apparatus 10.

In an alternative embodiment, where it is desirable to collect information concerning both cardiac and pulmonary functionality, the apparatus 10 and method of the present invention include guidelines for antenna placement. FIG. 10 illustrates an embodiment comprising at least one sensor 20 positioned adjacent a subject's sternum to capture both cardiac and pulmonary information. Sensor 20 placement can be an important parameter and can affect the strength of received reflections S'. To support simultaneous collection of both cardiac and pulmonary information, including stroke volume and tidal volume, respectively, a sensor 20 is placed adjacent the subject's sternum within a prescribed radius G. Generally, it is preferable that the sensor 20 be placed within a radius G of 3 centimeters from the midpoint of the sternum at a point just below a line intersecting the subject's nipples. A sensor 20 may be placed at other locations, and need not be placed in close proximity to the center of the sternum, to capture cardiac and pulmonary rhythm and rate information. For example, as shown in FIG. 12, in one embodiment of the present invention, a sensor may be placed under the left arm or on one's back and still obtain data to track and monitor both cardiac and respiratory rate and rhythm.

Referring to FIG. 10, in a preferred embodiment of the present invention where it also desirous to collect cardiac data including stroke volume, the sensor 20 is placed in close proximity to the subject's sternum rather than on the side chest wall. This placement provides a consistent calibration approach to maximize the resolution and accuracy of the interrogation process. Additional attenuation of the cardiac signal will be experienced in an underarm case due to the increased distance of the sensor 20 from the heart. However, in the present invention, as shown in FIGS. 2, 3, 12 and 13, one or more sensors 20 may be placed anywhere about the thorax and abdominal regions, including the lower back, to collect data indicative of pulmonary function, including respiratory rate and rhythm. Many of these same locations will also deliver cardiac rate and rhythm information. Although the present invention contemplates that the transmit and receive antennae 30, 40 will be integrated with other sensor 20 elements as one unit, the antennae 30, 40 may be deployed separately from the other sensor 20 elements.

Referring to FIG. 10, in greater detail, when both cardiac and pulmonary data are desired, including cardiac stroke volume and respiratory tidal volume, a preferred position for the sensor 20 and its antennae 30, 40 is on the subject's chest within a radius G of approximately 3 centimeters from the center of the subject's sternum.

As illustrated in FIGS. 12-15, additional embodiments of the present invention include multi-sensor arrays deployed in close proximity to the targeted areas, such as the upper, middle, and lower lobes of the lungs with both anterior (adjacent the chest) and posterior (adjacent the back) placement, thereby delivering additional data that can be integrated via the model to provide a more accurate measure of instantaneous lung volume.

13. Sensor Targeting Functionality

In a still further embodiment of the present invention, the apparatus 10 includes a targeting element that allows the primary signal from each sensor 20 to be directed to a key focal point within the respiratory chamber 70 to maintain consistent and accurate measurements. This feature considers adjustments to each model required to accommodate the fact that the lungs may change position and orientation with respect to the antennas 30, 40 during the respiratory cycle. The apparatus 10 automatically and continually adjusts the direction of the transmitted signal using mechanical or electrical means to maintain a consistent view of the focal target area T of the lungs or respiratory chamber 70, and, makes appropriate adjustments to the perceived volumetric changes by integrating the dynamic behavior of the lungs during the respiratory cycle. This targeting element also assists in maintaining accurate measurements when motion may be induced by the subject.

14. Adaptive Modeling and Simulation Methods

Figure 19:
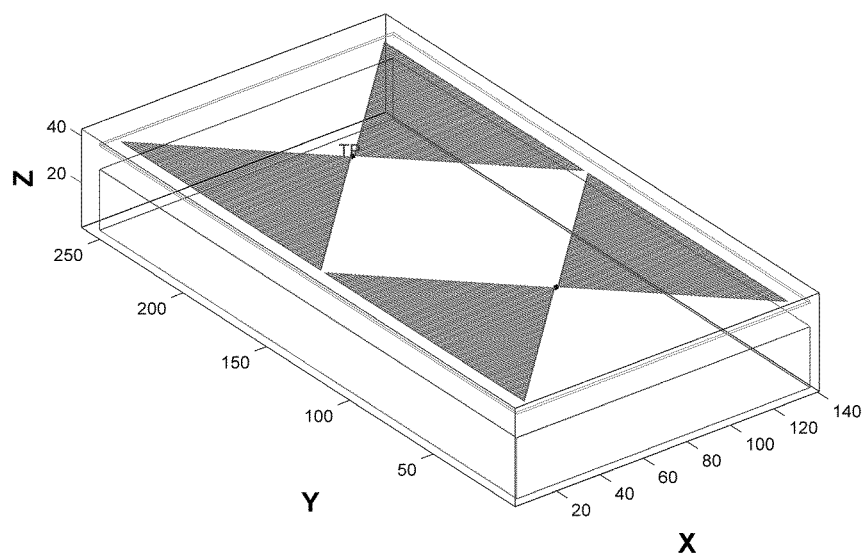
FIG. 19 is a perspective view of a Bowtie antenna model, according to the present invention.
Figure 20:
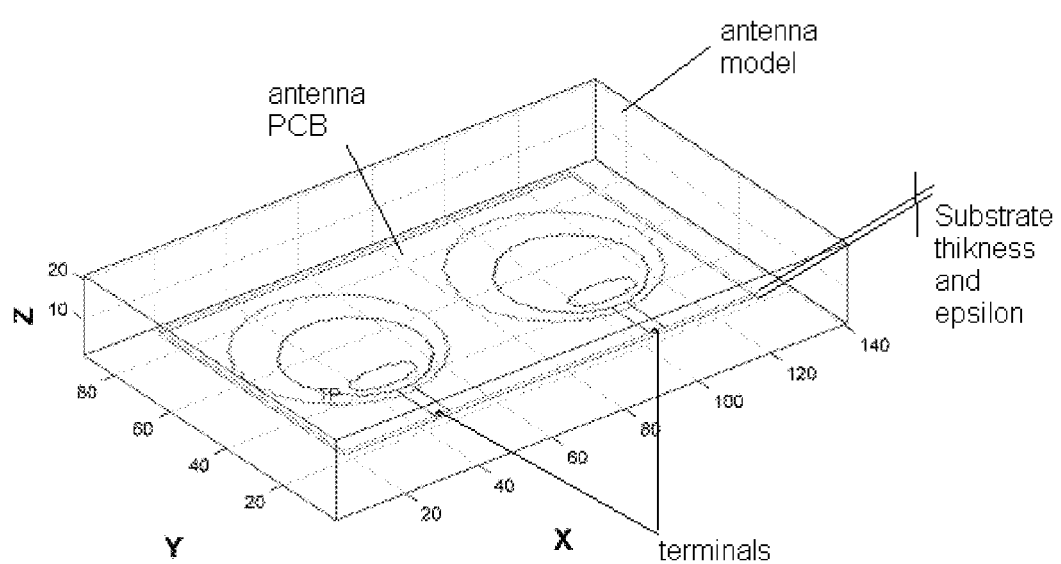
FIG. 20 is a perspective view of an SEE antenna model, according to the present invention.
Figure 23:
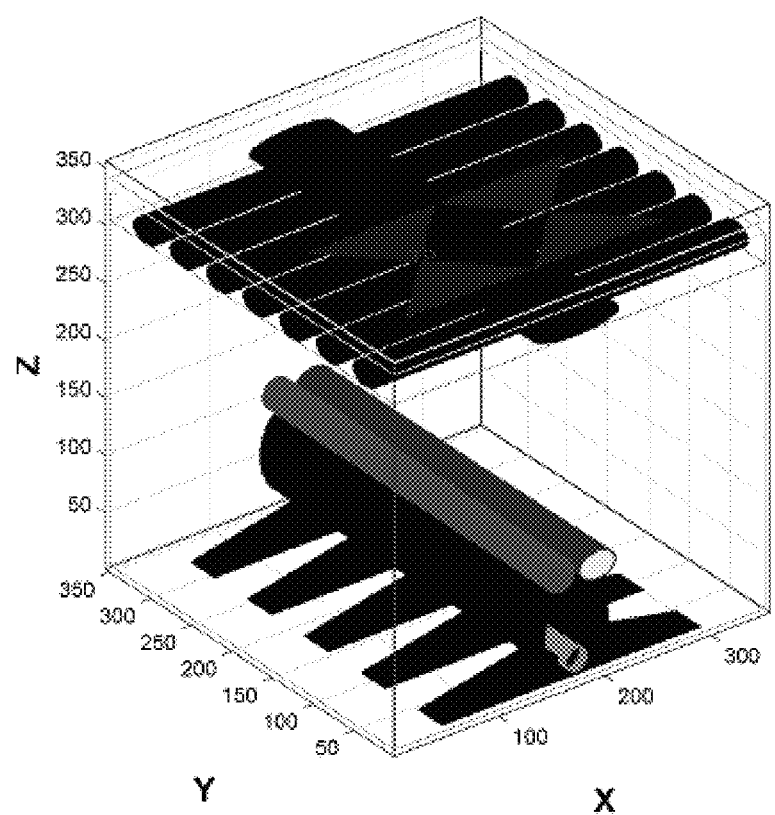
FIG. 23 is an exemplary FDTD model of the chest cavity without lung or heart with a bow-tie antenna, according to an embodiment of the present invention.
Figure 26:
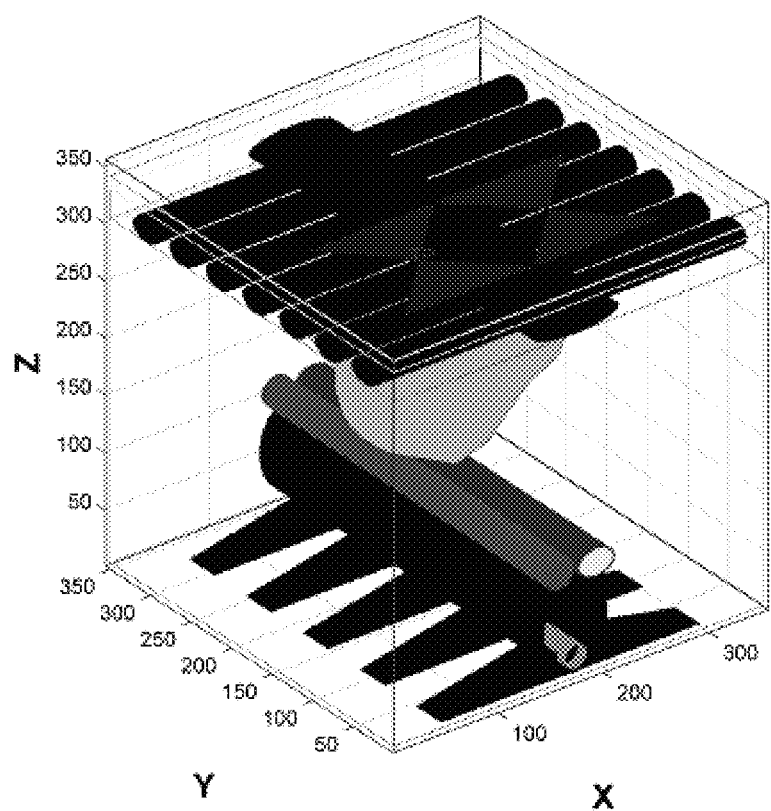
FIG. 26 is an FDTD model of the chest cavity including the heart with a bow-tie antenna, according to an embodiment of the present invention.

In another embodiment, the present invention provides adaptive respiratory modeling and simulations methods. These methods include development of an FDTD simulation protocol for tracking pulmonary functionality comprising the steps of:

1) creating a 3-dimensional model of antenna structures used in the apparatus (FIGS. 19 and 20);

2) creating a 3-dimensional model of the lungs and surrounding thoracic and abdominal region that is representative of the human anatomical structure with associated complex electrical properties for the various tissue types (FIGS. 23 and 26);

3) creating a simulation of respiratory chamber functionality, including starting from a respiratory chamber volume corresponding to maximum inflation, stimulating the system model using a single cycle Gaussian pulse with zero mean as the excitation source; then repeating the simulations, decreasing the respiratory chamber volume in incremental steps until minimum respiratory chamber volume is reached;

4) applying a novel software and hardware signal processing system to analyze the resultant data and determine algorithmic adjustments to accurately detect changes in respiratory chamber volume, including, comparing received reflections across a range of respiratory chamber volumes to quantify differences observed, and, correlation with ranges of the UWB receiver.

Referring to FIG. 4 and FIGS. 16A and 16B, the present invention includes a process for refining and tuning its own algorithmic processes to support accurate, calibrated operation of the apparatus 10. First, finite difference time domain (FDTD) models of the lungs and chest are developed and applied based on both anatomic and complex dielectric data. The models provide a variety of sizes, shapes, granularities and aggregate configurations to deliver a thorough representation of expected patient and subject physiologies and encompass the expected standard anatomical variation in the population. The present invention also provides for the use of models specific to a particular subject, wherein that model may be derived from other imaging technologies, such as magnetic resonance imaging, X-ray, ultrasound, infrared or other methods for determining model configuration and geometry.

The volumetric model associated with a defined respiratory chamber 70 of the present invention is designed and configured to provide an accurate assessment of respiratory function. In one version, a single volumetric model is used to provide an assessment of respiratory function. In another version, one or more smaller volumetric models are developed wherein each model is associated with a specific target interrogation volume 60. Each target interrogation volume will encompass a defined respiratory chamber 70 which describes the volumetric model associated with the analytical process of the present invention for that specific interrogation volume 60. Each of the smaller volumetric models and their respective respiratory chambers 70 may then be aggregated to create an integrated volumetric model supported a larger and more complex aggregate respiratory chamber 70. Each volumetric model is comprised of a volumetric voxel mesh composed of a set of small cubic cells. Each cubic cell is defined by both its size and several complex electrical properties associate with the cell. Each volumetric model is also defined by a minimum mesh size which is based on the shortest operational wavelength for the ultra-wideband signals S generated by the apparatus 10. The minimum mesh size used in each volumetric model is determined according to the relationship provided in Equation 1, below:

$$MeshSize_{minimum} = \frac{\lambda_{minimum}}{20\sqrt{\varepsilon r}};$$

$$\lambda_{minimum} = \frac{c}{Frequency_{maximum}}$$

Equation 1

Where:
∈r is the relative dielectric constant of the medium through which the transmitted signal must propagate;
c is the speed of light ($3\times10^{10}$ cm/sec)
$Frequency_{maximum}$ is the highest frequency of interest in the transmitted signal in Hz;
$\lambda_{minimum}$ is the corresponding shortest operational wavelength for the transmitted ultra-wideband signals measured in centimeters;
20 is the constant used to ensure the mesh size of the model will be significantly smaller than the minimum wavelength to ensure the mesh size is an accurate dimension for simulation purposes.

A three-dimensional structural model of the aggregate respiratory chamber 70, comprised of one or more interrogation volumes 60 and one or more respiratory chambers 70, corresponds to certain UWB radar requirements providing a foundation for application of multiple functional dynamic models, based on nonlinear mesh deformation using dynamic models of a respiratory chamber 70 indicative of lung functionality. Respiratory models representing total respiratory volumes are integrated as components of the invention.

The respiratory model is tailored to the requirements of the UWB radar of the apparatus 10 to provide sufficient corresponding resolution to support respiratory volumetric analysis. Additional variables influencing the signal returns to the apparatus 10 from the respiratory chamber 70 are integrated in the algorithmic elements of the apparatus 10. The model includes a process for the interrelation of complex electrical properties for individual tissues and organs found in the human chest. The table below lists various anatomical structure and associated complex dielectric values used in the FDTD models associated with the invention where Epsilon (∈) is the gross permittivity of the tissue and Sigma (σ) is the conductivity of the tissue. The model further includes functionality within the algorithm to adapt the values of Epsilon (∈) and Sigma (σ) to the specific frequency spectrum of the UWB signal applied to the tissue encountered in an interrogation volume 60. This model may also be adapted to support other frequencies of electromagnetic energy applied to the tissue higher than 10 GHz. However, the present description focuses on that frequency window between 3.1 GHz and 10.6 GHz, the spectrum made available by the FCC for medical imaging.

TABLE 1

Complex Dielectric Constants for Various Human Structures

| Anatomical Structure | Epsilon (∈) | Sigma (σ) |
|---|---|---|
| Bone | 12.4 | 0.2 |
| Fat | 4.72 | 0.05 |
| Muscle | 60 | 1.32 |
| Skin | 9.9 | 0.72 |

TABLE 1-continued

Complex Dielectric Constants for Various Human Structures

| Anatomical Structure | Epsilon (ε) | Sigma (σ) |
| --- | --- | --- |
| Lung | 20.5 | 0.42 |
| Heart | 57.48 | 1.22 |
| Trachea | 55.9 | 1.12 |
| Cerebra Spinal Fluid | 68.1 | 2.45 |
| Esophagus | 71.1 | 1.35 |

The model of the present invention also includes optimized antenna configurations responsive to the dielectric values of the anticipated tissues to provide desired signal transmissivity and reception. The optimized antenna configurations ensure that the signals penetrate sufficiently in the desired interrogation volume to support calculation of instantaneous respiratory chamber volume. The optimum antenna design supports application where the antenna is in close contact with a high dielectric material, such as skin or cloth, and, the direction of signal propagation is into the high dielectric material, and, into the subject's body. Other embodiments may be based on placement of a sensor 20 some distance from a subject's skin, adding another dielectric variable associated with the air space between the sensor 20 and the subject's skin. Still further embodiments may be based on placement of a sensor 20 outside of an enclosed area to monitor the respiration of a person or persons within this enclosed area. And, still further, the enclosed area may be a mother's womb and the subject whose respiration is being monitored is the fetus in the mother's womb. Still further, the present invention may be adapted to noninvasively monitor both cardiac and respiratory function of the fetus while also monitoring the cardiac and respiratory function of the mother.

Referring to FIG. 4, in one version, the apparatus 10 of the present invention comprises a sensor 20 including a transmitting antenna 30 and an identical receiving antenna 40. The transmitting antenna 30 transmits UWB radar pulses S and the receiving antenna 40 collects reflections S' from the target area T encompassed within the interrogation volume 60 and including the associated respiratory chamber 70.

FIG. 19 is an illustration of a version of the invention comprising two identical antennas 30, 40 having a Bowtie structure. Additionally, FIG. 20 provides an illustration of an alternative embodiment comprising a single element elliptical (SEE) antenna structure. The antenna configurations need not be limited to these two types. A system may include antennas that are not identical but have been sized and tuned to either more efficiently transmit the signals S, or, to receive the reflected signals S'. These alternative antenna configurations may be ingested and adapted for use in the algorithms and methods of the present invention.

Operational parameters and specifications of the bowtie antennae and SEE antennae used in versions of the present invention are provided in Table 2 below.

TABLE 2

Antenna Parameters

| Parameter | Bowtie Antenna | SEE Antenna |
| --- | --- | --- |
| Frequency Range ($R_L$ > 10 dB) | 1 GHz to 8 GHz | 3 GHz to 8 GHz |
| Physical Dimensions | 60 mm long × 60 mm wide | 57 mm long × 33 mm wide |
| Feed | Center | End |

In a preferred embodiment, the present invention uses Bow-tie antennas rather than SEE antennas due to enhanced reflections S' from the signals transmitted by the Bow-tie antennas. As illustrated in FIGS. 19 and 20, the bow-tie antenna is physically larger and has improved directivity when compared to the elliptical antenna. In addition, the bow-tie antenna uses a start frequency of 1 GHz, while the SEE antenna uses a start frequency of 3 GHz. Lower frequency energy is less readily absorbed by the interrogated tissues as compared to higher frequency energy. The bow-tie antennae use a spectrum with a larger lower frequency component, resulting in stronger received reflections S'. Consequently, in a preferred embodiment of the present invention, the antenna is a bow-tie antenna using a starting frequency of 1 GHz. However, to comply with existing regulatory requirements, such as the currently authorized FCC spectrum for UWB medical imaging of between 3.1 GHz and 10.6 GHz, another preferred embodiment uses an SEE antenna illustrated in FIG. 20, having a starting frequency of 3.1 GHz.

The present invention also provides for the modification of multiple parameters to support improved calibration. For example, in one version, a transmitted pulse shape is chosen to produce a transmitted frequency spectrum that complies with the UWB medical frequency band as defined by the United States Federal Communications Commission (FCC) in Rule & Order 02.48.

The model of the present invention supports the inclusion and manipulation of the value of variable parameters associated with the model. Following are descriptions of certain of those parameters along with discussion of possible modifications supported by the present invention.

Figure 21:
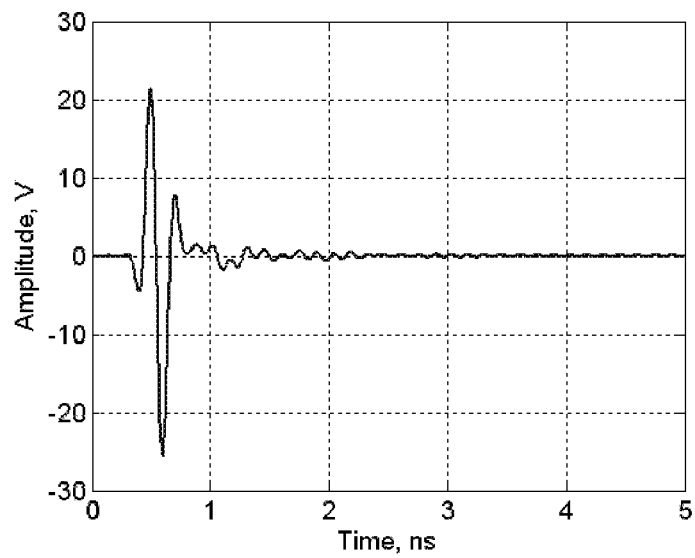
FIG. 21 is a chart illustrating the typical amplitude of a transmitted signal, according to an embodiment of the present invention.
Figure 22:
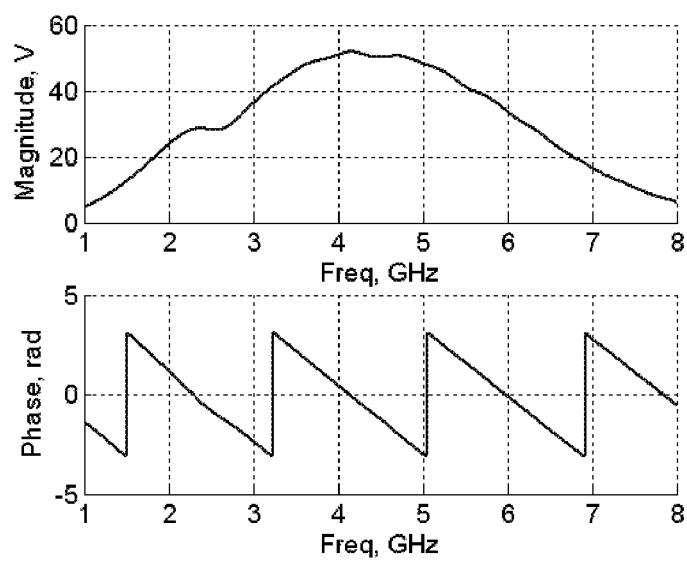
FIG. 22 is a chart illustrating the typical spectrum of the transmitted signal of FIG. 21, according to an embodiment of the present invention.

FIG. 21 illustrates a simulated transmitted pulse or signal S as viewed in the time domain; FIG. 22 illustrates the corresponding magnitude and phase of the same transmitted pulse S in the frequency domain. The present invention supports the comparison of results from two tests to calibrate the model based on the yield of quantifiable differences in received signals S'. One skilled in the art will recognize that the power and shape of the transmitted pulse S may be modified to improve precision and accuracy of measurement. For example, in another version, the power of the transmitted signal S may be increased beyond that generally allowed under the FCC guidelines to improve transmitted signal S penetration depth or to enhance the energy of reflected signals S'. Additionally, one could increase or lower the frequency of the transmitted signals S to minimize absorption or increase resolution.

FIG. 23 is an illustration of a basic structure of a three-dimensional anatomical model of the thoracic area associated with the algorithm and method of the invention without the inclusion of the lungs or heart but with a pair of bow-tie antennas positioned over the sternum. In addition to adjustments of mesh size of the model in correlation to signal frequencies, the resolution of the three-dimensional model may adjusted to provide increased or reduced granularity. This granularity is also driven by the selected mesh size. Further, empirical data from other imaging systems may be ingested within the model to provide a highly resolute image of a subject's anatomy in the thoracic area. Still further, the apparatus and method of the present invention may be first calibrated against other known measurements methods to ensure accuracy and reliability.

Figure 24:
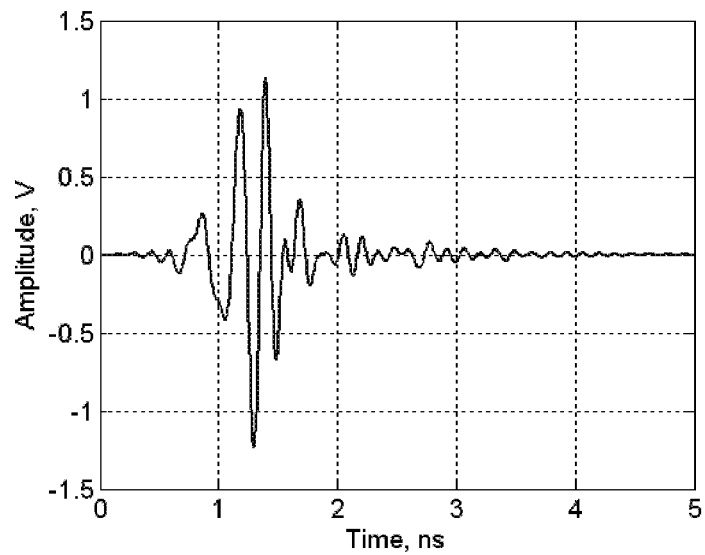
FIG. 24 is a chart illustrating a simulated received signal without lung or heart, according to an embodiment of the present invention.
Figure 25:
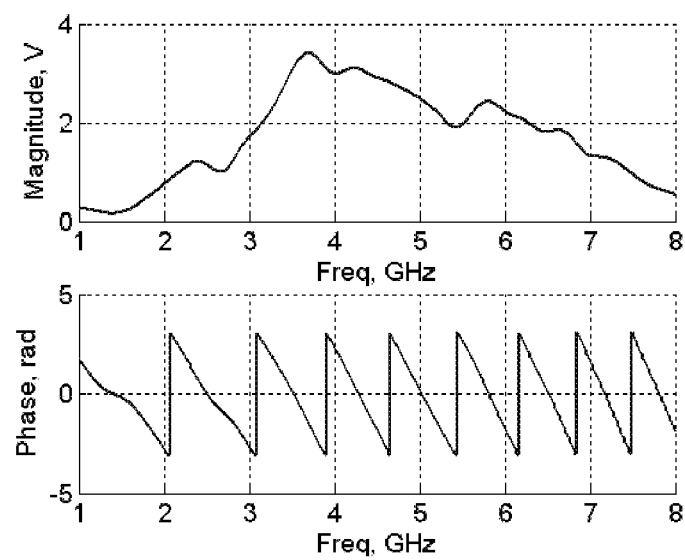
FIG. 25 is a chart illustrating corresponding magnitude and phase of the simulated received signal of FIG. 24, according to an embodiment of the present invention.

FIG. 24 provides an illustrative example of received reflections S' from this model as viewed in the time domain; FIG. 25 provides an illustrative example of the corresponding magnitude and phase of the received reflections S' in the frequency domain. The received signal S' has a large initial component resulting from direct coupling between the two antennae 30, 40. In contrast to the symmetrical spectrum of the transmitted pulse S, the energy of the received spectrum is concentrated in the lower frequencies since human tissue tends to absorb more of the energy of the higher frequencies. Consequently, in certain circumstances where increased signal penetration is desirable, signal frequencies may be lowered, or, signal energy increased.

FIG. 26 illustrates a basic structure of the anatomical model of the present invention including the heart with a pair of bow-tie antennas positioned over the sternum. For clarity, the lungs are included in the model but not shown in FIG. 26. Although shown in this particular embodiment as positioned over the sternum adjacent the heart, to acquire data representing respiratory rate and rhythm, one or more of the antenna pairs 30, 40 may be placed anywhere around the periphery of the thorax and abdomen since anatomical motion derivative of respiration is present throughout this region. This motion can be qualitatively and quantitatively measured by targeting one or more anatomical elements which move in correlation with the respiratory cycle, including the ribs, internal and external intercostal muscles, abdominal muscles, the diaphragm, lungs, and chest wall. Again, the resolution and accuracy of the model can be enhanced by using empirical data from other imaging systems to more closely match the actual shape of various anatomical elements within a subject's thorax.

Figure 27:
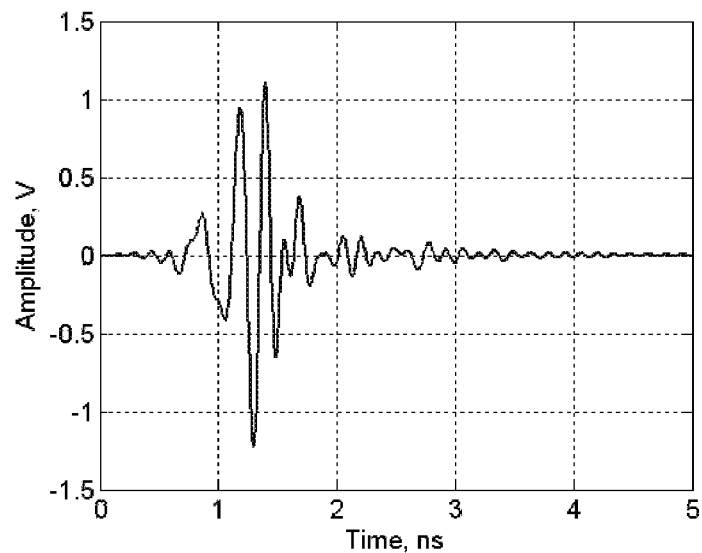
FIG. 27 is a chart illustrating a simulated received signal with the heart and lungs, according to an embodiment of the present invention.
Figure 28:
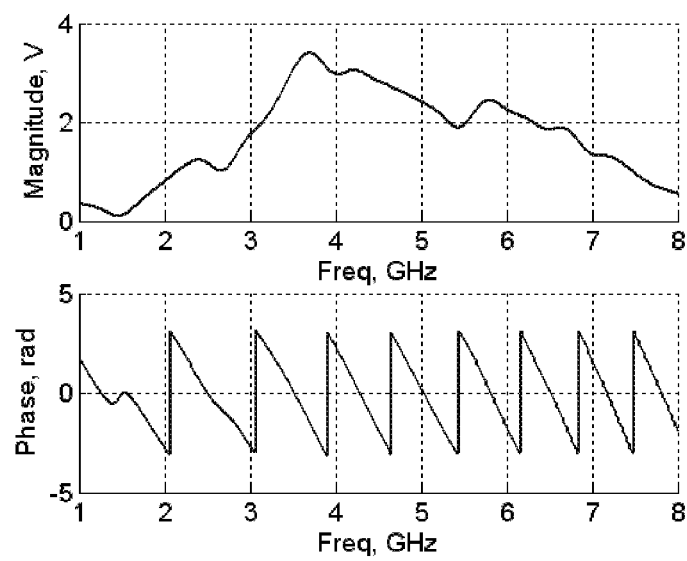
FIG. 28 is a chart illustrating corresponding magnitude and phase of the simulated received signal of FIG. 27, according to an embodiment of the present invention.

FIG. 27 illustrates simulated received reflections S' for a case with the heart and lungs included as viewed in the time domain; FIG. 28 illustrates the corresponding magnitude and phase of the frequency spectrum for the received signal S'.

Figure 29:
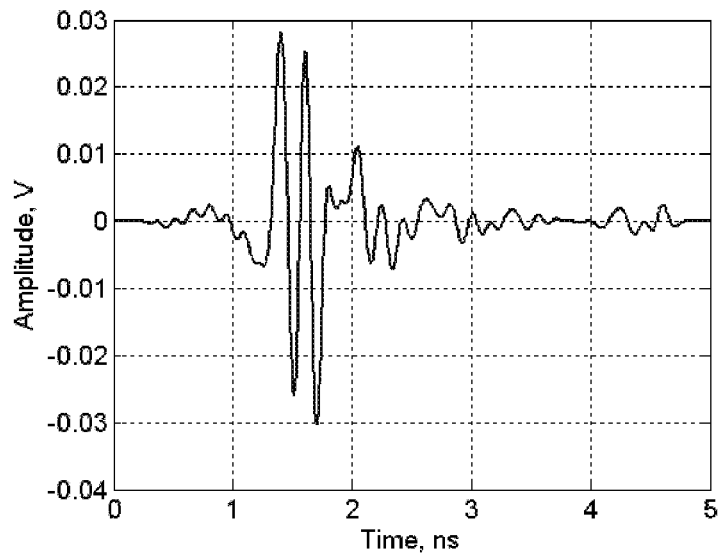
FIG. 29 is a plot of a simulated time domain difference signal calculated by subtracting data derived from the test case with the heart and lungs from data derived from the test case without the heart and lungs, according to an embodiment of the present invention.
Figure 30:
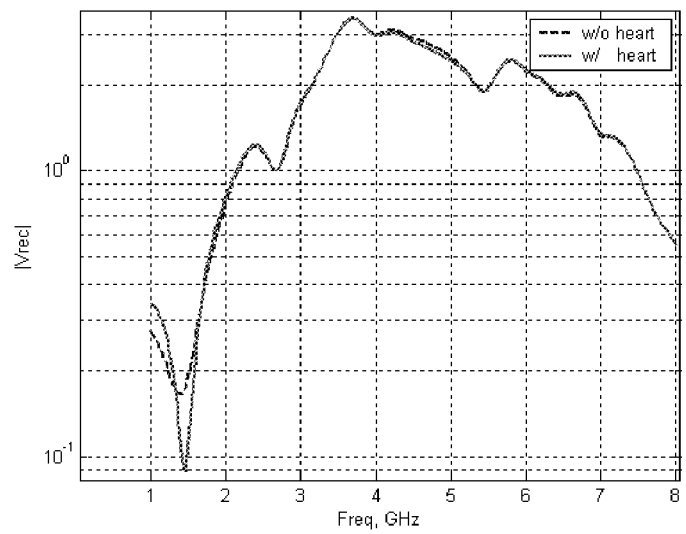
FIG. 30 is a plot of the simulated corresponding spectrum of the time domain difference signal illustrated in FIG. 29, according to an embodiment of the present invention.

FIG. 29 provides an illustrative plot of the expected time domain difference signal calculated by subtracting the data derived from the case with the heart and lungs from the data derived from the case without the heart and lungs. For example, the amplitude of the difference signal is 0.058 Vp-p as compared to the 2.35 Vp-p amplitude exhibited by both of the two received signals; a difference of 32.2 dB, establishing an expected minimum sensitivity of the receiver for detection of gross anatomical details based on the simulations. FIG. 30 illustrates the corresponding spectrum of the received signals for the two cases.

The present invention further includes a respiratory-specific algorithm addressing heretofore-unknown behavior where, as the difference in respiratory chamber volume increases, the length of the difference signal increases. This relationship is a fundamental aspect of the method and process of the present invention used in determining instantaneous respiratory chamber volume (IRV). The delay between a transmitted pulse S and the beginning of a received reflection S' is determined by the finite distance between the antenna plane and the target respiratory chamber wall or tissue interface. Differences in respiratory volume are presented in a quantifiable form by the computation of the energy of the recorded signal waveform through numerical integration using the following relationship:

$$W = k \cdot \int_0^T s^2(t) dt;$$

where k=normalization factor and T=5 nanoseconds, the receiver time window.

Increases in reflected energy correlate with larger differences in chamber volumes, indicating the ability of the apparatus to measure variations in the volume of targeted portions of the human lung.

15. Instantaneous Respiratory Volume Modeling Method

The various methods of the present invention further include a method for determining instantaneous respiratory volume. This feature is built upon the versions and embodiments of the present invention capable of monitoring respiratory rate and rhythm, and, cardiac rate and rhythm. Fundamentally, the instantaneous respiratory volume (IRV) module of the present invention supports the noninvasive acquisition of real-time respiratory volume without dependence on more complex, invasive methods, such as a plethysmograph, among others.

Figure 31:
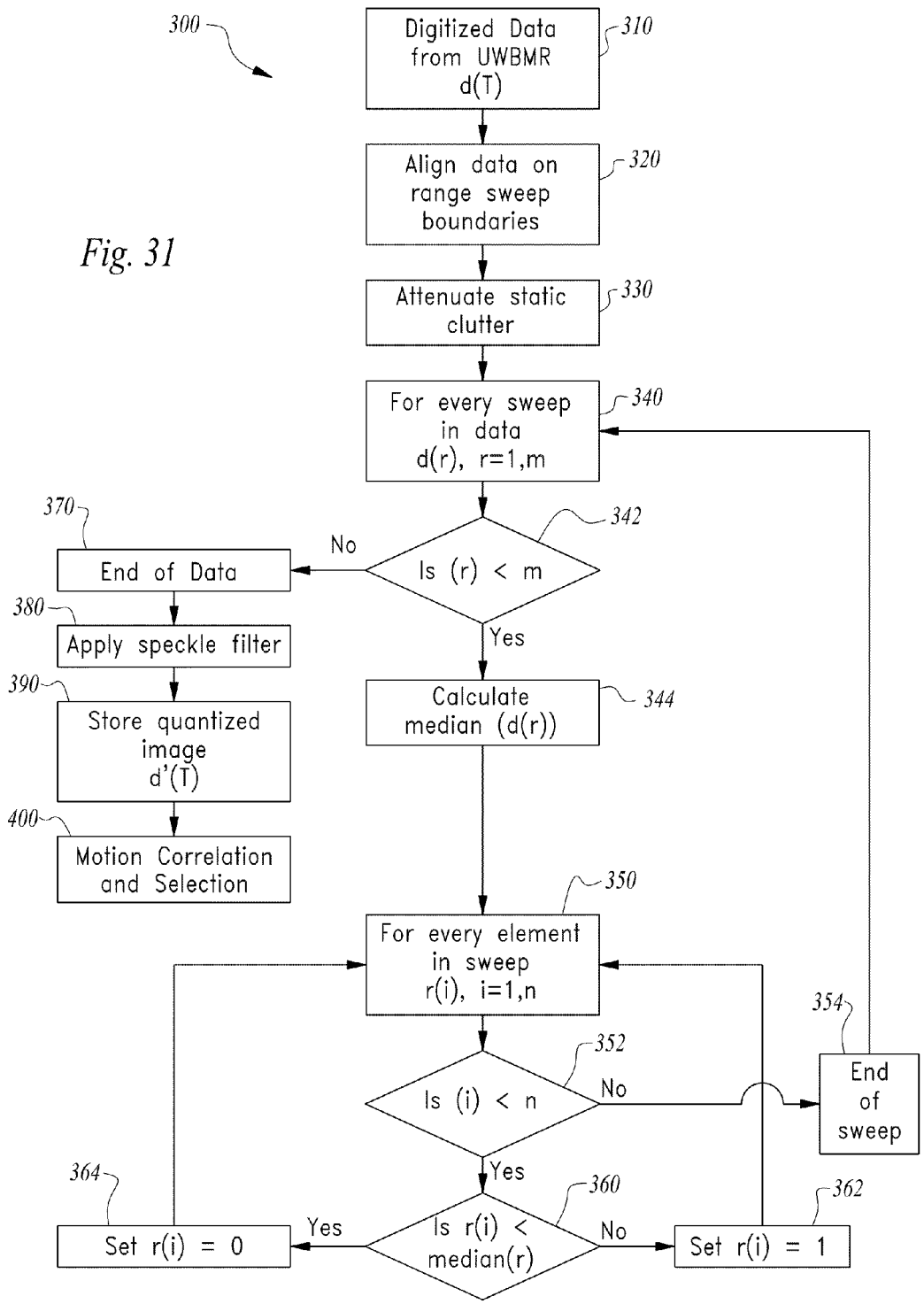
FIG. 31 is flow chart illustrating the process and algorithm of the pulmonary image quantizer of the apparatus, according to an embodiment of the present invention.
Figure 32:
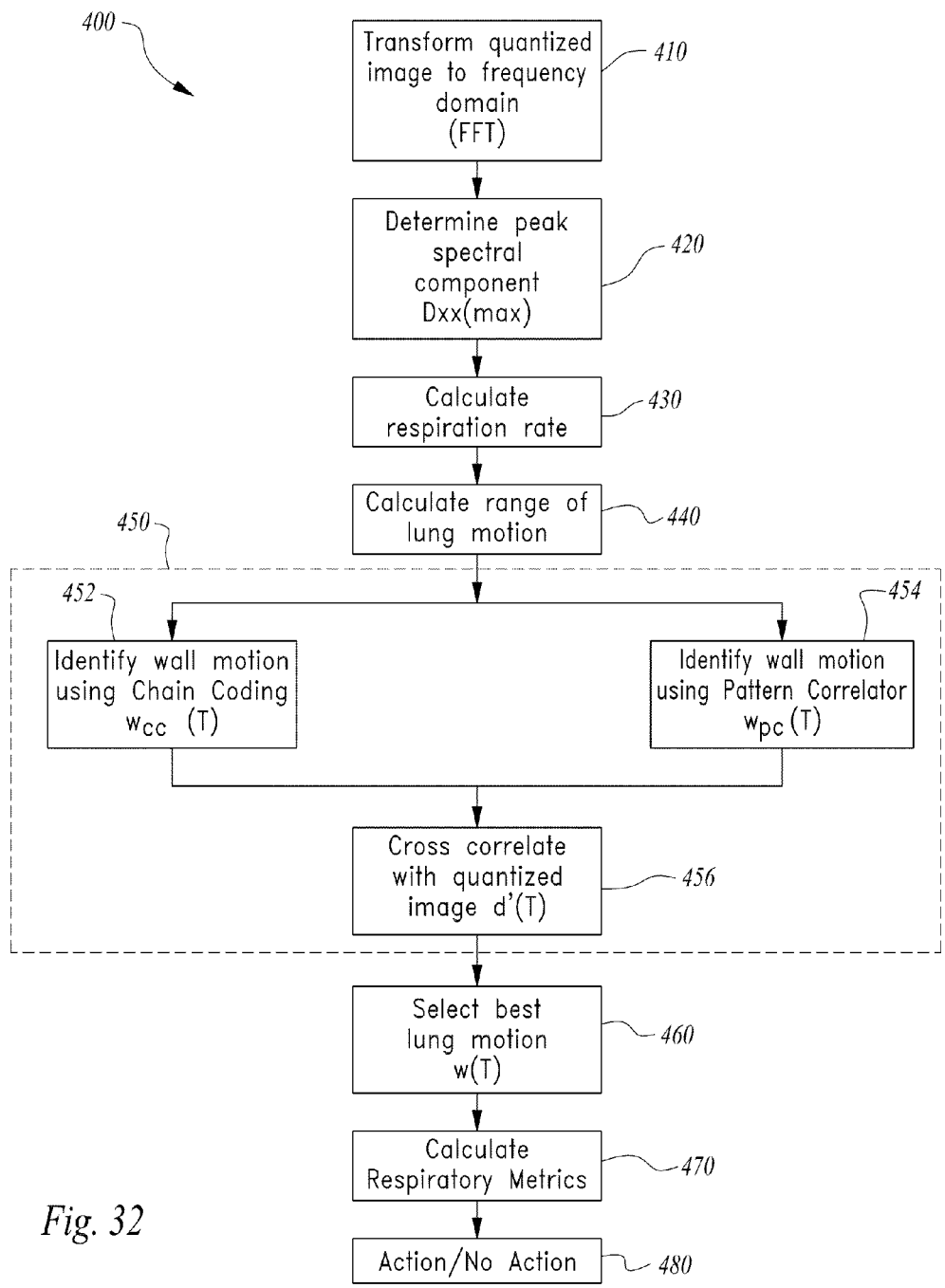
FIG. 32 is a flow chart illustrating the process and algorithm of the pulmonary boundary motion detector and metric determination algorithm of the apparatus, according to an embodiment of the present invention.

FIG. 31 is a flow chart of the process and algorithm of the pulmonary image quantizer module 300 of the present invention used in determining instantaneous respiratory volume (IRV) and other pulmonary metrics. FIG. 32 is a flow chart of the process and algorithm of the pulmonary motion detection and metric determination module 400 used in determining IRV and other pulmonary metrics. The results of the image quantizer process 300 of FIG. 31 are cross-correlated against the results of the motion detection process 400 of FIG. 32 in an interactive process to identify and isolate respiratory chamber wall movement to support determination of IRV, tidal volume and other respiratory metrics. Consequently, the apparatus and method of the present invention are then able to obtain and calculate pulmonary metrics, such as tidal volume and instantaneous respiratory volume, which heretofore have required the use and application of invasive and cumbersome instrumentation and devices.

References will be made to FIGS. 4 and 5 in this portion of the description to support the reader's understanding of various aspects of the apparatus and method which support the processes illustrated in FIG. 31 and FIG. 32. Now, with reference to FIG. 4 and FIG. 5, for calculation of instantaneous respiratory volume, the ultra-wideband medical radar (UWBMR) 54 of each sensor 20 transmits radar signals S toward the target area T and radar reflections S' are then first received by the receiving antenna 40 and converted to digital radar reflections.

FIG. 31 is a flowchart describing the binary image quantizer process 300 associated with the apparatus and method of the invention. First, digitized data from the ultra-wideband medical radar (UWBMR) 54 is collected continuously over time 310. The received raw radar reflection data S' from each sensor 20 indicating motion is then aligned on range sweep scan boundaries 320. The aligned data is then passed through a series of high pass filters to remove or attenuate both static clutter (reflections from inanimate objects) and lower frequency noise 330. The resultant motion data is then amplified and quantized to produce an interim black/white image 370. Next, a speckle filter is applied to remove random speckle noise 380. The removal of the random spectral frequencies highlights features in the remaining image. The quantized image is then stored 390 for subsequent reference in the motion detection and characterization algorithm and method 400 illustrated in FIG. 32.

The filtering step to attenuate static clutter 330 permits better discrimination of the targeted area associated with each sensor 20 and easier automatic image segmentation. In addition, after the image for a sensor 20 has been filtered, other classical techniques are employed to more highly discriminate the sensor target area T, including, but not limited to, contrast improvement, edge enhancement, spatial filtering, noise suppression, image smoothing, and image sharpening.

Once static clutter has been attenuated, for every data sweep, the median value of the bounded white section for each sensor is calculated for every row in the image and the minimum and maximum bin numbers for every respiratory cycle are calculated 340. The difference in the maximum and minimum bin numbers is multiplied by the spatial resolution of the system to obtain the change in the radial axes between maximum and minimum lung inflation.

Now, in greater detail, with continued reference to FIG. 31, the digital radar reflections S' are stored in memory as received over time 310. The digital radar data is then range aligned on sweep boundaries 320. The aligned data is then passed through a series of high pass filters to minimize low frequency noise and attenuate static clutter, such as reflections from any inanimate objects within the range of interest 330. The resultant data associated with all anatomical motion in the range of interest, including respiratory motion and the associated movement of parts of the anatomy, e.g., ribs, diaphragm, lungs, pleural cavity, abdominal muscles, and, chest wall, is then amplified and coarse quantized using a binary quantizer where the quantizer threshold for a given sweep or row is based on the median value of the data set, resulting in an intermediate black and white image for each sensor 20. Depending on the specific anatomical motion selected for monitoring, other statistical portions of the data set may be selected for image creation. After creation of the data underlying the initial image 370, a speckle filter is applied to the image to remove random speckle noise and increase the sharpness of the image boundary edges 380, supporting accurate determination of spatial change over the target range T comprising the interrogation volume 60 and respiratory chamber 70. For example, a speckle filter having a 3×3 kernel may be applied, but other speckle filters could be applied depending on the desired sharpness of the boundary edges, which would influence the accuracy of the assessment of spatial change. The filtered quantized image is then stored 390 for subsequent use in cross-correlation 400 with other motion detection processes in the pulmonary motion determination process and algorithm illustrated in FIG. 32.

The pulmonary image quantizer algorithm illustrated in FIG. 31 causes data from each sensor 20 to be successfully presented as an image space full of various spatial structures changing in time that represent both chest wall and other motion associated with respiration along with other non-respiratory based noise sources including other organs, bones, patient motion, and stray radiofrequency (RF) emissions. Referring now to FIG. 32, to further refine the collected and processed data, additional pulmonary metrics are calculated and integrated as part of the overall method of the invention to delineate and confirm that the structures found in the quantized image 390 are, in fact, anatomical elements associated with respiratory functionality and not caused by other undesirable signal sources. This confirmation ensures that measurements associated with these respiratory-influenced structures will be used to determine the instantaneous respiratory volume, tidal volume and other metrics. The data from each sensor 20 may be used individually or in aggregate to calculate the various pulmonary metrics. As more sensors 20 are deployed about an individual's upper body, as in any of the earlier described embodiments compromising multiple sensors 20, the granularity and accuracy of the respiratory measurements can be increased. However, the granularity and accuracy associated with the use of only a single sensor 20 may be sufficient in many cases to obtain the diagnostically-significant data to support the generation of the values for the desired metrics.

FIG. 32 illustrates the process and algorithm associated with the pulmonary motion detection and selection module 400, according to an embodiment of the invention. In a first step, the motion detection module 400 causes the stored image 390 produced by the pulmonary image quantizer module 300 of FIG. 31 to be transformed to a frequency domain 410. The motion detection module 400 determines the respiratory rate by converting the entire swept image space to a predetermined frequency domain using a Fast Fourier Transform (FFT) algorithm 410. The FFT algorithm identifies and isolates the image region (range bin) of the swept range containing the strongest respiratory signal or peak spectral component 420. Output from each sensor 20 may be used to cross-check data from every other sensor 20 to ensure that the respiratory rate is accurate. Hence, by using at least two sensors 20, the apparatus 10 of the present invention provides a cross-check function to ensure that the measured respiratory rate is correct. If the two sensors 20 do not report the same respiratory rate, the invention triggers an alert to notify the caregiver, a technician or the individual, that it appears that at least one sensor 20 has malfunctioned and the measured respiratory rate may be inaccurate. Consequently, as more sensors 20 are deployed, it becomes easier to confirm when any specific sensor 20 has malfunctioned, allowing both the image quantizer module 300 and the motion detection and selection module 400 to ignore data being received from a malfunctioning sensor 20. Once the peak spectral component has been determined 420, the module calculates the respiration rate 430. The respiration rate is then used to calculate the range of lung motion 440. In an iterative process 450, the module 400 then confirms measurements identifying wall motion by use of both a chain coding technique 452 and a pattern correlation technique 454. The wall motion identified from both techniques is then cross-correlated with the earlier quantized image 456. The motion detection and selection module 400 then selects the best lung motion 460 based upon this iterative cross-correlation. Once the best lung motion has been determined, the pulmonary motion detection and selection module 400 calculates the various pulmonary metrics of interest including, tidal volume and other derivative metrics 470. Based upon the values of the calculated metrics, the module 400 then determines whether any of several actions are warranted and triggers alerts, alarms or notices to appropriate resources for response 480.

Uniquely, while confirming the respiratory rate 430, the module and method of the present invention also determines the depth range containing the desired targeted respiratory motion, which is used in the development and assessment of additional important IRV module metrics, discussed below. As earlier discussed and illustrated in FIG. 16A, in an alternative embodiment of the present invention, one or more sensors 20 or antennae 30, 40 of the sensors 20 may be placed at various positions around the thorax and abdominal region to capture independent respiratory rate and rhythm data derived from one or more anatomical elements which move in correlation with the respiratory cycle, including the ribs, internal and external intercostal muscles, abdominal muscles, the diaphragm, lungs, and chest wall.

During the process of assessing and selecting pulmonary motion, a second metric developed by the pulmonary motion detection module 400 comprises the identification and verification of the completeness of each target interrogation volume 60 and the overall respiratory structure, the respiratory chamber 70, as it changes over time. As the lungs expand and deflate in a sustained and rhythmic fashion during each respiratory cycle, the pulmonary motion detection module 400 identifies and selects candidate signals from one or more sensors 20 for further analysis by capturing and prioritizing signals having minimum discontinuities, suggesting the expected signal is associated with the continuous rhythmic motion of respiration. In one version, the algorithmic process of the IRV module leverages a chain coding technique 452 in conjunction with structural morphological techniques or pattern correlation 454 to minimize signal discontinuities caused by noise loss, such as white noise. Each of the chain coding and pattern correlator techniques is juxtaposed and cross-correlated with the earlier quantized image 456.

A third metric developed by the pulmonary motion detection module 400 comprises continual and repeated identification and tracking of a respiratory-like motion characteristic in the candidate image space for each sensor 20. The desired motion characteristic best characterizes the approximate motion of the chest walls, lungs or other targeted anatomical element with each target respiration volume during respiration over time. A corollary, yet opposite and equally important component of this third metric comprises the isolation and avoidance of signals from each sensor 20 having a motion characteristic that is not indicative of chest wall, lung or other motion derived from respiratory cycle influence. Essentially, the algorithm eliminates from consideration those signals that are most likely generated by a non-respiratory signal source.

A fourth metric developed via the algorithmic process and method of the present invention of the pulmonary motion detection module 400 is the development of a correlation between (1) the time-domain characteristics for each sensor 20 of the isolated respiratory range bin identified in the first step to determine the respiratory rate metric with, (2) points identified in the image space calculated for each sensor 20 that represent minimum, maximum, and zero-crossing points of respiratory excursions in the image space of the sensor 20 encompassing the respiratory chamber, as identified by the second and third metrics, structure completeness and motion characteristics.

After processing raw data to generate results containing the above metrics, the image regions for each sensor 20 that meet the requirements of the above metrics are isolated and identified as good candidates likely indicative of respiratory motion and suitable and desirable for further analysis 460. Each image region is repeatedly evaluated and a final candidate image region is selected as the truest representation of instantaneous respiratory volume 460. This truest representation is the candidate having the strongest characteristics in all metrics. This candidate then becomes the current "truest" candidate until it is subsequently replaced by a "truer" candidate.

With the current truest candidate chosen, the algorithm of the pulmonary motion detection module 400 identifies and quantifies minimum and maximum respiratory excursions using the earlier collected data available from the assessment of the four key metrics discussed above. Then, with the minimum and maximum respiratory excursions determined for each sensor 20, the algorithm of the module 400 determines the actual physical lung displacement by measuring and counting the spatial pixels traversed from a min-point to a max-point of the respiratory waveform and multiplying the number of pixels by the resolution of the data acquisition device (DAQ), then aggregating and correlating the excursion for each of one or more sensors 20 to the selected geometric model for the lungs.

In a next correlation and aggregation step, the apparatus uses the algorithm and calculates the instantaneous respiratory volume (IRV) by calculating a representative volume based on the measured respiratory excursion distance from each sensor 20 and the defined respiratory chamber 70. This measured physical lung displacement for each sensor 20 is then applied to the selected geometric model of the lungs to determine instantaneous respiratory volume and tidal volume.

16. Software User Interface

Figure 33:
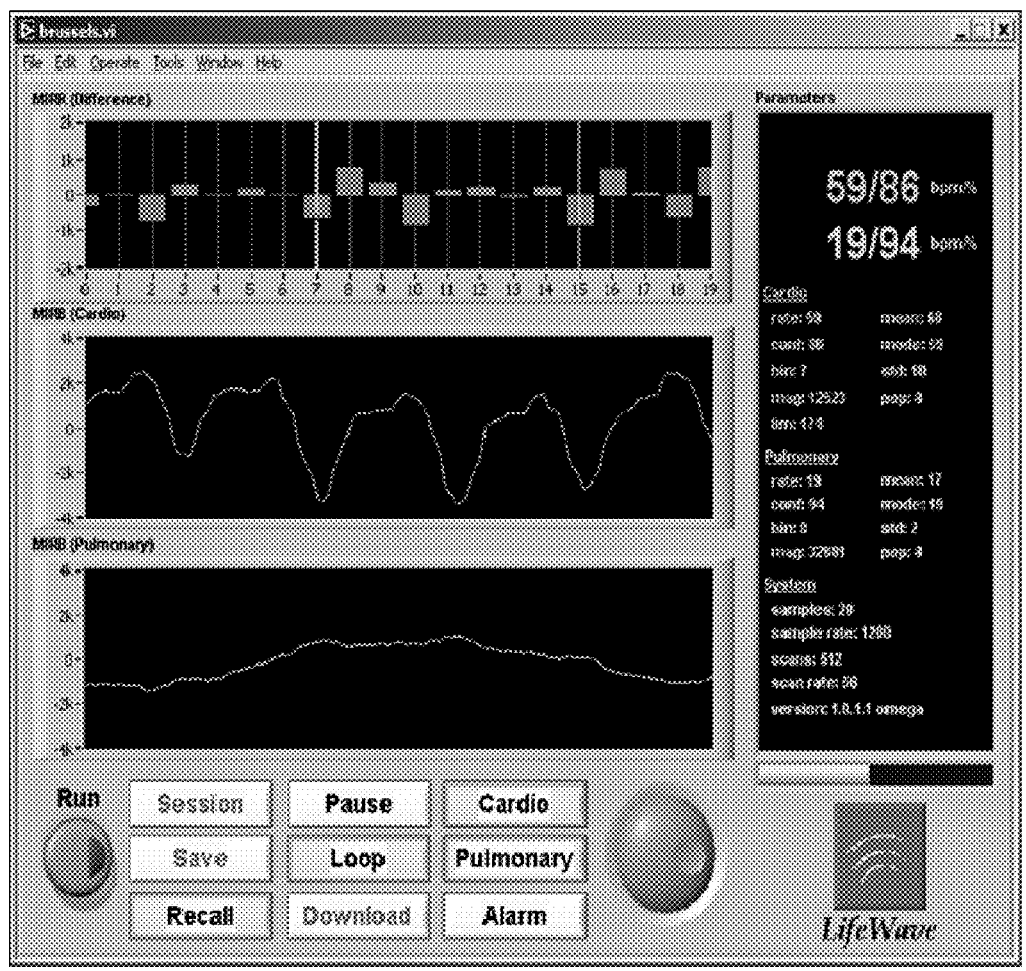
FIG. 33 is an illustration of the user interface of the software for real-time pulmonary trace isolation according to an embodiment of the invention.

FIG. 33 is an illustration of a user interface of the apparatus of the present invention, wherein the interface provides a real-time display of both pulmonary and cardiac rate and rhythm sensed by the sensor(s) 20. The interface allows a user to isolate and select various bins or depth segments associated with the interrogation volume 60 and respiratory chamber 70 to manually identify those traces presenting as having pulmonary features, or, cardiac features. The interface allows various filters to be applied to focus selection on either cardiac or pulmonary information. In addition, the interface provides a display of real-time cardiac and pulmonary rate, along with various trend metrics. In the example of FIG. 33, the user has identified bins 7 and 15 as having those features most indicative of cardiac and pulmonary behavior. The interface of FIG. 33 supports real-time data collection as well as real-time algorithmic adjustment to more readily capture target cardiac and pulmonary information from each sensor 20.

Figure 34:
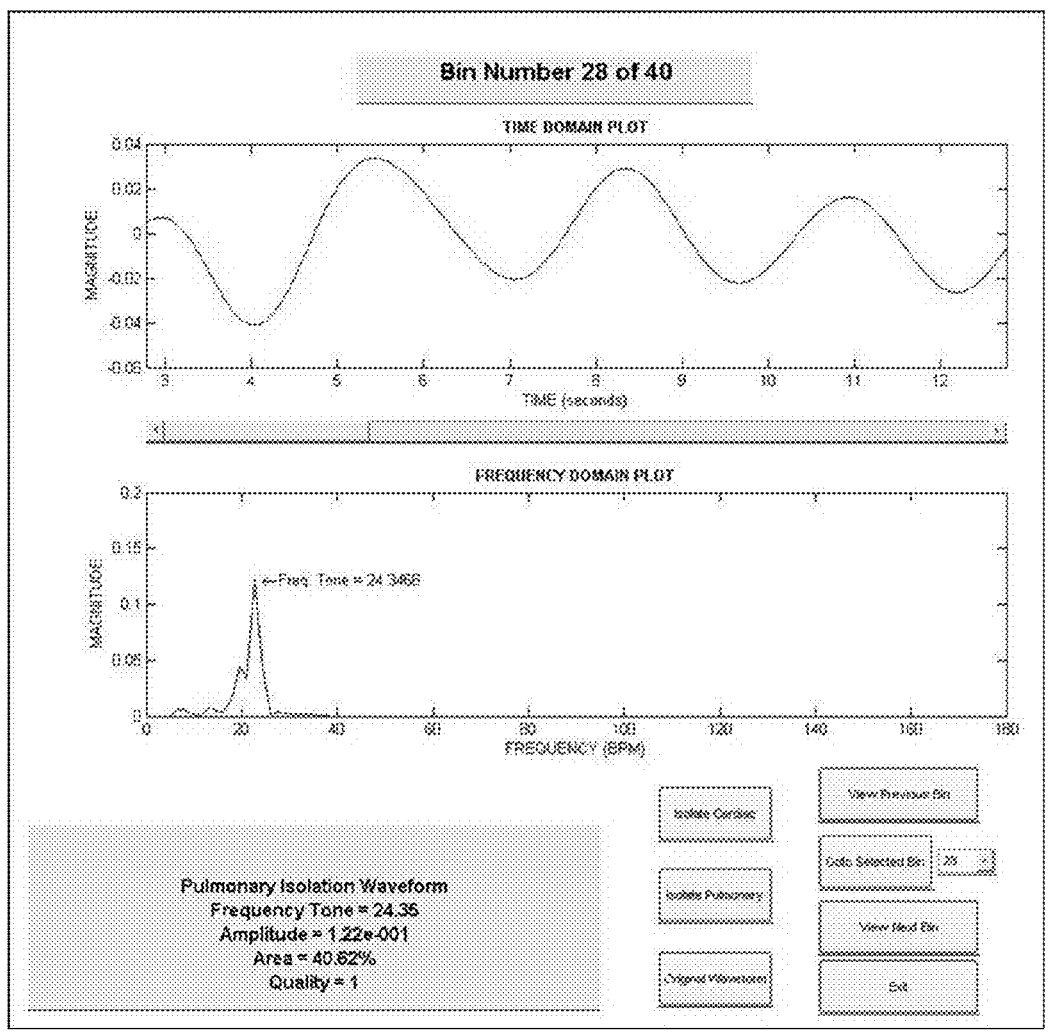
FIG. 34 is an illustration of the user interface of the software for post-processing pulmonary waveform isolation according to an embodiment of the invention.

FIG. 34 is an illustration of the software interface of the invention to support post-processing of collected data to isolate pulmonary and cardiac waveforms. This interface allows a user to perform detailed analysis of collected data and apply one or more filtering solutions to the method of the invention, subsequent to collection of data from a subject.

Figure 35:
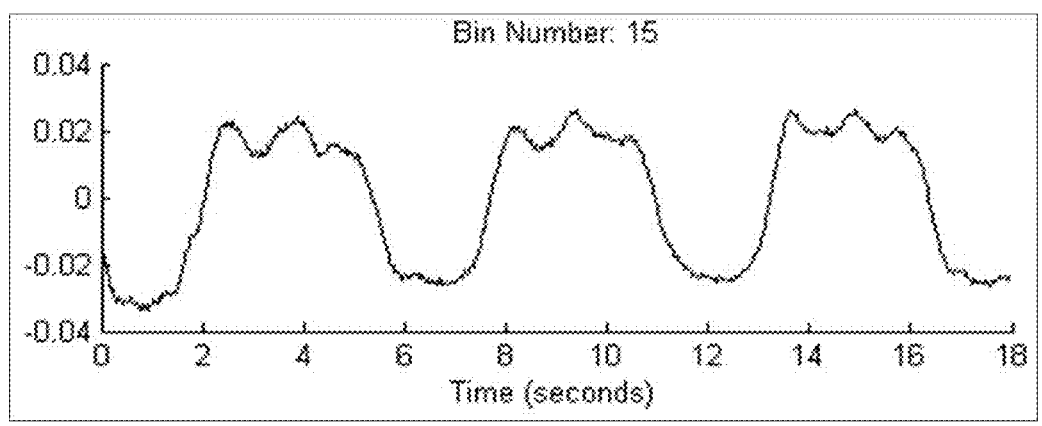
FIG. 35 is an illustration of an isolated respiratory trace generated by the software and algorithms according to an embodiment of the invention.

FIG. 35 is a chart produced from the software of the invention associated with FIG. 34 illustrating an isolated respiratory trace for a particular bin number 15. The respiratory trace follows the shape of a typical pulmonary cycle and also includes the influence of cardiac behavior throughout.

17. Dielectric Monitoring—Early Identification of Potential Congestive Heart Failure In a further embodiment, the present invention provides a novel system and method for monitoring those persons dealing with chronic heart conditions or other diseases which may cause them to suffer from periodic pulmonary congestion which can ultimately lead to congestive heart failure and death. Congestive heart failure is a serious physiological condition that is associated with changes in both cardiac performance and respiratory performance. FIG. 18 is an illustration of a subject experiencing partial congestion or fluid buildup in the subject's left lower lobe LLL. Congestion may be the result of cardiac failure or some other condition, such as pneumonia. In one embodiment, as illustrated in FIG. 18, congestion in lungs RL, LL may be monitored by one or more sensors 20. In a congestive heart failure monitoring mode, the apparatus 10 comprising one or more sensors 20, causes each sensor 20 to transmit a series of interrogatory pulses S at target areas T of the lungs RL, LL. Each of the sensors 20 of the apparatus 10 includes a transmit antenna 30 and receive antenna 40. The transmitting antenna 30 of each sensor 20 directs electromagnetic energy toward a target area T in the lungs RL, LL. A portion of the transmitted energy is reflected back from the target area T as reflected signals S' to the receiving antenna 40, in part, due to the large difference in dielectric value between the air and liquid in the lungs RL, LL, along with dielectric differences in other tissues in the target range of interest. In addition to the algorithms of the present invention tuned to capture and process anatomical motion, the apparatus 10 includes an advanced algorithm used in conjunction with one or more algorithms of the respiratory sensor module 50 for capturing dielectric information from various target areas T to track changes in dielectric values in the target areas T during a respiratory cycle.

FIGS. 36-39 are tables of simulated dielectric values associated with measurement of various respiratory states, measured in an aggregate manner or individually for each lobe of each lung. FIG. 36 is a table of simulated dielectric values for a subject in both a normal and congested state, emphasizing an aggregate basic correlation, preferably measured using a single sensor 20 targeted toward a lower portion of either the right lung RL or left lung LL. The lower portion of either lung RL, LL would be targeted since congestion is frequently found to first occur in the lowest lobes of each lung RL, LL. In the congested state, the dielectric value is higher due to the presence of additional fluids in the lung tissue. Consequently, in a first version, the present invention would comprise two sensors directed to the left lower lobe LLL and the right lower lobe RLL of the subject since these lobes are most likely to first experience fluid build-up, indicating a trend toward congestive heart failure.

FIG. 37 is a more detailed table of simulated dielectric values for an individual progressing from a normal respiratory state (without congestion) through to a third state of congestion, as measured at an inflated and deflated point in the normal respiratory cycle. For clarity of explanation, the simulated data tabulated in FIGS. 36-39 are shown as being presented only at a fully inflated or fully deflated state. However, in a preferred embodiment, the sensor 20 of the apparatus 10 continuously measures the dielectric values associated with the targeted areas during the entire respiratory cycle. The data tabulated in FIG. 37 is once again based on an aggregate dielectric value measured from a targeted portion of either lung RL, LL, preferably the lower portion of either lung RL, LL. The table of FIG. 37 tracks the cumulative average and the cumulative dielectric values measured by a single sensor 20 over four states from normal to full congestion.

FIG. 38 is a table of simulated dielectric values of an individual progressing from a normal uncongested respiratory state to a third state of congestion, wherein the dielectric value is measured by separate sensors 20 arranged to target each individual lobe of each lung RL, LL. For purposes herein, the left superior lobe is the equivalent of the left upper lobe LUL; the left inferior lobe is equivalent to the left lower lobe LLL; the right superior lobe is equivalent to the right upper lobe RUL; and, the right inferior lobe is equivalent to the right lower lobe RLL. By increasing the granularity of the measurements to target each lobe, the apparatus 10 comprising at least five sensors 20 directed toward each lobe can track dielectric behavior of each lobe to increase the amount of information available to a physician, thereby increasing the physician's respiratory knowledge specific to a particular patient and allowing the physician to evaluate the information to identify earlier precursors of congestive heart failure. For example, after evaluating a patient using five or more sensors 20 targeted toward each lobe, the physician may be able to determine that a single sensor 20 positioned above a particular lobe will provide sufficient information to respond to earlier indicators of a trend toward congestive heart failure to avoid allowing the patient to reach a state of full congestive heart failure.

FIG. 39 is a table of simulated dielectric values for a hypothetical subject progressing from normal respiration to full congestion measured at each individual lobe, but only at a fully inflated or inspired state.

Each of FIGS. 36-39 provides data which forms the basis for subsequent FIGS. 40-43, described in greater detail below. Now, in greater detail, the apparatus 10 of the present invention obtains a measure of the change in the bulk dielectric strength of a targeted portion of the lungs RL, LL during a respiration cycle over a period of time to develop a trend which may indicate progression toward congestive heart failure or implications from other diseases known to cause fluid build-up in the lungs, e.g., pneumonia.

Figure 40:
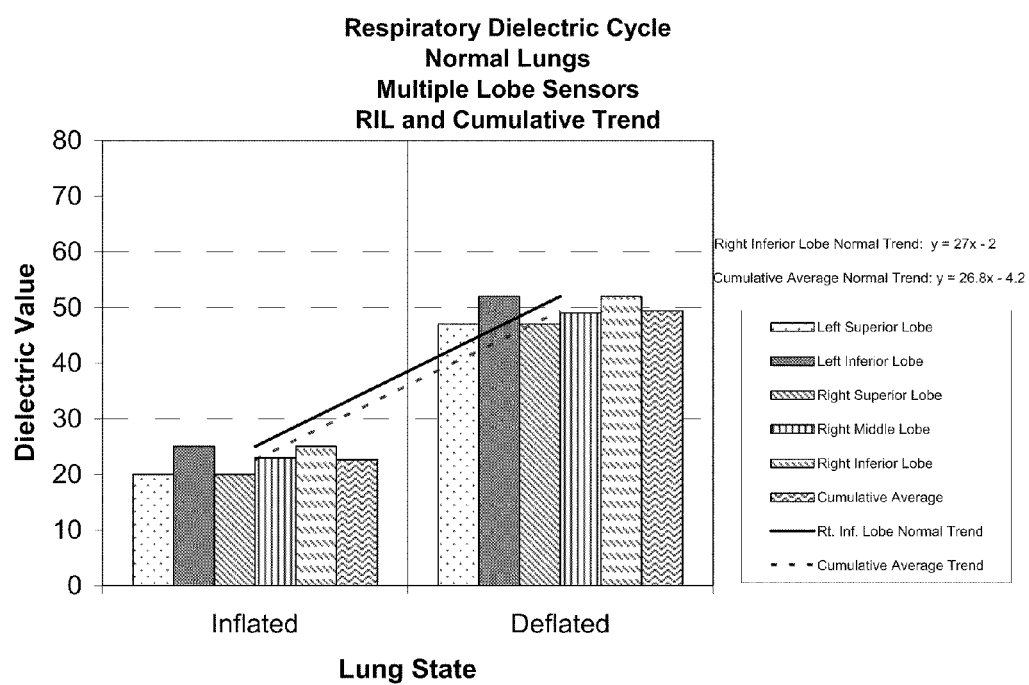
FIG. 40 is a combined bar and line chart illustrating the dielectric relationship of a normal respiratory cycle using multi-lobe sensors according to an embodiment of the invention.

FIG. 40 is a chart illustrating normal or baseline dielectric measurements associated with each lobe at full inflation and deflation during a normal respiratory cycle where the subject is known to not have congestion. This baseline relationship is ingested by the apparatus of the present invention to serve as an anchor in determining when deviations from this baseline are suggestive of cardiac or respiratory complications. Importantly, by measuring the dielectric behavior of the lungs during a respiratory cycle, the apparatus may be capable of identifying indicators of a trend toward congestive heart failure that in the past have been unavailable. In the normal baseline, the dielectric value measured at each lobe of each lung is greater during the deflated state due to a reduction in the amount of air in the lungs.

FIG. 40 further includes two trend lines describing the mathematical relationship between the measured dielectric value and a lung status at either a fully inflated or fully deflated state. The first describes the relationship for the right inferior lobe RML; the second describes the relationship based upon a cumulative average trend across all lobes. A fundament element of the method of the present invention for determining whether a subject may be progressing toward congestion is continually monitoring the subject and providing an alert whenever the readings deviate from the algorithmic relationship associated with respiration during an uncongested status. The apparatus 10 will continually track the measured dielectric values and compare these values against multiple trend lines associated with non-congestive pulmonary performance. Although shown in FIG. 40 as providing only two trend lines, the present invention supports the development of a multiplicity of trend lines where a trend line may be developed for each lobe of each lung at differing levels of inflation/deflation.

Figure 41:
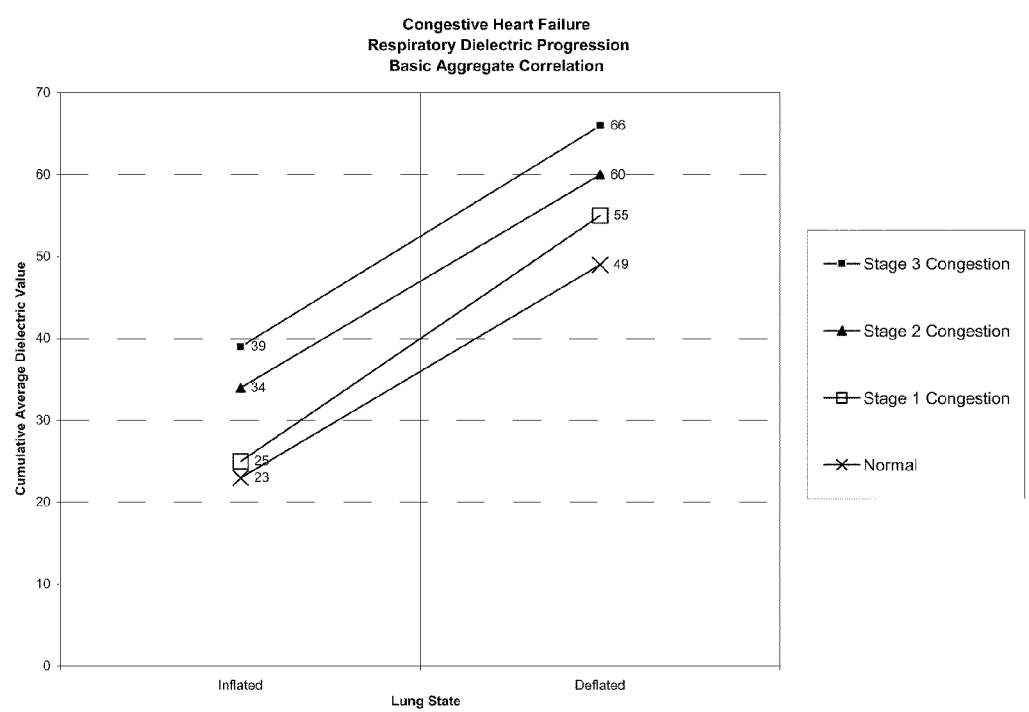
FIG. 41 is a line chart of basic aggregate correlation of respiratory dielectric progression toward congestion and heart failure of a subject according to an embodiment of the invention.

FIG. 41 is a chart tracking the change in measured respiratory dielectric values during a respiratory cycle through three progressive stages toward congestive heart failure. Again these measurements are simulated for acquisition at the fully inflated and fully deflated state of a normal respiratory cycle, and therefore, presume a straight line relationship between the two extremes of inflation and deflation. However, the apparatus 10 of the present invention will provide a continuous measure of dielectric value to provide a more comprehensive view of changes and trends in dielectric values during multiple stages of progression toward congestion. For example, the shape of the curve between fully inflated and fully deflated during an entire respiratory cycle would have value to measure any breathing restrictions based upon the shape of the curve. Additionally, the present invention is equally adept at determining the efficacy of treatment to avoid congestion by monitoring the dielectric values and determining that trends are heading back toward the normal baseline dielectric values.

Water is known to occupy approximately 60% of the tissue volume in a normal lung. As the lungs inflate during inspiration, additional air enters the lungs, causing the bulk dielectric constant of the target area of the lung to decrease, reaching a minimum at full inflation since the dielectric strength of typical lung tissue is greater than that of air. As the lungs deflate during expiration, air is expelled from the lungs, and the bulk dielectric constant of the target portion of the lung increases, reaching a maximum at full deflation. For illustrative purposes, and with reference to FIGS. 36 and 40, this relationship can be described where, in a fully-inflated state, the targeted lung tissue has a dielectric strength of 20 as measured by the apparatus; in a fully deflated state, the targeted lung tissue has a dielectric strength of 47. Consequently, during a respiration cycle, the dielectric strength will vary approximately between the two values of 20 and 47.

The variance from the minimum or maximum dielectric value at a point in time may be calibrated to establish the approximate volume of air in the lungs at any point and time during a respiration cycle. Hence, the present invention uses the relationship between changes in dielectric value as measured by the apparatus 10 and the existing volumetric model of the lungs to determine the volume of air in the lungs at any time during a respiration cycle.

As indicated, the apparatus 10 of the present invention continuously measures the value and difference in the lung dielectric strength between peak inflation and deflation, and then establishes a measure of the tidal volume during a respiration cycle by correlating the dielectric difference to empirical measurements of volumetric change. Once the dielectric differences have been correlated with volumetric differences, the algorithm of the method of the invention creates a correlated dielectric-volumetric curve (DVC). Referring to FIG. 40, the DVC is then used in the process to determine instantaneous lung volume at any time during a respiration cycle. This difference measurement may be further correlated with the mechanical motion associated with lung excursions associated with a respiratory chamber 70 as measured by one or more sensors 20, thereby providing a second measure and check to increase overall accuracy of measurements. The invention then uses these measurements to also provide another cross-check to tidal volume and to instantaneous respiratory volume (IRV) determined using the previous described imaging methods associated with image quantizer module 300 and the motion detection and selection module 400.

As illustrated in FIG. 40, in a further derivative embodiment based on measurement of changes in dielectric strength during a respiratory cycle to assist in the early identification of congestive heart failure, the algorithm of the method of the invention includes an adaptive function to measure and track the value of the bulk or cumulative dielectric strength of a target respiratory chamber over time, creating a normal respiratory dielectric curve for the respiratory cycle of a subject. The method of this embodiment presupposes that a base-line or normal respiratory dielectric curve is generated during periods of relative health where congestion is not present. Once this normal respiratory dielectric curve has been established, the apparatus 10 then continues to track and monitor the dielectric strength of the targeted respiratory chamber 70 of the subject to monitor any deviation from normal status. When the apparatus 10 determines that a deviation from normal has occurred, the deviation is then assessed to determine potential causes for the deviation. Alternatively, whenever a deviation from normal is observed by the apparatus 10, an alert may be triggered requiring various subsequent follow-up actions or responses.

For example, in one circumstance, the algorithm of the method of the present invention determines whether the change in the respiratory dielectric curve is due to the buildup of fluid within the targeted portion of the lung. Abnormal fluid buildup in the lungs will cause the apparatus 10 to detect an overall increase of the measured dielectric strength of the targeted portion of the lung, during both inspiration and expiration, shifting the entire curve upward, away from the normal base-line position, as shown in FIG. 41. Once the apparatus 10 determines that the measured data suggest the deviation from the normal respiration dielectric curve is possibly due to fluid buildup in the lungs, the other measured physiological parameters are examined and evaluated to determine if corresponding changes have occurred that suggest a trend toward, or, the onset of, congestive heart failure. The change in fluid content parameter is juxtaposed against trends and changes in cardiac rate and rhythm, stroke volume, respiratory rate and rhythm, and tidal volume, among others, to help determine whether the symptoms suggest the onset of congestive heart failure, thereby providing a real-time early warning system to allow treatment at the earliest stage possible.

Figure 42:
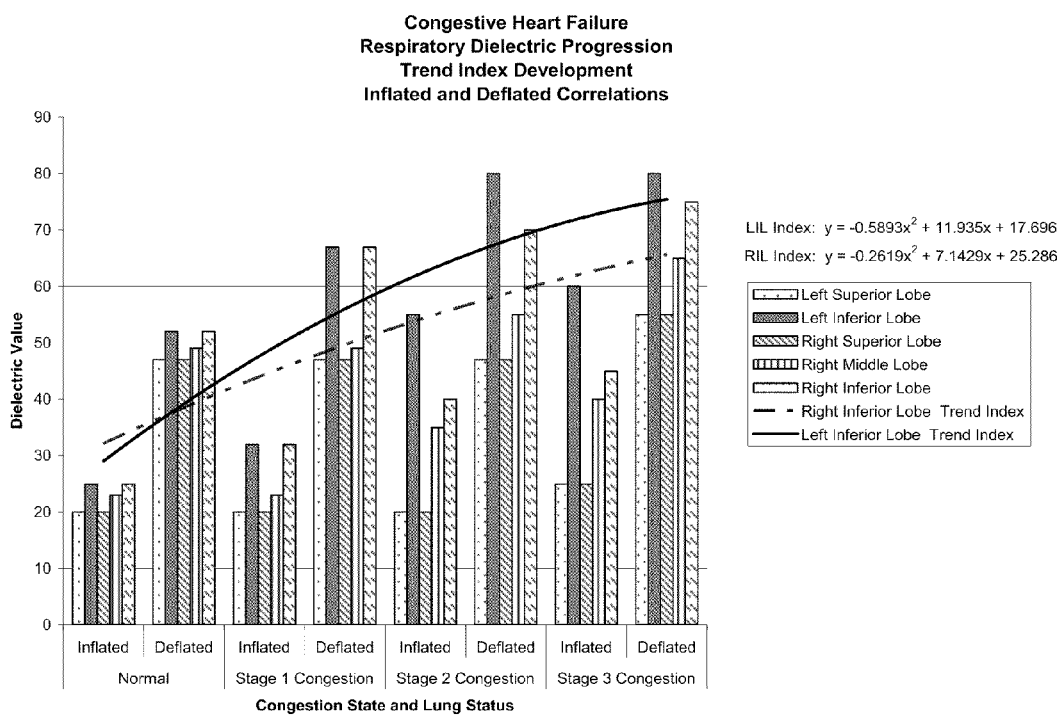
FIG. 42 is a combined bar and line chart illustrating multi-lobe sensor respiratory dielectric progression toward congestion and associated dielectric trends, according to an embodiment of the invention.

FIG. 42 is a chart illustrating respiratory dielectric progression during stages of congestion for each lobe of each lung along with the development of trend indices for both the right and left inferior lobes RLL, LLL, as measured and calculated by the present invention. The right and left inferior lobes RLL, LLL were chosen for assessment and trend development in this case since the lower lobes tend to present with congestion earlier than the middle or upper lobes. The data for the chart is based upon simulation of data collection from five sensors 20 placed on an individual's chest and thorax in both an inflated and deflated state through four stages progressively moving toward congestion. In this simulation, the dielectric progression for the left inferior lobe LLL is described by the LIL Index described by the polynomial equation:

$$y = -0.5893x^2 + 11.935x + 17.696$$

where y is the dielectric value; x is the stage of congestion.

Consequently, the present invention would track the dielectric value for the right inferior lobe RLL and continue to compare the measured dielectric value against the trend index. Based upon the measured dielectric value, the apparatus would determine what stage of congestion is being experienced by the patient. Depending on the stage of congestion, various responses would be triggered by the apparatus. For example, a first stage of congestion might trigger an alert to take a diuretic of some sort to reduce fluid.

A second stage alert might trigger an alert to advise the patient to contact their physician for additional guidance. A third stage alert might trigger an alarm sent to the patient and others to direct the patient to reach an emergency room as soon as possible. Other triggers and associated alerts can be incorporated in the algorithms to allow additional desired actions and responses driven by the measured dielectric values and assessment of overall congestion as determined by the dielectric progression curve, i.e., the dielectric progression trend index for a particular lobe.

Figure 43:
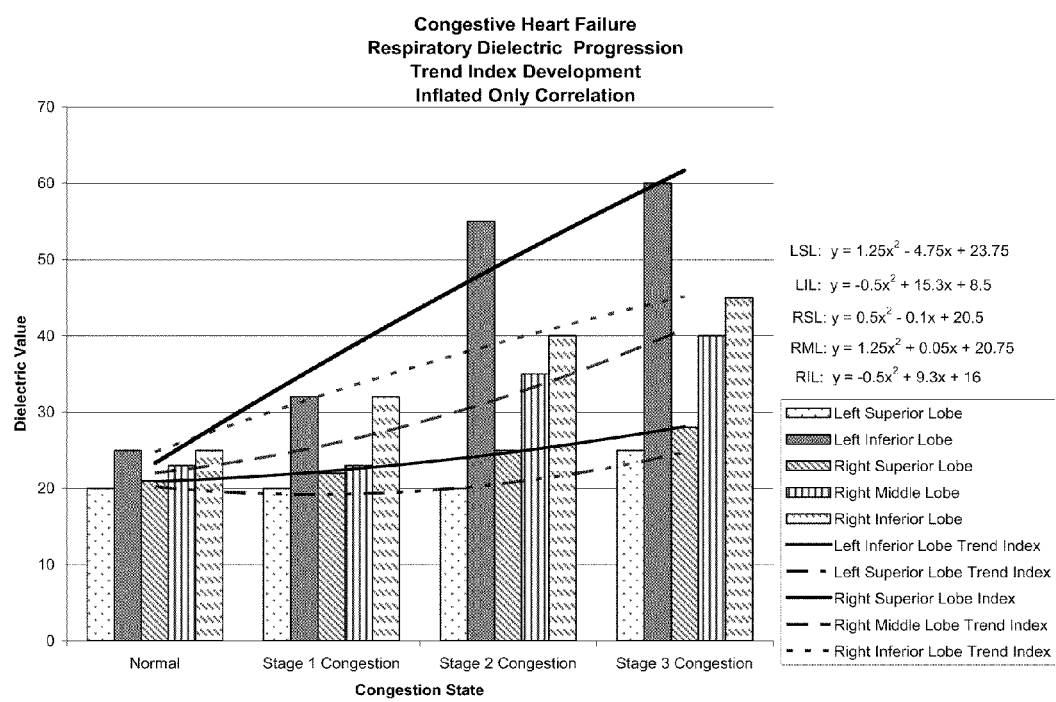
FIG. 43 is a combined bar and line chart illustrating multi-lobe sensor respiratory dielectric progression toward congestion and associated dielectric trends as measured at lung inflation, according to an embodiment of the invention.

FIG. 43 is a chart illustrating the ability of the present invention to track and trend the dielectric behavior of each lobe of each lung simultaneously. As illustrated, the present invention generates a trend index for each lobe such that the progression of congestion in each lobe may be monitored and used as part of the clinical evaluation of a patient. For example, the present invention supports the incorporation of alarms where the congestion might present in any of the five lobes. Each of the dielectric progression curves may be consulted and readings from each sensor 20 for each lobe may be compared against their respective dielectric progression curves. For example, in the case where a subject may be experience some level of congestion in a left lower lobe LLL but not in the right lower lobe RLL, a physician may elect to delay treatment since there is only evidence of congestion in the left lower lobe. Consequently, if only one sensor 20 were used on the left lower lobe LLL, and the readings indicated a progression toward congestion, more drastic action might be taken to seek help to address the congestion.

In a further version, the present invention supports the juxtaposition and comparison of measured change in dielectric value against data from other sensors, such as a pulse oximeter. For example, upon determining that the measured dielectric values suggest a trend toward, or onset of, congestive heart failure, the measured oxygen saturation provided by the pulse oximeter may be assessed. If pulse oximeter indicates that oxygen saturation is low or dropping, this would further reinforce the indications provided by the apparatus 10 via measurement of dielectric value.

The ability of the apparatus and method of the present invention to provide early identification of potential progression toward congestive heart failure will substantially improve a caregiver's ability to monitor an at-risk individual. This capability will dramatically reduce the mortality rate normally anticipated with the onset of congestive heart failure. The symptoms will not be overlooked simply because the subject is not adequately and constantly monitored. Those individuals predisposed to congestive heart failure do not always have access to a hospital or clinical facility where more complex and sophisticated systems can be used to determine the onset of congestive heart failure.

This capability would also be invaluable in helping to diagnosis potential heart problems where the condition develops over a longer period of time, and hence, would not be as noticeable. For example, for the ambulatory individual in a home setting, the typical methods used to determine whether an individual might have symptoms indicative of congestive heart failure are extremely rudimentary, qualitative and imprecise, and therefore, likely to place a subject prone to congestive heart failure at greater risk for not detecting onset of congestive failure. For example, current methods recommended by physicians require that an individual weigh him or herself on a periodic and regular basis, to determine if there is an abnormal amount of weight gain, suggesting fluid buildup. One approach is to weigh each morning and night. Unfortunately, this period is sufficiently long that an individual could suffer from congestive heart failure during the period between weigh-ins. Additionally, if an individual had a fairly large meal, the additional weight gained might be perceived as simply a result of the excessive indulgence, when in reality, a portion could actually be caused by pulmonary congestion.

Another existing method used to assess the potential onset of respiratory and cardiac congestion is to measure the number of pillows used during sleep. While sleeping, an individual will monitor the number of pillows required to create a sufficiently comfortable position to avoid breathing complications. If additional pillows are required, this may indicate fluid buildup in the subject's lungs and potential onset of congestive heart failure. As can be appreciated, this method is very qualitative, subjective and depends on the patient to determine whether problems are developing.

Additionally, another existing monitoring method is for the patient to monitor the size of his or her lower extremities by measuring or observing the circumference or skin tension of the legs and ankles to determine if there is any potential swelling, which might also suggest fluid buildup and indicate potential onset of congestive heart failure. Again, this approach is qualitative in nature and relies on the assessment of the patient.

As described above, when sophisticated monitoring is unavailable in an at-home setting, the patient is expected to monitor weight fluctuations, the number of pillows required to sleep comfortably, and, swelling in the legs. Unfortunately, these are gross qualitative measures that first presume the at-risk individual is actually capable of accurately monitoring these parameters. If the particular individual has other medical complications, such as Alzheimer's, short term memory loss or other dementia common in elderly patients or patients experiencing oxygen deprivation due to congestion, it is unlikely they will have the ability to accurately monitor these parameters without caregiver assistance and follow-up. They will be unable to stay abreast of their medical condition and determine when additional treatment is indicated to mitigate the affects of fluid buildup, without the assistance of a caregiver. Consequently, the present invention provides a more definitive, simple, reliable and accessible means to monitor for potential heart failure while avoiding the failings of the other existing qualitative methods described above. The present invention provides a simple medical device that can independently monitor precise, quantitative parameters indicative of congestive heart failure, and, relay those measures to a more qualified individual capable of triggering a treatment response when indicated, or, at a minimum, relay those measures to the patient so that the patient can confidently and quickly seek additional assistance and care from their physician or emergency room, if necessary. This increased confidence in measurement will allow a physician to more readily diagnose and treat the patient. This increased confidence in measurement will also reduce the stress a patient experiences when unable to determine whether he or she is actually experiencing pulmonary and cardiac problems. Hence, the present invention will reduce the number of unnecessary visits to a patient's physician which are caused by the patient's concern that perhaps they are trending toward congestive heart failure. Likewise, the present invention will expedite treatment when necessary since the responding physician will have greater confidence in the quantitative measures provided by the various embodiments of the present invention as compared to the qualitative assessments provide by the patient.

18. Respiratory Chamber Excursion Measurement

Now, in greater detail, the process for measuring respiratory chamber excursion and associated tidal volume is described. The apparatus and method of the present invention comprises a novel medical imaging arrangement where analog assessment approaches are combined with UWB radar in estimating volumetric changes associated with a targeted respiratory chamber 70 and therefore, assessing overall respiratory performance via the development and calculation of various respiratory metrics and parameters. According to a preferred embodiment of the present invention, as illustrated in FIG. 4, FIG. 16A and FIG. 16B, the apparatus 10 collects reflection data S' from one or more target areas T, associated with a selected respiratory chamber 70 encompassed by an interrogation volume 60.

19. Identification of Respiratory Disturbances or Events

The present invention provides respiratory information that is used to detect a significant respiratory disturbance and to detect suspicious deviation from normal respiratory trends over time. Following is a description of an embodiment of the method of the present invention used to identify respiratory events.

FIG. 4 provides an illustration of the basic operation of the apparatus and method of the present invention. First, a physiological signal that varies with a patient's respiration cycle is monitored using the apparatus 10 comprising a sensor 20 having a transmitter 30 and receiver 40. Monitoring by the sensor 20 may be either continuous or on a periodic or triggered basis. As will be described, the apparatus 10 processes, stores and/or transmits sensed signal data. A physiological signal received is at least a measurement of respiratory-induced motion within the thoracic or abdominal cavity from which respiration rate and rhythm or other pulmonary metrics may be determined for calculating, among other things, tidal volume, total lung capacity, and volumetric output. The physiological signal is either a direct measurement of lung motion or other associated anatomical features that include variations due to the respiratory cycle. The physiological signal may also be a measure of dielectric strength within a targeted portion of a lung. The physiological signal may be either a measure of change or an absolute value. The physiological signal may be obtained along with other physiological signals such as cardiac rate, cardiac rhythm, cardiac stroke volume, blood oxygen saturation, blood pressure and thoracic or cardiac electrical activity.

The method of the present invention is implemented in the external sensor device 20 or in an external device capable of receiving sensed signal data from the external sensor device 20 via a telemetric communication link. First, parameters indicative of the patient's respiratory activity are derived from the sensed signal. Preferably, at least a respiration rate is determined. Additionally, other respiration parameters, such as tidal volume or peak amplitudes associated with the respiration cycle, may be determined.

At a next decision step, the measured respiration parameters are compared to predetermined criteria for detecting a respiratory disturbance or deviation from a respiratory trend. Such criteria may include at least a respiration rate, a tidal volume, or a dielectric value such that when the respiration rate, tidal volume, or dielectric value is less than or greater than a normal range or crosses a detection threshold, a potential respiratory disturbance is detected at a decision step and labeled as a suspicious event. At a storage step, measurements of the suspicious respiratory disturbance are determined and stored. Such measurements preferably include at least the duration of the disturbance. At an alert step, detection of the respiratory disturbance may optionally trigger a warning to medical personnel, the delivery of a therapy, and/or the storage of physiological data in the apparatus.

In one embodiment of the present invention for monitoring respiratory disturbances based on ultra-wideband (UWB) sensing, a reflected UWB signal S' is received, and the tidal volume and respiration rate and rhythm are derived from the UWB signal, which may be used for calculating respiratory output.

At a next decision step, one or more predetermined criteria for detecting a respiratory disturbance are applied to the measured tidal volume and/or respiration rate and rhythm. Predetermined criteria may include comparing a given respiration parameter to a minimum or maximum threshold. If criteria for determining a respiratory disturbance are not satisfied, the method returns to continue monitoring the UWB signal. If detection criteria are met, a respiratory disturbance is detected. Measurements of the disturbance may then be made, preferably including at least the duration of the disturbance. The duration of the disturbance may be an apnea/hypopnea length or hyperpnea length determined as the number of device clock or timer cycles during which corresponding detection criteria are satisfied. The duration is then stored, along with other relevant data including a time and date label to indicate when the detection was made. At a next step, a counter for tracking the number of detected respiratory disturbance episodes is increased by one. An optional warning or alert to medical personnel by an external device or triggering of a therapy delivery or data storage by another external device may then be generated. A triggered therapy may be, among other things, cardiac pacing, delivery of a pharmacological agent, insulin delivery, stimulation of the upper airway muscles, the diaphragm, or other electrical stimulation of the central nervous system, peripheral nerves or smooth or skeletal muscle. The method is continually repeated to continue monitoring for respiratory disturbances.

Additional details regarding methods for determining metrics of respiratory disturbances in one embodiment of the present invention are provided. Upon detecting a respiratory disturbance, it may be desirable to determine various metrics of the disturbance in order to assess the severity of the disturbance and/or track changes in these metrics over time as a way of assessing relative improvement or worsening of the associated pathological condition. First, an UWB signal input is received and used for determining tidal volume, respiration rate, absence of respiratory movement or dielectric value. Next, the derived tidal volume, respiration rate/rhythm, absence of respiratory movement or dielectric value is compared to a predetermined apnea detection threshold, hyperpnea detection threshold, or dielectric threshold. If a threshold crossing is detected, a respiratory disturbance is detected, and the time of the onset of the disturbance is flagged.

The method continues to iterate and receives a next UWB signal. The method continues to monitor the respiration parameters until the detection criterion is no longer satisfied. If a respiratory disturbance onset has been flagged, as determined at a preceding decision step, the respiratory disturbance offset is flagged. If the detection criterion is not satisfied, and no onset is flagged, then method continues to iterate and receives a next UWB signal to continue monitoring respiration parameters. After flagging the onset and offset of a respiratory disturbance, such as an apnea or hyperpnea period, or, a congestion period as determined by a dielectric value, the length of the apnea, hyperpnea or dielectric congestion period is stored as the difference between the flagged onsets and offset.

Next, the method determines if a previous apnea episode has been recently detected, which could indicate the presence of a repetitive breathing pattern. Repetitive apnea-hyperpnea or hypopnea-hyperpnea alternation is typical of certain pathological breathing patterns such as sleep apnea and Cheyne-Stokes breathing. If this decision step is affirmative, a periodic breathing cycle length is determined and stored as the time between onsets of two consecutively detected apnea episodes. A respiratory disturbance episode counter is then increased by one for each disturbance detected. Depending on the type of pathological breathing pattern being monitored, a disturbance that would increase the episode counter may be a single apnea, hypopnea, or hyperpnea event or may be a complete apnea-hyperpnea or hypopnea-hyperpnea cycle. Next, a warning to alert medical personal, to wake up the subject individual and/or to trigger a therapy delivery and/or data storage trigger may be generated.

In a further alternative embodiment, a method for monitoring for respiratory disturbances or trend deviation is provided. Alternative embodiments may detect pathologic breathing patterns by determining a patient's respiration rate from any physiological signal measurable with the apparatus that includes variations due to the influence of inspiration and expiration, such as a cardiac signal. First, a physiological signal input is received. A physiological signal that includes respiration related variations may be, but is not limited to, a cardiac signal. Next, the patient's respiration rate is derived from the cardiac signal. The sensed signal may be filtered to remove higher frequency components and pass low frequencies associated with the respiration cycle to establish a respiration rate. A preferred method for deriving the respiration rate comprises a simple peak detection algorithm. In this case, an input UWB signal measures excursion in the abdominal or thoracic region of any feature which has variability caused by the respiration cycle. By detecting individual breaths and related peaks and valleys of the UWB signals, respiration rate can be derived by measuring the interval between peaks and tidal volume may be derived by measuring peak to peak amplitude change from a peak to the corresponding valley.

The derived respiration rate is compared to predetermined criteria for detecting a pathologic respiration rate. For example, predetermined respiration rate criteria may define a rate limit or zone that is indicative of Kussmaul breathing, which is more closely related to tidal volume, Cheyne-Stokes breathing, apnea, asthma, or other respiratory disturbances. The onset and offset of a detected respiratory disturbance are flagged, allowing the duration of the disturbance and the cycle length of a periodic breathing cycle to be determined and stored. A respiratory disturbance episode counter is increased, and a responsive action or no action is taken.

20. Parameter Cross Check and Confirmation

A further alternative embodiment of a method for monitoring for respiratory disturbances includes a parameter cross-check. The parameter cross-check assists in confirming a suspected respiratory disturbance prior to detecting the disturbance. A parameter cross-check may employ the signal from an additional UWB sensor or sensors for verifying that modulation of the primary physiological signal used to detect the respiratory disturbance is indeed due to respiration and not other motion or factors. In one embodiment, a UWB sensor tracks body motion to verify that the signal variations extracted from the primary signal are not due to changes in body motion. Alternatively, a separate sensor, such as an oxygen saturation sensor, may be monitored and compared to the UWB signal outputs to confirm trends that point to a respiratory disturbance. For example, in the case where a subject's breathing ceases or is spotty, the subject's oxygen saturation will decrease according to the breathing pattern.

In another embodiment, one or more physiological signals are continuously monitored for detecting a respiratory disturbance according to the methods described above. Physiological signals indicative of heart function may additionally be monitored and juxtaposed against physiological signals indicative of respiratory function. If a respiratory disturbance is detected and determined to be a periodic breathing pattern, metrics of the periodic breathing pattern are determined. If not, the method returns to continuous signal monitoring. These periodic breathing metrics can be correlated to cardiac function and be used as cross-checks against metrics developed using UWB cardiac signals. Trends of these periodic breathing metrics are determined and stored for display in various formats. A change in cardiac output may be estimated based on respiratory disturbance metrics. These data may be displayed for review by a physician such that worsening or improvement in respiratory or cardiac condition can be observed. Thus, detection and evaluation of disordered breathing patterns may be used for assessing a patient's cardiac condition and vice versa. If the method is implemented in association with an implantable device capable of delivering a heart failure therapy, a worsening or improvement in cardiac output may optionally automatically trigger an appropriate delivery, withholding, or adjustment of therapy to the patient.

21. Implantable Sensor

As indicated above, the present invention preferably employs an external sensor 20 for chronic respiration monitoring. The methods described above for detecting a respiratory disturbance may be fully incorporated in an external device in association and communication with one or more external sensors 20. Alternatively, an algorithm for detecting a respiratory disturbance and measuring characteristics of a respiratory disturbance may be implemented in an implantable sensor in telemetric communication with the external device associated with the implantable sensor, in which case the external device serves primarily, for the purposes of the present invention, for storing chronic sensor signal data and/or transmitting the data to an additional external data storage and processing or communication device, such as a network server. External sensor (s) deliver received signals via appropriate lead (s), conductor (s) or wireless links to signal conditioning circuitry of an external device. Implantable sensor (s) may be located externally to the device but within the body of the patient or internally to the device. In addition to the UWB sensors, others sensors, including electrodes, may be integrated with the apparatus to provide sensing for an ECG, EMG, or diaphragmatic EMG signal, electrodes for sensing thoracic impedance, a blood pressure sensor, an activity sensor, an oxygen sensor, or any other sensor that is expected to provide a variable signal containing information related to a patient's respiration pattern to provide confirmatory information. Multiple sensors containing respiratory information may be included. Further, where an implantable device is used, additional physiological sensors may be present such as temperature sensors, pH sensors, or any other sensors of signals of interest.

The signal conditioning circuit provides filtering, amplifying, rectifying and other conditioning for sensor signal input as necessary to eliminate noise and signal components unrelated to respiration. Additional signal conditioning circuitry may be included in the apparatus if sensed signals are used for other functions other than detection of respiratory disturbances. For example, an ECG signal may be filtered by signal conditioning circuit for extracting a respiration rate, and the ECG signal may be used by other circuitry for detecting heart rhythm. In another example, a blood pressure signal may be filtered by the signal conditioning circuit for deriving a respiration rate, and the blood pressure signal may be used by other circuitry included for monitoring a patient's cardiac function.

When respiration disturbance detection methods described herein are incorporated in the internal device, the output from the signal conditioning circuit is provided as input to an analog-to-digital (A/D) converter which then provides input to a respiratory disturbance detector. Output from the A/D converter may also be provided directly to data storage memory for storing digitized signal data that may be uplinked to an external device through a telemetry link. Communication systems for use with implantable devices are known in the art. The detector may perform additional signal processing to derive signal features of interest, such as respiration rate, and perform the methods described above for detecting a pathological respiration pattern. The detector is preferably implemented as programmable software stored in the memory of a microprocessor. Alternatively, the detector may be in the form of dedicated digital circuitry. The microprocessor includes memory for storing executable programs for controlling and executing various apparatus functions.

If a respiratory disturbance is detected by the detector, according to the methods included in the present invention, other apparatus functions may be triggered such as the storage of physiological data in memory and/or the delivery of a therapy from a therapy output controller. Stored data may include measurements of the respiratory disturbance, time and date information relating to when the disturbance was detected, the number of disturbances detected, updated trends of respiratory disturbance metrics, as well as other data based on other sensor input, such as ECG or EGM, blood pressure, oxygen saturation, activity, and so on.

Thus, the apparatus may be provided as an implantable recording device capable of monitoring physiological signals and storing physiological data upon a triggering event.

Physiological data and respiratory disturbance metrics stored in data storage memory may be uplinked to an external device through a telemetry link. Stored data may then be displayed on a display for review by a physician. The internal apparatus and sensor may be a minimally invasive, subcutaneous system. Internal apparatus and sensor (s) may alternatively be a relatively more invasive system with sensor (s) implanted submuscularly, intramuscularly, along or within the vascular system, within the thoracic cavity, heart, airways or other internal body locations appropriate for receiving a signal variable with the patient's respiration cycle. A system including a chronically implanted blood pressure sensor and processing element is generally disclosed in U.S. Pat. No. 5,758,652 issued to Nikolic, incorporated herein by reference in its entirety.

22. Therapy Delivery Control and Feedback

Where the apparatus includes therapy delivery capabilities, a therapy output control delivers a therapy in response to the detection of a respiratory disturbance. Such therapies may include cardiac pacing, neuromuscular stimulation, stimulation of the central nervous system, delivery of a pharmacological or biological agent, or other therapy. Thus, the apparatus may be embodied as a cardiac pacemaker, implantable cardioverter defibrillator (ICD), neuromuscular stimulator or other type of electrical pulse generator, implantable drug delivery device or other type of therapeutic, implantable device. Examples of implantable devices that include therapy delivery capabilities in which aspects of the present invention could be implemented include: a cardiac pacing device for managing sleep apnea generally disclosed in U.S. Pat. No. 6,126,611 issued to Bourgeois et al., a medication infusion system generally disclosed in U.S. Pat. No. 4,373,527 issued to Fischell, an implantable drug delivery system generally disclosed in U.S. Pat. No. 6,471,689 issued to Joseph et al., and a device for stimulating upper airway muscles for treating obstructive sleep apnea generally disclosed in U.S. Pat. No. 5,540,733 issued to Testerman et al., all of which patents are incorporated herein by reference in their entirety.

Thus, aspects of the present invention may be readily implemented in implantable devices already having an appropriate signal sensed for other device functions and which may also be used for determining respiration parameters. Patients having such devices may receive greater benefit by the added detection of respiratory disturbances when they occur.

Signal data stored in memory directly from the A/D converter may be uplinked to an external device. As an alternative to performing respiratory disturbance detection online or in real time within the internal apparatus, stored signal data may be post-processed by the external device. The external device is preferably a microprocessor-based device, which may be better able to accommodate computationally-intensive algorithms than an implantable device for extracting respiration data from a sensed signal and for processing such data for the detection of pathologic patterns and for measuring characteristics of such patterns. The external device may be embodied as a logic device and programmer known for use with implantable, programmable devices for programming operational parameters into the internal apparatus and for receiving stored data or other operational information from the implanted apparatus. The external device may alternatively be in the form of a personal computer with an added telemetry interface for communicating with the internal apparatus. When embodied as a programmer, the external device may receive stored signal data and save it in a format that may be transferred to a personal computer for further processing or by internet to a central patient management network. A bi-directional communication system that is network, Internet, intranet and worldwide web compatible to enable chronic monitoring based on data obtained from implantable monitors is generally disclosed in International Publication No. WO 01/70103 A2, issued to Webb et al, incorporated herein by reference in its entirety.

A respiration disturbance detector may be included as an executable program in the microprocessor of the external device. The detector detects respiratory disturbances offline, using methods described herein, from stored signal data uplinked from the internal apparatus. If a pathologic breathing pattern is detected, a clinician alert may be generated, which may be an audible and/or visual notification displayed on a display with supporting data. The alert may also be in the form of a phone call or page to one or more remote or local locations, including cell phones, PDA's or pagers. Metrics of the detected disturbances are preferably displayed on the display.

An oximeter for measuring blood oxygen saturation may be provided as an implantable sensor or as an external sensor and used to cross-check readings from the sensors 20 of the apparatus 10. Therefore an oximeter may be included in implanted sensors and provide oxygen saturation data directly to the internal implanted apparatus 10. An oxygen saturation signal may then be used as a cross-check parameter in response to detecting a respiratory disturbance. The oxygen saturation signal may additionally be the primary signal used by the respiratory disturbance detector for measuring the patient's respiration rate for detecting respiratory disturbances. Alternatively, an external oximeter may be provided for measuring blood oxygen saturation. An external oximeter may be placed at various body locations but is preferably placed on a fingertip or ear lobe. The oxygen saturation signal may be received by the external device and may under go filtering, amplification or other signal conditioning and digitization. The oxygen saturation signal can be down-linked to the internal apparatus via a telemetry link such that when the internal apparatus detects a respiratory disturbance, the internal microprocessor can confirm the respiratory disturbance via cross-check with the oxygen saturation parameter.

Thus, an apparatus and method have been described for monitoring respiration and detecting respiratory disturbances that are related to a pathological condition. While specific embodiments have been described herein, it is recognized that variations of the described methods for detecting respiratory disturbances, measuring characteristics of the disturbances, and storing and displaying respiratory disturbance data will exist. The embodiments described herein, therefore, are intended to be exemplary, not limiting, with regard to the following claims.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

The present invention has been particularly shown and described with respect to certain preferred embodiments and features thereof. However, it should be readily apparent to those of ordinary skill in the art that various changes and modifications in form and detail may be made without departing from the spirit and scope of the inventions as set forth in the appended claims. The inventions illustratively disclosed herein may be practiced without any element which is not specifically disclosed herein.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. An apparatus for determining a change in the dielectric or spatial configurations of multiple portions of a lung or lungs of a patient by interrogating the portions of the lung or lungs with electromagnetic energy, comprising:
    a plurality of antennas adapted to be worn by the patient and located adjacent different portions of the lung; and
    a plurality of sensing units each configured to resolve a change in reflected signals, wherein said sensing units are configured to examine an interrogation volume smaller than a lung, and to resolve a change in reflected signals that is functionally related to a change in respiratory volume in a portion of the lung, wherein each of the sensing units comprises:
        an ultra wide-band (UWB) medical radar transceiver configured to transmit UWB electromagnetic energy towards the portion of lung and to receive reflections of the UWB electromagnetic energy that are reflected back towards the UWB medical radar transceiver after encountering the portion of lung; and
        a high speed sample and hold circuit configured to capture said reflections based on a round trip time of flight of the reflections from the UWB medical radar transceiver; and
    a central processing unit configured to compare information received from each sensing unit to determine differences between different portions of the lung,
    wherein each of the one or more sensing units transmits information about the portions of the lung determined from the sensing unit based on the round trip time of flight,
    further wherein each sensing unit is configured to independently monitor and transmit data about different portions of the lung.

2. An apparatus according to claim 1, wherein each of said sensing units of the apparatus is configured to be located external to the body and to contact the skin of the patient.

3. An apparatus according to claim 1, wherein each of said sensing units further comprises:
    a substrate and at least two antennae mounted to said substrate in a pattern and
    wherein the sensing unit is capable of both transmitting and receiving radiofrequency signals.

4. An apparatus according to claim 1, wherein the transmitted UWB electromagnetic energy has a frequency band extending within 3.1 GHz to 10.6 GHz, ensuring compliance with applicable FCC regulations.

5. The apparatus of claim 1, wherein said at least one of said antennas is adapted to be located in close proximity to the sternum within a three centimeter radius of a center of the sternum so as to simultaneously collect reflected signals caused by the beating of the heart and internal movement derivative of respiration.

6. The apparatus of claim 1, wherein each of the sensing units is configured to integrate said reflections to form an integrated signal to minimize high frequency noise so as to avoid corruption of desired data related to tracking instantaneous respiratory chamber volume.

7. The apparatus of claim 6, wherein each of the sensing units is configured to amplify said integrated signal and pass said amplified signal through a low-pass filter to prevent signal aliasing prior to digitization.

8. The apparatus of claim 1, wherein each of the sensing units is configured to receive reflections from moving boundaries within a target portion of a lung that move with respect to said UWB medical radar transceiver, producing a complex series of time-varying reflections, and wherein said complex series of time-varying reflections are continually processed by said sensing unit to extract information on the mechanical activity of at least one portion of a lung.

9. The apparatus of claim 1, wherein each of the sensing units is configured to determine dielectric values of one or more portions of the lung from the reflections of the electromagnetic energy.

10. The apparatus of claim 1, wherein the sensing units are configured to be positioned over a plurality of locations on the torso of the patient to determine a relative contribution to changes in the spatial configuration of the lung from chest breathing and abdominal breathing.

11. The apparatus of claim 1, wherein the sensing units are positioned over each of the five lung lobes.

12. The apparatus of claim 1, wherein the central processing unit is configured to compare portions of the lung and to present an output indicating a blockage in a region of the lung.

13. The apparatus of claim 1, wherein the sensing units are disposed on a wearable vest.

14. The apparatus of claim 1, further wherein the apparatus determines a pattern of motion of the portion of the lung based on changes in distances of the portion of the lungs over time.

15. The apparatus of claim 1, wherein the high speed sample and hold circuit is part of the UWB medical radar transceiver.

16. An apparatus for determining changes in dielectric or spatial configuration of multiple, different portions of a patient's lungs by interrogating the different portions of the lungs with electromagnetic energy, the apparatus comprising:
    a plurality of antennas each adapted to be worn by the patient and located against the patient; and
    a plurality of sensing units configured to resolve movements of different portions of a patient's lungs, wherein each of the sensing units is configured to examine an interrogation volume smaller than a lung and comprises:
        an ultra wide-band (UWB) medical radar transceiver coupled to one or more of the antennas and configured to transmit ultra wide-band electromagnetic energy towards one of the portions of lung and to receive reflections of the electromagnetic energy that are reflected back towards the UWB medical radar transceiver after encountering the one of the portions of lung, and
        a high speed sample and hold circuit configured to capture said reflections based on a round trip time of flight of the reflections from the UWB medical radar transceiver; and
    a central processing unit configured to compare information received from each sensing unit to determine differences in the relative motion between different portions of the lungs,
    wherein each of the sensing units transmits information about the portion of the lungs determined from the sensing unit based on the round trip time of flight of the reflections, further wherein each sensing unit is configured to independently monitor and transmit data about different portions of the lung.

17. The apparatus of claim 16, further wherein the apparatus determines differences in patterns of motion between the different portions of the lungs based on the changes in the reflections due to changes in the different portions of the lungs over time.

* * * * *